(12) United States Patent
Howard et al.

(10) Patent No.: US 7,557,099 B2
(45) Date of Patent: Jul. 7, 2009

(54) PYRROLOBENZODIAZEPINES AS KEY INTERMEDIATES IN THE SYNTHESIS OF DIMERIC CYTOTOXIC PYRROLOBENZODIAZEPINES

(75) Inventors: Philip Wilson Howard, St Albans (GB); Gyoung-Dong Kang, Worcester Park (GB)

(73) Assignee: Spirogen Limited, Ryde, Isle of Wight (GB)

( * ) Notice: Subject to any disclaimer, the term of this patent is extended or adjusted under 35 U.S.C. 154(b) by 42 days.

(21) Appl. No.: 10/598,482

(22) PCT Filed: Mar. 1, 2005

(86) PCT No.: PCT/GB2005/000770

§ 371 (c)(1),
(2), (4) Date: Feb. 6, 2007

(87) PCT Pub. No.: WO2005/085259

PCT Pub. Date: Sep. 15, 2005

(65) Prior Publication Data

US 2007/0191309 A1      Aug. 16, 2007

(30) Foreign Application Priority Data

Mar. 1, 2004      (GB) .................................. 0404577.9

(51) Int. Cl.
*C07D 519/00*      (2006.01)
*C07D 487/04*      (2006.01)
*A61K 31/55*       (2006.01)

(52) U.S. Cl. ....................................... 514/220; 540/496
(58) Field of Classification Search ................. 540/496; 514/220
See application file for complete search history.

(56) References Cited

U.S. PATENT DOCUMENTS

| | | | |
|---|---|---|---|
| 3,523,941 A | 8/1970 | Leimgruber et al. |
| 3,524,849 A | 8/1970 | Batcho et al. |
| 4,185,016 A | 1/1980 | Takanabe et al. |
| 4,239,683 A | 12/1980 | Takanabe et al. |
| 4,309,437 A | 1/1982 | Ueda et al. |
| 4,450,150 A | 5/1984 | Sidman |
| 5,418,241 A | 5/1995 | Jegham et al. |
| 6,562,806 B1 | 5/2003 | Thurston et al. |
| 6,608,192 B1 | 8/2003 | Thurston et al. |
| 6,660,856 B2 | 12/2003 | Wang |
| 6,747,144 B1 | 6/2004 | Thurston et al. |
| 7,049,311 B1 | 5/2006 | Thurston et al. |
| 7,067,511 B2 | 6/2006 | Thurston et al. |
| 7,265,105 B2 | 9/2007 | Thurston et al. |
| 7,407,951 B2 | 8/2008 | Thurston et al. |
| 2003/0195196 A1 | 10/2003 | Thurston et al. |
| 2004/0092736 A1 | 5/2004 | Thurston et al. |
| 2004/0198722 A1 | 10/2004 | Thurston et al. |
| 2006/0264622 A1 | 11/2006 | Howard et al. |
| 2007/0173497 A1 | 7/2007 | Howard et al. |
| 2007/0185073 A1 | 8/2007 | Howard et al. |
| 2007/0191349 A1 | 8/2007 | Howard et al. |
| 2008/0167293 A1 | 7/2008 | Howard et al. |

FOREIGN PATENT DOCUMENTS

EP      1193270      4/2002

(Continued)

OTHER PUBLICATIONS

Farmer et al. (Tetrahedron Letters (1998), 29(40), 5105-8). Abstract.*

(Continued)

*Primary Examiner*—Bruck Kifle
(74) *Attorney, Agent, or Firm*—Michael Best & Friedrich LLP

(57) ABSTRACT

Compounds and a method of synthesis of compounds of formula (Ia) or (Ib): and salts, solvates, and chemically protected forms thereof, wherein the dotted lines indicate the optional presence of a double bond between C1 and C2 or C2 and C3; $R^2$ and $R^3$ are independently selected from —H, =O, =CH$_2$, —CN, —R, OR, halo, =CH—R, O—SO$_2$—R, CO$_2$R and COR; $R^{10}$ is a carbamate-based nitrogen protecting group; and $R^{11}$ is an oxygen protecting group.

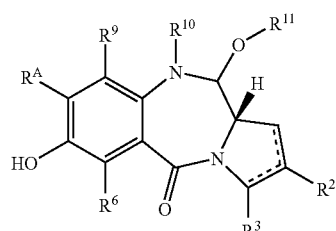

(Ia)

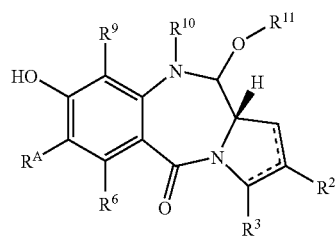

(Ib)

13 Claims, No Drawings

FOREIGN PATENT DOCUMENTS

| | | |
|---|---|---|
| FR | 2027356 | 12/1969 |
| FR | 2586683 D | 3/1987 |
| GB | 1299198 D | 12/1972 |
| JP | 53-82792 | 7/1978 |
| JP | 57131791 | 8/1982 |
| JP | 58180487 | 10/1983 |
| WO | WO 92/19620 D | 11/1992 |
| WO | WO 93/18045 | 9/1993 |
| WO | 00/12506 | 3/2000 |
| WO | 00/12509 | 3/2000 |
| WO | WO 00/12507 | 3/2000 |
| WO | WO 00/12508 | 3/2000 |
| WO | WO 2004/043963 | 5/2004 |
| WO | WO 2005/023814 | 3/2005 |
| WO | 2005/042535 | 5/2005 |
| WO | WO 2005/040170 | 5/2005 |
| WO | WO 2005/085250 | 9/2005 |
| WO | WO 2005/085251 | 9/2005 |
| WO | WO 2005/085259 | 9/2005 |
| WO | WO 2005/085260 | 9/2005 |
| WO | 2005/110423 | 11/2005 |

OTHER PUBLICATIONS

Kamal et al. (Journal of Medicinal Chemistry (2002), 45(21), 4679-4688).*

Adams et al., "Molecular modelling of a sequence-specific DNA-binding agent based on the pyrrolo[2,1-c][1,4]benzodiazepines," Pharm. Pharmacol. Commun. (1999) 5:555-560.

Althius, T.H. and Hess, H. J., "Synthesis and Identification of the Major Metabolites of Prazosin Formed in Dog and Rat," J. Medicinal Chem. (1977) 20(1):146-148.

Arima et al., "Studies on Tomaymycin, a New Antibiotic. I. Isolation and Properties of Tomaymycin," J. Antibiotics (1972) 25:437-444.

Berry, J. M. et al., "Solid-phase synthesis of DNA-interactive pyrrolo[2,1-c][1,4]benzodiazepines," Tetrahedron Letters (2000) 41:6171-6174.

Bose et al., "New Approaches to Pyrrolo[2,1-c][1,4]benzodiazepines: Synthesis, DNA-binding and cytotoxicity of DC-81," Tetrahedron, 48, 751-758 (1992).

Bose, D.S. et al., "Rational Design of a Highly Efficient Irreversible DNA Interstrand Cross-Linking Agent Based on the Pyrrolobenzodiazepine Ring System," J. Am. Chem. Soc., 114, 4939-4941 (1992).

Bose, D.S. et al., "Effect of linker length on DNA-binding affinity, cross-linking efficiency and cytotoxicity of C8 linked pyrrolobenzodiazepine dimers," J. Chem. Soc. Chem. Commun. (1992) 20:1518-1520.

Chen, Z. et al., "A novel approach to the synthesis of cytotoxic C2-C3 unsaturated pyrrolo[2,1-c][1,4]benzodiazepines (PBDs) with conjugated acrylyl C2-substituents," Biorg. Med. Chem. Lett. (2004) 14:1547-1549.

Cooper, N. et al., "Synthesis of novel PBDs as anti-tumour agents," Chem. Commun. (2002) 16:1764-1765.

Courtney, S. M. et al., "A new convenient procedure for the synthesis of pyrrolo[2,1-c][1,4]benzodiazepines", Tetrahedron Letters, vol. 34, No. 33, 5327-28 (1993).

Farmer, J.D. et al., "DNA binding properties of a new class of linked anthramycin analogs,", Chemical Abstracts, Abstract No. 239940r, vol. 114, No. 25, 25 899-903 (1991).

Foloppe, M.P. et al., "DNA-binding properties of pyrrolo[2,1-c][1,4]benzodiazephine N10-C11 amidines," Eur. J. Med. Chem., 31, 407-410 (1996).

Fujisawa Pharmaceutical Co., LTD., Abstract No. 139983k, "Benzodiazepine derivatives", Chemical Abstracts, vol. 99, No. 17, 603 (1983).

Fujisawa Pharmaceutical Co., LTD., Abstract No. 72145x, "Benzodiazepine derivatives", Chemcial Abstracts, vol. 98, No. 9, 638 (1983).

Fujisawa Pharmaceutical Co. LTD., "Benzodiazepine derivatives," SciFinder Scholar, 2-3 (2002).

Fukuyama, T. et al., "Total Synthesis of (+)-Porothramycin B," Tetrahedron Letters, vol. 34, 16, 2577-2580 (1993).

Greene, T.W. and Wuts,P.G.M., Protective Groups in Organic Synthesis, John Wiley & Sons, $2^{nd}$ ed., Ch 7, 315-345 (1991).

Gregson, S. et al., "Synthesis of a novel C2/C2'-exo unsaturated pyrrolobenzodiazepine cross-linking agent with remarkable DNA binding affinity and cytotoxicity," Chemical Communications, 797-798 (1999).

Gregson, S.J. et al., "Effect of C2/C3-endo unsaturation on the cytotoxicity and DNA-binding reactivity of pyrrolo-[2,1-c][1,4]-benzodiazepines," Bioorg. Med. Chem. Lett. (2000) 10(16):1849-1851.

Gregson, S.J. et al., "Design, Synthesis and Evaluation of a Novel Pyrrolobenzodiazepine DNA-Interactive Agent with Highly Efficient Cross-Linking Ability and Potent Cytotoxicity", J. Med. Chem., 44: 737-748 (2001).

Gregson, S.J. et al., "Effect of C2-exo Unsaturation on the Cytotoxicity and DNA-Binding Reactivity of Pyrrolo[2,1-c]1,4]benzodiazepines", Bioorganic & Medicinal Chemistry Letters, 10: 1845-1847 (2000).

Gregson, S.J. et al., "Linker length modulates DNA cross-linking reactivity and cytotoxic potency of C8/C8' ether-linked C2-exo-unsaturated pyrrolo[2,1-c][1,4]benzodiazepine (PBD) dimers," J. Med. Chem. (2004) 1161-1174.

Gregson, S.J. et al., "Synthesis of the first example of a C2-C3/C2'-C3'-endo unsaturated pyrrolo[2,1-c][1,4]benzodiazepine dimer," Biorg. Med. Chem. Lett. (2001) 11:2859-2862.

Gregson, S.J. et al., "Synthesis of the first examples of A-C8/C-C2 amide-linked pyrrolo[2,1-c][1,4]benzodiazepine dimers," Biorg. Med. Chem. Lett. (2003) 13:2277-2280.

Guiotto, A. et al., "Synthesis of novel C7-aryl substituted pyrrolo[2,1-c][1,4]benzodiazepines (PBDs) via Pro-N10-troc protection and suzuki coupling," Bioorganic & Medicinal Chemistry Letters, 8, No. 21, 3017-3018 (1998).

Hara et al., "DC 102, a new glycosidic pyrrolo(1,4)benzodiazepine antibiotic produced by streptomyces sp.", J. Antibiotics, 41, 702-704 (1988).

Hartley, J.A. et al., "An agarose gel method for the determination of DNA interstrand crosslinking applicable to the measurement of the rate of total and 'second arm' crosslink reactions," Anal. Biochem. (1991) 193:131-134.

Hochlowski, J. et al., "Abbeymycin, a new anthramycin-type antibiotic produced by a streptomycete," J. Antibiotics, 40, 145-148 (1987).

Hurley, L. and Needham-Vandevanter, D., "Covalent Binding of Antitumor Antibiotics in the Minor Groove of DNA. Mechanism of Action of CC-1065 and the Pyrrolo(1,4)benzodiazepines," Acc. Chem. Res., 19, 230-237 (1986).

Itoh et al., "Sibanomicin, a new pyrrolo(1,4)benzodiazepine antitumor antibiotic produced by a micromonospora sp." J. Antibiotics, 41, 1281-1284 (1988).

Kamal, A., et al., "An Efficient Synthesis of Pyrrolo[2,1-c][1,4] Benzodiazepine Antibiotics via Reductive Cyclization," Bioorg. Med. Chem. Ltrs, 7, No. 14, 1825-1828 (1997).

Kamal, A., et al., "Synthesis of Pyrrolo [2,1-c][1,4]-Benzodiazepene Antibiotics: Oxidation of Cyclic Secondary Amine with TPAP", Tetrahedron, v. 53, No. 9, 3223-3230 (1997).

Kamal et al., "Synthesis and DNA-binding affinity of A-C8/C-C2 alkoxyamido-linked pyrrolo[2,1-c][1,4]benzodiazepine dimers" Biorg. Med. Chem. Lett. (2003) 13(22):3955-3958.

Kamal, et al., "Synthesis of pyrrolo[2,1-c][1,4]benzodiazepines via reductive cyclization of w-azido carbonyl compounds by TMSI: an efficient preparation of antibiotic DC-81 and its dimers," Biorg. Med. Chem. Lett. (2000) 10:2311-2313.

Kaneko, T. et al., "Bicyclic and tricyclic analogues of anthramycin," J. Med. Chem. (1985) 28:388-392.

Kang, G.-D. et al., "Synthesis of a novel C2-aryl substituted 1,2-unsaturated pyrrolobenzodiazepine," Chem. Commun. (2003) 1688-1689.

Kohn, K., "Anthramycin," Antibiotics III, Springer-Verlag, NY, 3-11 (1975).

Konishi, M. et al., "Chicamycin, a new antitumor antibiotic II. Structure determination of chicamycins A and B," J. Antibiotics, 37, 200-206 (1984).

Kunimoto et al., "Mazethramycin, a new member of anthramycin group antibiotics," *J. Antibiotics*, 33, 665-667 (1980).

Langley, D.R. and Thurston, D.E., "A versatile and efficient synthesis of carbinolamine-containing pyrrolo[1,4]benzodiazepines via the cyclization of N-92-aminobenzoyl)pyrrolidine-2-carboxaldehyde diethyl thioacetals: total synthesis of prothracarcin," *J. Org. Chem.*, 52, 91-97 (1987).

Langlois, N. et al., "Synthesis and cytotoxicity on sensitive and doxorubicin-resistant cell lines of new pyrrolo[2,1-c][1,4]benzodiazepines related to anthramycin," J. Med. Chem. (2001) 44:3754-3757.

Leber, J.D. et al., "A revised structure for sibiromycin," *J. Am. Chem. Soc.*, 110, 2992-2993 (1988).

Leimgruber, W. et al., "Isolation and characterization of anthramycin, a new antitumor antibiotic," *J. Am. Chem. Soc.*, 87, 5791-5793 (1965).

Leimgruber, W. et al., "The structure of anthramycin," *J. Am. Chem. Soc.*, 87, 5793-5795 (1965).

Leimgruber, W. et al., "Total synthesis of anthramycin," *J. Am. Chem. Soc.*, 90, 5641-5643 (1968).

Lown et al., "Molecular Mechanism of Binding of Pyrrolo(1,4)benzodiazepine antitumour agents to deoxyribonucleic acid—anthramycin and tomaymycin," Biochem. Pharmacol. (1979), 28 (13), 2017-2026.

Mori, M. et al., "Total syntheses of prothracarcin and tomaymycin by use of palladium catalyzed carbonylation," Tetrahedron (1986) 42(14):3793-3806.

Mountzouris, J.A. et al., "Comparison of a DSB-120 DNA interstrand cross-linked adduct with the corresponding bis-Tomamycin adduct," J. Med. Chem. (1994) 37:3132-3140.

Nagasaka, T. and Koseki, Y, "Stereoselective Synthesis of Tilivalline," *Journal of Organic Chemistry*, vol. 63, No. 20, 6797-6801 (1998).

Nagasaka, T. et al., "Stereoselective Synthesis of Tilivalline," *Tetrahedron Letters*, 30:14, 1871-1872 (1989).

O'Neil, I.A., et al., "The Synthesis of Functionalized Pyrrolo-[2,1-c][1,4]-Benzodiazepines," *Synlett*, 75-78 (1997).

O'Neil, Chemical Abstract No. 171573p, "The synthesis of Functionalized Pyrrolo-[2,1-c][1,4]-Benzodiazepines", *Chemical Abstracts*, vol. 126, No. 13, 618 (1997).

O'Neil, I.A. et al., "DPPE: A Convenient Replacement for Triphenylphosphine in the Staudinger and Mitsunobu Reactions", *Tetrahedron Letters*, vol. 39, No. 42, 7787-7790 (1998).

Sagnou, M.J. et al., "Design and Synthesis of Novel Pyrrolobenzodiazepine (PDB) Prodrugs for ADEPT and GDEPT," *Bioorganic & Medicinal Chemistry Letters*, 10, 2083-2086 (2000).

Shimizu, K et al., "Prothracarcin, a Novel Antitumor Antibiotic," *J. Antibiotics*, 35, 972-978 (1982).

Smellie, M. et al., "Cellular pharmacology of novel C8-linked anthramycin-based sequence-selective DNA minor groove cross-linking agents," Br. J. Cancer (1994) 70:48-53.

Smellie, M. et al., "Sequence selective recognition of duplex DNA through covalent interstrand cross-linking," Biochem. (2003) 42:8232-8239.

Suggs, J.W. et al., "Synthesis and structure of anthramycin analogs via hydride reduction of dilactams," *Tetrahedron Letters*, 26, No. 40, 4871-4874 (1985).

Takeuchi, T. et al., "Neothramycins A and B, New Antitumor Antibiotics," *J. Antibiotics*, 29, 93-96 (1976).

Tercel, M. et al., "Unsymmetrical DNA cross-linking agents: combination of the CBI and PBD pharmacophores", J. Med. Chem. (2003) 46:2132-2151.

Thurston, D.E. and Thompson, A.S., "The molecular recognition of DNA," *Chem. Brit.*, 26, 767-772 (1990).

Thurston, D.E. and Bose, D.S., "Synthesis of DNA-Interactive Pyrrolo[2,1-c][1,4]benzodiazepines," *Chem. Rev.*, 94:433-465 (1994).

Thurston, D. E., "Advances in the study of Pyrrolo[2,1-c][1,4] benzodiazepine (PBD) Antitumour Antibiotics", *Molecular Aspects of Anticancer Drug-DNA Interaction*, Neidle, S. and Waring, M.J., Eds.; Macmillan Press Ltd, 1:54-88 (1993).

Thurston, D.E. et al., "Effect of A-ring modifications on the DNA-binding behavior and cytotoxicity of pyrrolo[2,1-c][1,4] benzodiazepines", *Journal of Medicinal Chemistry*, 42:1951-1964 (1999).

Thurston, D.E. et al., "Synthesis of Sequence-selective C8-linked Pyrrolo [2,1-c][1,4] Benzodiazepine DNA Interstrand Cross-linking Agent," *J. Org. Chem.*, 61:8141-8147 (1996).

Thurston, D.E. et al., "Synthesis of a novel GC-specific covalent-binding DNA affinity-cleavage agent based on pyrrolobenzodiazepines (PBDs)," Chemical Communications, 563-565 (1996).

Thurston, D.E., "Nucleic acid targeting: therapeutic strategies for the 21st century," Brit. J. Cancer (1999) 80(1):65-85.

Tiberghien, A.C. et al., "Application of the stille coupling reaction to the synthesis of C2-substituted endo-exo unsaturated pyrrolo[2,1-c][1,4]benzodiazepines (PBDs)," Biorg. Med. Chem. Lett. (2004) 14:5041-5044.

Tsunakawa, M. et al., "Porothramycin, a new antibiotic of the anthramycin group: Production, isolation, structure and biological activity," *J. Antibiotics*, 41:1366-1373 (1988).

Umezawa, H. et al., Chemical Abstract No. 4427a, "Mazethramycins" *Chemical Abstracts*, vol. 90, No. 1, 428 (1979).

Umezawa, H. et al., "Mazethramycins ," *SciFinder Scholar*, 2-3 (2002).

Williams, M.A. et al., "Synthesis of conformationally constrained DTPA analogues. Incorporation of the ethylenediamine units as aminopyrrolidines," J. Org. Chem. (1994) 59(13):3616-3625.

Wilson, S.C. et al., "Design and Synthesis of a Novel Epoxide-Containing Pyrrolo[2,1-c][1,4]benzodiazepine (PBD) via a New Cyclization Procedure," *Tetrahedron Letters*, 36, No. 35, 6333-6336 (1995).

Wilson, S.C. et al., "Design, Synthesis, and Evaluation of a Novel Sequence-Selective Epoxide-Containing DNA Cross-Linking Agent Based on the Pyrrolo[2,1-c][1,4]benzodiazepine System", *J. Med. Chem.* 42:4028-4041 (1999).

Weidner-Wells, M.A. et al., "Photochemical approach to the synthesis of the pyrrolo[1,4]benzodiazepine antibiotics," J. Org. Chem. (1989) 54:5746-5758.

* cited by examiner

PYRROLOBENZODIAZEPINES AS KEY INTERMEDIATES IN THE SYNTHESIS OF DIMERIC CYTOTOXIC PYRROLOBENZODIAZEPINES

CROSS-REFERENCE TO RELATED APPLICATIONS

This patent application is a national stage filing under 35 U.S.C. 371 of International Application No. PCT/GB2005/000770, filed on Mar. 1, 2005, which claims foreign priority benefits to United Kingdom Application No. 0404577.9, filed Mar. 1, 2004.

The present invention relates to pyrrolobenzodiazepines (PBDs), and in particular pyrrolobenzodiazepines useful in the synthesis of dimeric compounds.

BACKGROUND TO THE INVENTION

Some pyrrolobenzodiazepines (PBDs) have the ability to recognise and bond to specific sequences of DNA; the preferred sequence is PuGPu. The first PBD antitumour antibiotic, anthramycin, was discovered in 1965 (Leimgruber, et al., *J. Am. Chem. Soc.*, 87, 5793-5795 (1965); Leimgruber, et al., *J. Am. Chem. Soc.*, 87, 5791-5793 (1965)). Since then, a number of naturally occurring PBDs have been reported, and over 10 synthetic routes have been developed to a variety of analogues (Thurston, et al., *Chem. Rev.* 1994, 433-465 (1994)). Family members include abbeymycin (Hochlowski, et al., *J. Antibiotics*, 40, 145-148 (1987)), chicamycin (Konishi, et al., *J. Antibiotics*, 37, 200-206 (1984)), DC-81 (Japanese Patent 58-180 487; Thurston, et al., *Chem. Brit.*, 26, 767-772 (1990); Bose, et al., *Tetrahedron*, 48, 751-758 (1992)), mazethramycin (Kuminoto, et al., *J. Antibiotics*, 33, 665-667 (1980)), neothramycins A and B (Takeuchi, et al., *J. Antibiotics*, 29, 93-96 (1976)), porothramycin (Tsunakawa, et al., *J. Antibiotics*, 41, 1366-1373 (1988)), prothracarcin (Shimizu, et al., *J. Antibiotics*, 29, 2492-2503 (1982); Langley and Thurston, *J. Org. Chem.*, 52, 91-97 (1987)), sibanomicin (DC-102)(Hara, et al., *J. Antibiotics*, 41, 702-704 (1988); Itoh, et al., *J. Antibiotics*, 41, 1281-1284 (1988)), sibiromycin (Leber, et al., *J. Am. Chem. Soc.*, 110, 2992-2993 (1988)) and tomamycin (Arima, et al., *J. Antibiotics*, 25, 437-444 (1972)). PBDs are of the general structure:

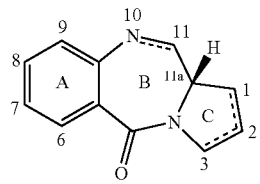

They differ in the number, type and position of substitutents, in both their aromatic A rings and pyrrolo C rings, and in the degree of saturation of the C ring. In the B-ring there is either an imine (N=C), a carbinolamine(NH—CH(OH)), or a carbinolamine methyl ether (NH—CH(OMe)) at the N10-C11 position which is the electrophilic centre responsible for alkylating DNA. All of the known natural products have an (S)-configuration at the chiral C11a position which provides them with a right-handed twist when viewed from the C ring towards the A ring. This gives them the appropriate three-dimensional shape for isohelicity with the minor groove of B-form DNA, leading to a snug fit at the binding site (Kohn, In *Antibiotics III*. Springer-Verlag, New York, pp. 3-11 (1975); Hurley and Needham-VanDevanter, *Acc. Chem. Res.*, 19, 230-237 (1986)). Their ability to form an adduct in the minor groove, enables them to interfere with DNA processing, hence their use as antitumour agents.

The present inventors have previously disclosed, in WO 00/12508, dimeric cytotoxic PBD compounds substituted at the C2 position, for example:

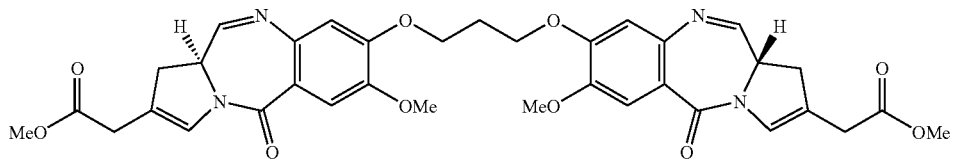

The synthesis of these compounds was achieved by formation of the dimeric backbone comprising the assembled A and C rings linked through the A ring by the diether linking chain. The N10 position was then protected with an Alloc group before a ring closure reaction to form the B ring and subsequent deprotection to give the product. The key stage in this synthesis is described as the ring closure to form the B ring which occurs after the linking of the two A rings with the diether chain.

Using this route, to synthesise a number of dimers having the same monomer groups but different bridging groups require the synthesis of each compound from scratch, i.e. the synthesis route is not able to readily produce a diverse collection of PBD dimers, where the diversity is in the dimer bridge.

DISCLOSURE OF THE INVENTION

The present inventors have developed a key intermediate for the production of dimeric PBDs, which has a hydroxyl group at either the $R^8$ and/or $R^7$ position, a carbamate protecting group at the N10 position and a protected hydroxy group at the C11 position.

In a first aspect, the present invention comprises a compound with the formula Ia or Ib:

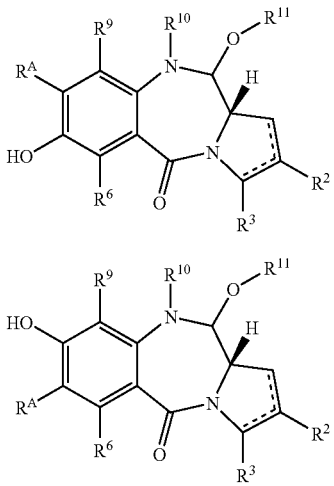

Ia

Ib wherein:
the dotted lines indicate the optional presence of a double bond between C1 and C2 or C2 and C3;

$R^2$ and $R^3$ are independently selected from —H, =O, =CH$_2$, —CN, —R, OR, halo, =CH—R, O—SO$_2$—R, CO$_2$R and COR;

$R^6$ and $R^9$ are independently selected from H, R, OH, OR, SH, SR, NH$_2$, NHR, NRR', nitro, Me$_3$Sn and halo;

where R and R' are independently selected from optionally substituted $C_{1-12}$ alkyl, $C_{3-20}$ heterocyclyl and $C_{5-20}$ aryl groups;

$R^A$ is selected from H, R, OR, SH, SR, NH$_2$, NHR, NHRR', nitro, Me$_3$Sn and halo;

$R^{10}$ is a carbamate-based nitrogen protecting group;

$R^{11}$ is an oxygen protecting group.

In a second aspect, the present invention comprises a method of synthesising a compound of formula Ia or Ib as defined in the first aspect of the invention from a compound of formula IIa or IIb respectively:

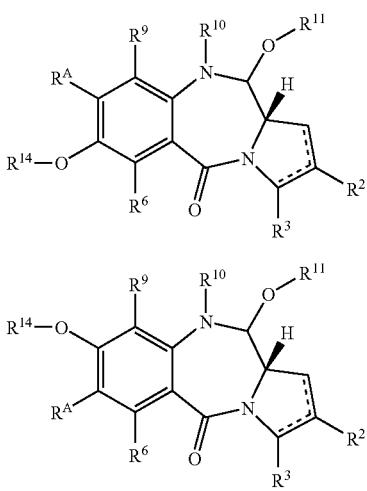

IIa

IIb wherein $R^A$, $R^2$, $R^3$, $R^6$, $R^9$, $R^{10}$ and $R^{11}$ are as defined in the first aspect; $R^{14}$ is an oxygen protecting group which is orthogonal to $R^{11}$.

In a third aspect, the present invention comprises a method of synthesising a compound of formula IIIa or IIIb:

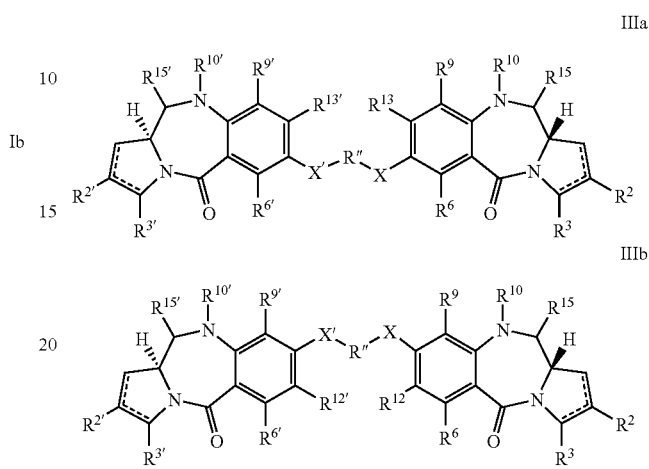

IIIa

IIIb or a solvate thereof, from a compound of formula Ia or Ib as defined in the first aspect, wherein $R^6$, $R^7$, $R^8$, and $R^9$ are as defined in the first aspect;

$R^{12}$ and $R^{13}$ are independently selected from H, R, OH, OR, SH, SR, NH$_2$, NHR, NRR', nitro, Me$_3$Sn and halo;

$R^{10}$ is as defined in the first aspect and $R^{15}$ is either O—$R^{11}$, wherein $R^{11}$ is as defined in the first aspect, or OH, or $R^{10}$ and $R^{15}$ together form a double bond between N10 and C11; and where R" is a $C_{3-12}$ alkylene group, which chain may be interrupted by one or more heteroatoms, e.g. O, S, NH, and/or aromatic rings, e.g. benzene or pyridine, and each X is independently selected from O, S, or NH;

$R^{2'}$, $R^{3'}$, $R^{6'}$, $R^{9'}$, $R^{10'}$, $R^{12'}$, $R^{13'}$ and $R^{15'}$ are all independently selected from the same lists as previously defined for $R^2$, $R^3$, $R^6$, $R^9$, $R^{10}$, $R^{12}$, $R^{13}$ and $R^{15}$ respectively.

Further aspects of the present invention relate to novel compounds of formula IIIa or IIIb (including solvates thereof when $R^{10}$ and $R^{15}$ form a double bond between N10 and C11, and pharmaceutical salts thereof), their use in methods of therapy (particularly in treating proliferative diseases), pharmaceutical compositions comprising these, and their use in the manufacture of a medicament for the treatment of a proliferative disease.

Definitions

Carbamate-Based Nitrogen Protecting Groups

Carbamate-based nitrogen protecting groups are well known in the art, and have the following structure:

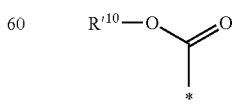

wherein $R'^{10}$ is R as defined above. A large number of suitable groups are described on pages 503 to 549 of Greene, T. W. and Wuts, G. M., *Protective Groups in Organic Synthesis*, 3rd Edition, John Wiley & Sons, Inc., 1999, which is incorporated herein by reference.

Particularly preferred protecting groups include Alloc, Troc, Fmoc, CBz, Teoc, BOC, Doc, Hoc, TcBOC, 1-Adoc and 2-Adoc.

Also suitable for use in the present invention are nitrogen protecting group which can be removed in vivo (e.g. enzymatically, using light) as described in WO 00/12507, which is incorporated herein by reference. Examples of these protecting groups include:

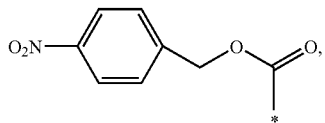

which is nitroreductase labile (e.g. using ADEPT/GDEPT);

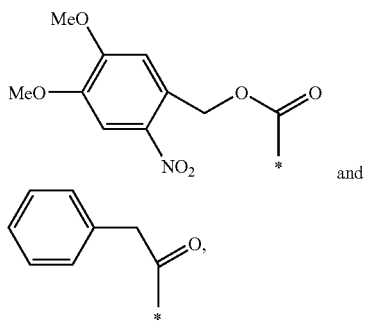

which are photolabile; and

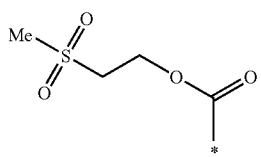

which is glutathione labile (e.g. using NPEPT).

Oxygen Protecting Groups

Oxygen protecting groups are well known in the art. A large number of suitable groups are described on pages 23 to 200 of Greene, T. W. and Wuts, G. M., Protective Groups in Organic Synthesis, 3rd Edition, John Wiley & Sons, Inc., 1999, which is incorporated herein by reference.

Classes of particular interest include silyl ethers, methyl ethers, alkyl ethers, benzyl ethers, esters, benzoates, carbonates, and sulfonates.

Preferred oxygen protecting groups include TBS, THP for the C11 oxygen atom, and benzyl ether for the C7 or C8 oxygen atom (where present).

As mentioned above the oxygen protecting group $R^{14}$ should be orthogonal to the oxygen protecting group $R^{11}$. Protecting groups which are orthogonal to one another may each be removed using reagents or conditions which do not remove the other protecting group.

It may also be preferred that any protecting groups used during the synthesis and use of compounds of formula I are orthogonal to one another. However, it is often not necessary, but may be desirable, for the carbamate-based nitrogen protecting group and $R^{11}$ to be orthogonal to one another, depending on whether the compound of formula IIIa or IIIb is to be used with the nitrogen protecting group in place.

Substituents

The phrase "optionally substituted" as used herein, pertains to a parent group which may be unsubstituted or which may be substituted.

Unless otherwise specified, the term "substituted" as used herein, pertains to a parent group which bears one or more substitutents. The term "substitutent" is used herein in the conventional sense and refers to a chemical moiety which is covalently attached to, or if appropriate, fused to, a parent group. A wide variety of substitutents are well known, and methods for their formation and introduction into a variety of parent groups are also well known.

Examples of substitutents are described in more detail below.

$C_{1-12}$ alkyl: The term "$C_{1-12}$ alkyl" as used herein, pertains to a monovalent moiety obtained by removing a hydrogen atom from a carbon atom of a hydrocarbon compound having from 1 to 12 carbon atoms, which may be aliphatic or alicyclic, and which may be saturated or unsaturated (e.g. partially unsaturated, fully unsaturated). Thus, the term "alkyl" includes the sub-classes alkenyl, alkynyl, cycloalkyl, etc., discussed below.

Examples of saturated alkyl groups include, but are not limited to, methyl ($C_1$), ethyl ($C_2$), propyl ($C_3$), butyl ($C_4$), pentyl ($C_5$), hexyl ($C_6$) and heptyl ($C_7$).

Examples of saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$) and n-heptyl ($C_7$).

Examples of saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

$C_{2-12}$ Alkenyl: The term "$C_{2-12}$ alkenyl" as used herein, pertains to an alkyl group having one or more carbon-carbon double bonds.

Examples of unsaturated alkenyl groups include, but are not limited to, ethenyl (vinyl, —CH═CH$_2$), 1-propenyl (—CH═CH—CH$_3$), 2-propenyl (allyl, —CH—CH═CH$_2$), isopropenyl (1-methylvinyl, —C(CH$_3$)═CH$_2$), butenyl ($C_4$), pentenyl ($C_5$), and hexenyl ($C_6$).

$C_{2-12}$ alkynyl: The term "$C_{2-12}$ alkynyl" as used herein, pertains to an alkyl group having one or more carbon-carbon triple bonds.

Examples of unsaturated alkynyl groups include, but are not limited to, ethynyl (ethinyl, —C≡CH) and 2-propynyl (propargyl, —CH$_2$—C≡CH).

$C_{3-12}$ cycloalkyl: The term "$C_{3-12}$ cycloalkyl" as used herein, pertains to an alkyl group which is also a cyclyl group; that is, a monovalent moiety obtained by removing a hydrogen atom from an alicyclic ring atom of a cyclic hydrocarbon (carbocyclic) compound, which moiety has from 3 to 7 carbon atoms, including from 3 to 7 ring atoms.

Examples of cycloalkyl groups include, but are not limited to, those derived from:

saturated monocyclic hydrocarbon compounds: cyclopropane ($C_3$), cyclobutane ($C_4$), cyclopentane ($C_5$), cyclohexane ($C_6$), cycloheptane ($C_7$), methylcyclopropane ($C_4$), dimethylcyclopropane ($C_5$), methylcyclobutane ($C_5$), dimethylcyclobutane ($C_6$), methylcyclopentane ($C_6$), dimethylcyclopentane ($C_7$) and methylcyclohexane ($C_7$);

unsaturated monocyclic hydrocarbon compounds: cyclopropene ($C_3$), cyclobutene ($C_4$), cyclopentene ($C_5$), cyclohexene ($C_6$), methylcyclopropene ($C_4$), dimethylcyclopropene ($C_5$) methylcyclobutene ($C_5$), dimethylcyclobutene ($C_6$), methylcyclopentene ($C_6$), dimethylcyclopentene ($C_7$) and methylcyclohexene ($C_7$); and saturated polycyclic hydrocarbon compounds: norcarane ($C_7$), norpinane ($C_7$), norbornane ($C_7$).

$C_{3-20}$ heterocyclyl: The term "$C_{3-20}$ heterocyclyl" as used herein, pertains to a monovalent moiety obtained by removing a hydrogen atom from a ring atom of a heterocyclic compound, which moiety has from 3 to 20 ring atoms, of which from 1 to 10 are ring heteroatoms. Preferably, each ring has from 3 to 7 ring atoms, of which from 1 to 4 are ring heteroatoms.

In this context, the prefixes (e.g. $C_{3-20}$, $C_{3-7}$, $C_{5-6}$, etc.) denote the number of ring atoms, or range of number of ring atoms, whether carbon atoms or heteroatoms. For example, the term "$C_{5-6}$heterocyclyl", as used herein, pertains to a heterocyclyl group having 5 or 6 ring atoms.

Examples of monocyclic heterocyclyl groups include, but are not limited to, those derived from:

$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);

$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);

$S_1$: thiirane ($C_3$), thietane ($C_4$), thiolane (tetrahydrothiophene) ($C_5$) thiane (tetrahydrothiopyran) ($C_6$), thiepane ($C_7$);

$O_2$: dioxolane ($C_5$), dioxane ($C_6$), and dioxepane ($C_7$);

$O_3$: trioxane ($C_6$);

$N_2$: imidazolidine ($C_5$), pyrazolidine (diazolidine) ($C_5$), imidazoline ($C_5$), pyrazoline (dihydropyrazole) ($C_5$), piperazine ($C_6$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);

$N_1S_1$: thiazoline ($C_5$), thiazolidine ($C_5$), thiomorpholine ($C_6$);

$N_2O_1$: oxadiazine ($C_6$);

$O_1S_1$: oxathiole ($C_5$) and oxathiane (thioxane) ($C_6$); and, $N_1O_1S_1$: oxathiazine ($C_6$).

Examples of substituted monocyclic heterocyclyl groups include those derived from saccharides, in cyclic form, for example, furanoses ($C_5$), such as arabinofuranose, lyxofuranose, ribofuranose, and xylofuranse, and pyranoses ($C_6$), such as allopyranose, altropyranose, glucopyranose, mannopyranose, gulopyranose, idopyranose, galactopyranose, and talopyranose.

$C_{5-20}$ aryl: The term "$C_{5-20}$ aryl", as used herein, pertains to a monovalent moiety obtained by removing a hydrogen atom from an aromatic ring atom of an aromatic compound, which moiety has from 3 to 20 ring atoms. Preferably, each ring has from 5 to 7 ring atoms.

In this context, the prefixes (e.g. $C_{3-20}$, $C_{5-7}$, $C_{5-6}$, etc.) denote the number of ring atoms, or range of number of ring atoms, whether carbon atoms or heteroatoms. For example, the term "$C_{5-6}$ aryl" as used herein, pertains to an aryl group having 5 or 6 ring atoms.

The ring atoms may be all carbon atoms, as in "carboaryl groups". Examples of carboaryl groups include, but are not limited to, those derived from benzene (i.e. phenyl) ($C_6$), naphthalene ($C_{10}$), azulene ($C_{10}$), anthracene ($C_{14}$), phenanthrene ($C_{14}$), naphthacene ($C_{18}$), and pyrene ($C_{16}$).

Examples of aryl groups which comprise fused rings, at least one of which is an aromatic ring, include, but are not limited to, groups derived from indane (e.g. 2,3-dihydro-1H-indene) ($C_9$), indene ($C_9$), isoindene ($C_9$), tetraline (1,2,3,4-tetrahydronaphthalene ($C_{10}$), acenaphthene ($C_{12}$), fluorene ($C_{13}$), phenalene ($C_{13}$), acephenanthrene ($C_{15}$), and aceanthrene ($C_{16}$).

Alternatively, the ring atoms may include one or more heteroatoms, as in "heteroaryl groups". Examples of monocyclic heteroaryl groups include, but are not limited to, those derived from:

$N_1$: pyrrole (azole) ($C_5$), pyridine (azine) ($C_6$);

$O_1$: furan (oxole) ($C_5$);

$S_1$: thiophene (thiole) ($C_5$);

$N_1O_1$: oxazole ($C_5$), isoxazole ($C_5$), isoxazine ($C_6$);

$N_2O_1$: oxadiazole (furazan) ($C_5$);

$N_3O_1$: oxatriazole ($C_5$);

$N_1S_1$: thiazole ($C_5$), isothiazole ($C_5$);

$N_2$: imidazole (1,3-diazole) ($C_5$), pyrazole (1,2-diazole) ($C_5$), pyridazine (1,2-diazine) ($C_6$), pyrimidine (1,3-diazine) ($C_6$) (e.g., cytosine, thymine, uracil), pyrazine (1,4-diazine) ($C_6$);

$N_3$: triazole ($C_5$), triazine ($C_6$); and, $N_4$: tetrazole ($C_5$).

Examples of heteroaryl which comprise fused rings, include, but are not limited to:

$C_9$ (with 2 fused rings) derived from benzofuran ($O_1$), isobenzofuran ($O_1$), indole ($N_1$), isoindole ($N_1$), indolizine ($N_1$), indoline ($N_1$), isoindoline ($N_1$), purine ($N_4$) (e.g., adenine, guanine), benzimidazole ($N_2$), indazole ($N_2$), benzoxazole ($N_1O_1$), benzisoxazole ($N_1O_1$), benzodioxole ($O_2$), benzofurazan ($N_2O_1$), benzotriazole ($N_3$), benzothiofuran ($S_1$), benzothiazole ($N_1S_1$), benzothiadiazole ($N_2S$);

$C_{10}$ (with 2 fused rings) derived from chromene ($O_1$), isochromene ($O_1$), chroman ($O_1$), isochroman ($O_1$), benzodioxan ($O_2$), quinoline ($N_1$), isoquinoline ($N_1$), quinolizine ($N_1$), benzoxazine ($N_1O_1$), benzodiazine ($N_2$), pyridopyridine ($N_2$), quinoxaline ($N_2$), quinazoline ($N_2$), cinnoline ($N_2$), phthalazine ($N_2$), naphthyridine ($N_2$), pteridine ($N_4$);

$C_{11}$ (with 2 fused rings) derived from benzodiazepine ($N_2$);

$C_{13}$ (with 3 fused rings) derived from carbazole ($N_1$), dibenzofuran ($O_1$), dibenzothiophene ($S_1$), carboline ($N_2$), perimidine ($N_2$), pyridoindole ($N_2$); and, $C_{14}$ (with 3 fused rings) derived from acridine ($N_1$), xanthene ($O_1$), thioxanthene ($S_1$), oxanthrene ($O_2$), phenoxathiin ($O_1S_1$), phenazine ($N_2$), phenoxazine ($N_1O_1$), phenothiazine ($N_1S_1$), thianthrene ($S_2$), phenanthridine ($N_1$), phenanthroline ($N_2$), phenazine ($N_2$).

The above groups, whether alone or part of another substitutent, may themselves optionally be substituted with one or more groups selected from themselves and the additional substitutents listed below.

Halo: —F, —Cl, —Br, and —I.

Hydroxy: —OH.

Ether: —OR, wherein R is an ether substituent, for example, a $C_{1-7}$ alkyl group (also referred to as a $C_{1-7}$ alkoxy group, discussed below), a $C_{3-20}$ heterocyclyl group (also referred to as a $C_{3-20}$ heterocyclyloxy group), or a $C_{5-20}$ aryl group (also referred to as a $C_{5-20}$ aryloxy group), preferably a $C_{1-7}$alkyl group.

Alkoxy: —OR, wherein R is an alkyl group, for example, a $C_{1-7}$ alkyl group. Examples of $C_{1-7}$ alkoxy groups include, but are not limited to, —OMe (methoxy), —OEt (ethoxy), —O(nPr) (n-propoxy), —O(iPr) (isopropoxy), —O(nBu) (n-butoxy), —O(sBu) (sec-butoxy), —O(iBu) (isobutoxy), and —O(tBu) (tert-butoxy).

Acetal: —CH(OR$^1$)(OR$^2$), wherein R$^1$ and R$^2$ are independently acetal substitutents, for example, a $C_{1-7}$ alkyl group, a $C_{3-20}$ heterocyclyl group, or a $C_{5-20}$ aryl group, preferably a $C_{1-7}$ alkyl group, or, in the case of a "cyclic" acetal group, R$^1$ and R$^2$, taken together with the two oxygen atoms to which they are attached, and the carbon atoms to which they are attached, form a heterocyclic ring having from 4 to 8 ring atoms. Examples of acetal groups include, but are not limited to, —CH(OMe)$_2$, —CH(OEt)$_2$, and —CH(OMe)(OEt).

Hemiacetal: —CH(OH)(OR$^1$), wherein R$^1$ is a hemiacetal substitutent, for example, a $C_{1-7}$ alkyl group, a $C_{3-20}$ heterocyclyl group, or a $C_{5-20}$ aryl group, preferably a $C_{1-7}$ alkyl group. Examples of hemiacetal groups include, but are not limited to, —CH(OH)(OMe) and —CH(OH)(OEt).

Ketal: —CR(OR$^1$)(OR$^2$), where R$^1$ and R$^2$ are as defined for acetals, and R is a ketal substituent other than hydrogen, for example, a $C_{1-7}$ alkyl group, a $C_{3-20}$ heterocyclyl group, or a $C_{5-20}$ aryl group, preferably a $C_{1-7}$ alkyl group. Examples ketal groups include, but are not limited to, —C(Me)(OMe)$_2$, —C(Me)(OEt)$_2$, —C(Me)(OMe)(OEt), —C(Et)(OMe)$_2$, —C(Et)(OEt)$_2$, and —C(Et)(OMe)(OEt).

Hemiketal: —CR(OH)(OR$^1$), where R$^1$ is as defined for hemiacetals, and R is a hemiketal substituent other than hydrogen, for example, a $C_{1-7}$ alkyl group, a $C_{3-20}$ heterocyclyl group, or a $C_{5-20}$ aryl group, preferably a $C_{1-7}$ alkyl group. Examples of hemiacetal groups include, but are not limited to, —C(Me)(OH)(OMe), —C(Et)(OH)(OMe), —C(Me)(OH)(OEt), and —C(Et)(OH)(OEt).

Oxo (keto, -one): =O.

Thione (thioketone): =S.

Imino (imine): =NR, wherein R is an imino substituent, for example, hydrogen, $C_{1-7}$ alkyl group, a $C_{3-20}$ heterocyclyl group, or a $C_{5-20}$ aryl group, preferably hydrogen or a $C_{1-7}$ alkyl group. Examples of ester groups include, but are not limited to, =NH, =NMe, =NEt, and =NPh.

Formyl (carbaldehyde, carboxaldehyde): —C(=O)H.

Acyl (keto): —C(=O)R, wherein R is an acyl substituent, for example, a $C_{1-7}$ alkyl group (also referred to as $C_{1-7}$ alkylacyl or $C_{1-7}$ alkanoyl), a $C_{3-20}$ heterocyclyl group (also referred to as $C_{3-20}$ heterocyclylacyl), or a $C_{5-20}$ aryl group (also referred to as $C_{5-20}$ arylacyl), preferably a $C_{1-7}$ alkyl group. Examples of acyl groups include, but are not limited to, —C(=O)CH$_3$ (acetyl), —C(=O)CH$_2$CH$_3$ (propionyl), —C(=O)C(CH$_3$)$_3$ (t-butyryl), and —C(=O)Ph (benzoyl, phenone).

Carboxy (carboxylic acid): —C(=O)OH.

Thiocarboxy (thiocarboxylic acid): —C(=S)SH.

Thiolocarboxy (thiolocarboxylic acid): —C(=O)SH.

Thionocarboxy (thionocarboxylic acid): —C(=S)OH.

Imidic acid: —C(=NH)OH.

Hydroxamic acid: —C(=NOH)OH.

Ester (carboxylate, carboxylic acid ester, oxycarbonyl): —C(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —C(=O)OCH$_3$, —C(=O)OCH$_2$CH$_3$, —C(=O)OC(CH$_3$)$_3$, and —C(=O)OPh.

Acyloxy (reverse ester): —OC(=O)R, wherein R is an acyloxy substitutent, for example, a $C_{1-7}$ alkyl group, a $C_{3-20}$ heterocyclyl group, or a $C_{5-20}$ aryl group, preferably a $C_{1-7}$ alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

Oxycarboyloxy: —OC(=O)OR, wherein R is an ester substitutent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —OC(=O)OCH$_3$, —OC(=O)OCH$_2$CH$_3$, —OC(=O)OC(CH$_3$)$_3$, and —OC(=O)OPh.

Amino: —NR$^1$R$^2$, wherein R$^1$ and R$^2$ are independently amino substitutents, for example, hydrogen, a $C_{1-7}$ alkyl group (also referred to as $C_{1-7}$ alkylamino or di-$C_{1-7}$ alkylamino), a $C_{3-20}$ heterocyclyl group, or a $C_{5-20}$ aryl group, preferably H or a $C_{1-7}$ alkyl group, or, in the case of a "cyclic" amino group, R$^1$ and R$^2$, taken together with the nitrogen atom to which they are attached, form a heterocyclic ring having from 4 to 8 ring atoms. Amino groups may be primary (—NH$_2$), secondary (—NHR$^1$), or tertiary (—NHR$^1$R$^2$), and in cationic form, may be quaternary (—$^+$NR$^1$R$^2$R$^3$). Examples of amino groups include, but are not limited to, —NH$_2$, —NHCH$_3$, —NHC(CH$_3$)$_2$, —N(CH$_3$)$_2$, —N(CH$_2$CH$_3$)$_2$, and —NHPh. Examples of cyclic amino groups include, but are not limited to, aziridino, azetidino, pyrrolidino, piperidino, piperazino, morpholino, and thiomorpholino.

Amido (carbamoyl, carbamyl, aminocarbonyl, carboxamide): —C(=O)NR$^1$R$^2$, wherein R$^1$ and R$^2$ are independently amino substitutents, as defined for amino groups. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$, as well as amido groups in which R$^1$ and R$^2$, together with the nitrogen atom to which they are attached, form a heterocyclic structure as in, for example, piperidinocarbonyl, morpholinocarbonyl, thiomorpholinocarbonyl, and piperazinocarbonyl.

Thioamido (thiocarbamyl): —C(=S)NR$^1$R$^2$, wherein R$^1$ and R$^2$ are independently amino substitutents, as defined for amino groups. Examples of amido groups include, but are not limited to, —C(=S)NH$_2$, —C(=S)NHCH$_3$, —C(=S)N(CH$_3$)$_2$, and —C(=S)NHCH$_2$CH$_3$.

Acylamido (acylamino): —NR$^1$C(=O)R$^2$, wherein R$^1$ is an amide substituent, for example, hydrogen, a $C_{1-7}$ alkyl group, a $C_{3-20}$ heterocyclyl group, or a $C_{5-20}$ aryl group, preferably hydrogen or a $C_{1-7}$ alkyl group, and R$^2$ is an acyl substitutent, for example, a $C_{1-7}$ alkyl group, a $C_{3-20}$ heterocyclyl group, or a $C_{5-20}$ aryl group, preferably hydrogen or a $C_{1-7}$ alkyl group. Examples of acylamide groups include, but are not limited to, —NHC(=O)CH$_3$ —NHC(=O)CH$_2$CH$_3$, and —NHC(=O)Ph. R$^1$ and R$^2$ may together form a cyclic structure, as in, for example, succinimidyl, maleimidyl, and phthalimidyl:

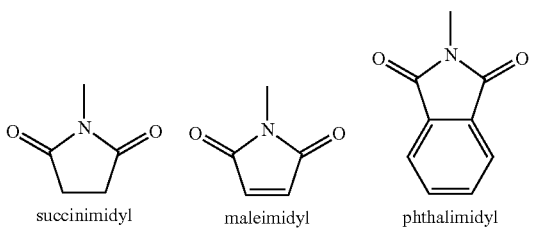

succinimidyl    maleimidyl    phthalimidyl

Aminocarbonyloxy: —OC(=O)NR$^1$R$^2$, wherein R$^1$ and R$^2$ are independently amino substitutents, as defined for amino groups. Examples of aminocarbonyloxy groups include, but are not limited to, —OC(=O)NH$_2$, —OC(=O)NHMe, —OC(=O)NMe$_2$, and —OC(=O)NEt$_2$.

Ureido: —N(R$^1$)CONR$^2$R$^3$ wherein R$^2$ and R$^3$ are independently amino substitutents, as defined for amino groups, and R$^1$ is a ureido substitutent, for example, hydrogen, a C$_{1-7}$ alkyl group, a C$_{3-20}$ heterocyclyl group, or a C$_{5-20}$ aryl group, preferably hydrogen or a C$_{1-7}$ alkyl group. Examples of ureido groups include, but are not limited to, —NHCONH$_2$, —NHCONHMe, —NHCONHEt, —NHCONMe$_2$, —NHCONEt$_2$, —NMeCONH$_2$, —NMeCONHMe, —NMeCONHEt, —NMeCONMe$_2$, and —NMeCONEt$_2$.

Guanidino: —NH—C(=NH)NH$_2$.

Tetrazolyl: a five membered aromatic ring having four nitrogen atoms and one carbon atom,

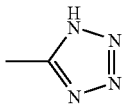

Imino: =NR, wherein R is an imino substitutent, for example, for example, hydrogen, a C$_{1-7}$ alkyl group, a C$_{3-20}$ heterocyclyl group, or a C$_{5-20}$ aryl group, preferably H or a C$_{1-7}$ alkyl group. Examples of imino groups include, but are not limited to, =NH, =NMe, and =NEt.

Amidine (amidino): —C(=NR)NR$_2$, wherein each R is an amidine substitutent, for example, hydrogen, a C$_{1-7}$ alkyl group, a C$_{3-20}$ heterocyclyl group, or a C$_{5-20}$ aryl group, preferably H or a C$_{1-7}$ alkyl group. Examples of amidine groups include, but are not limited to, —C(=NH)NH$_2$, —C(=NH)NMe$_2$, and —C(=NMe)NMe$_2$.

Nitro: —NO$_2$.

Nitroso: —NO.

Azido: —N$_3$.

Cyano (nitrile, carbonitrile): —CN.

Isocyano: —NC.

Cyanato: —OCN.

Isocyanato: —NCO.

Thiocyano (thiocyanato): —SCN.

Isothiocyano (isothiocyanato): —NCS.

Sulfhydryl (thiol, mercapto): —SH.

Thioether (sulfide): —SR, wherein R is a thioether substitutent, for example, a C$_{1-7}$ alkyl group (also referred to as a C$_{1-7}$alkylthio group), a C$_{3-20}$ heterocyclyl group, or a C$_{5-20}$ aryl group, preferably a C$_{1-7}$ alkyl group. Examples of C$_{1-7}$alkylthio groups include, but are not limited to, —SCH$_3$ and —SCH$_2$CH$_3$.

Disulfide: —SS—R, wherein R is a disulfide substitutent, for example, a C$_{1-7}$ alkyl group, a C$_{3-20}$ heterocyclyl group, or a C$_{5-20}$ aryl group, preferably a C$_{1-7}$ alkyl group (also referred to herein as C$_{1-7}$ alkyl disulfide). Examples of C$_{1-7}$ alkyl disulfide groups include, but are not limited to, —SSCH$_3$ and —SSCH$_2$CH$_3$.

Sulfine (sulfinyl, sulfoxide): —S(=O)R, wherein R is a sulfine substitutent, for example, a C$_{1-7}$ alkyl group, a C$_{3-20}$ heterocyclyl group, or a C$_{5-20}$ aryl group, preferably a C$_{1-7}$ alkyl group. Examples of sulfine groups include, but are not limited to, —S(=O)CH$_3$ and —S(=O)CH$_2$CH$_3$.

Sulfone (sulfonyl): —S(=O)$_2$R, wherein R is a sulfone substitutent, for example, a C$_{1-7}$ alkyl group, a C$_{3-20}$ heterocyclyl group, or a C$_{5-20}$ aryl group, preferably a C$_{1-7}$ alkyl group, including, for example, a fluorinated or perfluorinated C$_{1-7}$ alkyl group. Examples of sulfone groups include, but are not limited to, —S(=O)$_2$CH$_3$ (methanesulfonyl, mesyl), —S(=O)$_2$CF$_3$ (triflyl), —S(=O)$_2$CH$_2$CH$_3$ (esyl), —S(=O)$_2$C$_4$F$_9$ (nonaflyl), —S(=O)$_2$CH$_2$CF$_3$ (tresyl), —S(=O)$_2$CH$_2$CH$_2$NH$_2$ (tauryl), —S(=O)$_2$Ph (phenylsulfonyl, besyl), 4-methylphenylsulfonyl (tosyl), 4-chlorophenylsulfonyl (closyl), 4-bromophenylsulfonyl (brosyl), 4-nitrophenyl (nosyl), 2-naphthalenesulfonate (napsyl), and 5-dimethylaminonaphthalen-1-ylsulfonate (dansyl).

Sulfinic acid (sulfino): —S(=O)OH, —SO$_2$H.

Sulfonic acid (sulfo): —S(=O)$_2$OH, —SO$_3$H.

Sulfinate (sulfinic acid ester): —S(=O)OR; wherein R is a sulfinate substitutent, for example, a C$_{1-7}$ alkyl group, a C$_{3-20}$ heterocyclyl group, or a C$_{5-20}$ aryl group, preferably a C$_{1-7}$ alkyl group. Examples of sulfinate groups include, but are not limited to, —S(=O)OCH$_3$ (methoxysulfinyl; methyl sulfinate) and —S(=O)OCH$_2$CH$_3$ (ethoxysulfinyl; ethyl sulfinate).

Sulfonate (sulfonic acid ester): —S(=O)$_2$OR, wherein R is a sulfonate substitutent, for example, a C$_{1-7}$alkyl group, a C$_{3-20}$ heterocyclyl group, or a C$_{5-20}$ aryl group, preferably a C$_{1-7}$alkyl group. Examples of sulfonate groups include, but are not limited to, —S(=O)$_2$OCH$_3$ (methoxysulfonyl; methyl sulfonate) and —S(=O)$_2$OCH$_2$CH$_3$ (ethoxysulfonyl; ethyl sulfonate).

Sulfinyloxy: —OS(=O)R, wherein R is a sulfinyloxy substitutent, for example, a C$_{1-7}$alkyl group, a C$_{3-20}$ heterocyclyl group, or a C$_{5-20}$ aryl group, preferably a C$_{1-7}$alkyl group. Examples of sulfinyloxy groups include, but are not limited to, —OS(=O)CH$_3$ and —OS(=O)CH$_2$CH$_3$.

Sulfonyloxy: —OS(=O)$_2$R, wherein R is a sulfonyloxy substitutent, for example, a C$_{1-7}$alkyl group, a C$_{3-20}$ heterocyclyl group, or a C$_{5-20}$ aryl group, preferably a C$_{1-7}$ alkyl group. Examples of sulfonyloxy groups include, but are not limited to, —OS(=O)$_2$CH$_3$ (mesylate) and —OS(=O)$_2$CH$_2$CH$_3$ (esylate).

Sulfate: —OS(=O)$_2$OR; wherein R is a sulfate substitutent, for example, a C$_{1-7}$alkyl group, a C$_{3-20}$ heterocyclyl group, or a C$_{5-20}$ aryl group, preferably a C$_{1-7}$ alkyl group. Examples of sulfate groups include, but are not limited to, —OS(=O)$_2$OCH$_3$ and —SO(=O)$_2$OCH$_2$CH$_3$.

Sulfamyl (sulfamoyl; sulfinic acid amide; sulfinamide): —S(=O)NR$^1$R$^2$, wherein R$^1$ and R$^2$ are independently amino substitutents, as defined for amino groups. Examples of sulfamyl groups include, but are not limited to, —S(=O)NH$_2$, —S(=O)NH(CH$_3$), —S(=O)N(CH$_3$)$_2$, —S(=O)NH(CH$_2$CH$_3$), —S(=O)N(CH$_2$CH$_3$)$_2$, and —S(=O)NHPh.

Sulfonamido (sulfinamoyl; sulfonic acid amide; sulfonamide): —S(=O)$_2$NR$^1$R$^2$, wherein R$^1$ and R$^2$ are independently amino substitutents, as defined for amino groups. Examples of sulfonamido groups include, but are not limited to, —S(=O)$_2$NH$_2$, —S(=O)$_2$NH(CH$_3$), —S (=O)$_2$N(CH$_3$)$_2$, —S(=O)$_2$NH(CH$_2$CH$_3$), —S(=O)$_2$N(CH$_2$CH$_3$)$_2$, and —S(=O)$_2$NHPh.

Sulfamino: —NR$^1$S(=O)$_2$OH, wherein R$^1$ is an amino substitutent, as defined for amino groups. Examples of sulfamino groups include, but are not limited to, —NHS(=O)$_2$ OH and —N(CH$_3$)S(=O)$_2$OH.

Sulfonamino: —NR$^1$S(=O)$_2$R, wherein R$^1$ is an amino substitutent, as defined for amino groups, and R is a sulfonamino substitutent, for example, a C$_{1-7}$ alkyl group, a C$_{3-20}$ heterocyclyl group, or a C$_{5-20}$ aryl group, preferably a C$_{1-7}$ alkyl group. Examples of sulfonamino groups include, but are not limited to, —NHS(=O)$_2$CH$_3$ and —N(CH$_3$)S(=O)$_2$C$_6$H$_5$.

Sulfinamino: —NR$^1$S(=O)R, wherein R$^1$ is an amino substitutent, as defined for amino groups, and R is a sulfinamino substitutent, for example, a C$_{1-7}$ alkyl group, a C$_{3-20}$ heterocyclyl group, or a C$_{5-20}$ aryl group, preferably a C$_{1-7}$ alkyl group. Examples of sulfinamino groups include, but are not limited to, —NHS(=O)CH$_3$ and —N(CH$_3$)S(=O)C$_6$H$_5$.

Phosphino (phosphine): —PR$_2$, wherein R is a phosphino substitutent, for example, —H, a C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphino groups include, but are not limited to, —PH$_2$, —P(CH$_3$)$_2$, —P(CH$_2$CH$_3$)$_2$, —P(t-Bu)$_2$, and —P(Ph)$_2$.

Phospho: —P(=O)$_2$.

Phosphinyl (phosphine oxide): —P(=O)R$_2$, wherein R is a phosphinyl substitutent, for example, a C$_{1-7}$ alkyl group, a C$_{3-20}$ heterocyclyl group, or a C$_{5-20}$ aryl group, preferably a C$_{1-7}$ alkyl group or a C$_{5-20}$ aryl group. Examples of phosphinyl groups include, but are not limited to, —P(=O)(CH$_3$)$_2$, —P(=O) (CH$_2$CH$_3$)$_2$, —P(=O)(t-Bu)$_2$, and —P(=O)(Ph)$_2$.

Phosphonic acid (phosphono): —P(=O)(OH)$_2$.

Phosphonate (phosphono ester): —P(=O)(OR)$_2$, where R is a phosphonate substitutent, for example, —H, a C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphonate groups include, but are not limited to, —P(=O)(OCH$_3$)$_2$, —P(=O)(OCH$_2$CH$_3$)$_2$, —P(=O)(O-t-Bu)$_2$, and —P(=O)(OPh)$_2$.

Phosphoric acid (phosphonooxy): —OP(=O)(OH)$_2$.

Phosphate (phosphonooxy ester): —OP(=O)(OR)$_2$, where R is a phosphate substitutent, for example, —H, a C$_{1-7}$ alkyl group, a C$_{3-20}$ heterocyclyl group, or a C$_{5-20}$ aryl group preferably —H, a C$_{1-7}$ alkyl group, or a C$_{5-20}$ aryl group. Examples of phosphate groups include, but are not limited to, —OP(=O)(OCH$_3$)$_2$, —OP(=O)(OCH$_2$CH$_3$)$_2$, —OP(=O)(O-t-Bu)$_2$, and —OP(=O)(OPh)$_2$.

Phosphorous acid: —OP(OH)$_2$.

Phosphite: —OP(OR)$_2$, where R is a phosphite substitutent, for example, —H, a C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group.

Examples of phosphite groups include, but are not limited to, —OP(OCH$_3$)$_2$, —OP(OCH$_2$CH$_3$)$_2$, —OP(O-t-Bu)$_2$, and —OP(OPh)$_2$.

Phosphoramidite: —OP(OR$^1$)—NR$^2$$_2$, where R$^1$ and R$^2$ are phosphoramidite substitutents, for example, —H, a (optionally substituted) C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphoramidite groups include, but are not limited to, —OP(OCH$_2$CH$_3$)—N(CH$_3$)$_2$, —OP(OCH$_2$CH$_3$)—N (i-Pr)$_2$, and —OP(OCH$_2$CH$_2$CN)—N (i-Pr)$_2$.

Phosphoramidate: —OP(=O)(OR$^1$)—NR$^2$$_2$, where R$^1$ and R$^2$ are phosphoramidate substitutents, for example, —H, a (optionally substituted) C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphoramidate groups include, but are not limited to, —OP(=O)(OCH$_2$CH$_3$)—N(CH$_3$)$_2$, —OP(=O)(OCH$_2$CH$_3$)—N(i-Pr)$_2$, and —OP(=O)(OCH$_2$CH$_2$CN)—N (i-Pr)$_2$.

Alkylene

C$_{3-12}$ alkylene: The term "C$_{3-12}$ alkylene", as used herein, pertains to a bidentate moiety obtained by removing two hydrogen atoms, either both from the same carbon atom, or one from each of two different carbon atoms, of a hydrocarbon compound having from 3 to 12 carbon atoms (unless otherwise specified), which may be aliphatic or alicyclic, and which may be saturated, partially unsaturated, or fully unsaturated. Thus, the term "alkylene" includes the sub-classes alkenylene, alkynylene, cycloalkylene, etc., discussed below.

Examples of linear saturated C$_{3-12}$ alkylene groups include, but are not limited to, —(CH$_2$)$_n$— where n is an integer from 3 to 12, for example, —CH$_2$CH$_2$CH$_2$— (propylene), —CH$_2$CH$_2$CH$_2$CH$_2$— (butylene), —CH$_2$CH$_2$CH$_2$CH$_2$CH$_2$— (pentylene) and —CH$_2$CH$_2$CH$_2$CH$_2$CH$_2$CH$_2$CH$_2$— (heptylene).

Examples of branched saturated C$_{3-12}$ alkylene groups include, but are not limited to, —CH(CH$_3$)CH$_2$—, —CH(CH$_3$)CH$_2$CH$_2$—, —CH(CH$_3$)CH$_2$CH$_2$CH$_2$—, —CH$_2$CH(CH$_3$)CH$_2$—, —CH$_2$CH(CH$_3$)CH$_2$CH$_2$—, —CH(CH$_2$CH$_3$)—, —CH(CH$_2$CH$_3$)CH$_2$—, and —CH$_2$CH(CH$_2$CH$_3$)CH$_2$—.

Examples of linear partially unsaturated C$_{3-12}$ alkylene groups (C$_{3-12}$ alkenylene, and alkynylene groups) include, but are not limited to, —CH=CH—CH$_2$—, —CH$_2$—CH=CH$_2$—, —CH=CH—CH$_2$—CH$_2$—, —CH=CH—CH$_2$—CH$_2$—CH$_2$—, —CH=CH—CH=CH—, —CH=CH—CH=CH—CH$_2$—, —CH=CH—CH=CH—CH$_2$—CH$_2$—, —CH=CH—CH$_2$—CH=CH—, —CH=CH—CH$_2$—CH$_2$—CH=CH—, and —CH$_2$—C≡C—CH$_2$—.

Examples of branched partially unsaturated C$_{3-12}$ alkylene groups (C$_{3-12}$ alkenylene and alkynylene groups) include, but are not limited to, —C(CH$_3$)=CH—, —C(CH$_3$)=CH—CH$_2$—, —CH=CH—CH(CH$_3$)— and —C≡C—CH(CH$_3$)—.

Examples of alicyclic saturated C$_{3-12}$ alkylene groups (C$_{3-12}$ cycloalkylenes) include, but are not limited to, cyclopentylene (e.g. cyclopent-1,3-ylene), and cyclohexylene (e.g. cyclohex-1,4-ylene).

Examples of alicyclic partially unsaturated C$_{3-12}$ alkylene groups (C$_{3-12}$ cycloalkylenes) include, but are not limited to, cyclopentenylene (e.g. 4-cyclopenten-1,3-ylene), cyclohexenylene (e.g. 2-cyclohexen-1,4-ylene; 3-cyclohexen-1,2-ylene; 2,5-cyclohexadien-1,4-ylene).

Proliferative Diseases

One of ordinary skill in the art is readily able to determine whether or not a candidate compound treats a proliferative condition for any particular cell type. For example, assays which may conveniently be used to assess the activity offered by a particular compound are described in the examples below.

The term "proliferative disease" pertains to an unwanted or uncontrolled cellular proliferation of excessive or abnormal cells which is undesired, such as, neoplastic or hyperplastic growth, whether in vitro or in vivo.

Examples of proliferative conditions include, but are not limited to, benign, pre-malignant, and malignant cellular proliferation, including but not limited to, neoplasms and tumours (e.g. histocytoma, glioma, astrocyoma, osteoma), cancers (e.g. lung cancer, small cell lung cancer, gastrointestinal cancer, bowel cancer, colon cancer, breast carinoma, ovarian carcinoma, prostate cancer, testicular cancer, liver cancer, kidney cancer, bladder cancer, pancreas cancer, brain cancer, sarcoma, osteosarcoma, Kaposi's sarcoma, melanoma), leukemias, psoriasis, bone diseases, fibroproliferative disorders (e.g. of connective tissues), and atherosclerosis.

Any type of cell may be treated, including but not limited to, lung, gastrointestinal (including, e.g. bowel, colon), breast (mammary), ovarian, prostate, liver (hepatic), kidney (renal), bladder, pancreas, brain, and skin.

Methods of Treatment

As described above, the present invention provide the use of a compound of formula IIIa or IIIb in a method of therapy. Also provided is a method of treatment, comprising administering to a subject in need of treatment a therapeutically-effective amount of a compound of formula IIIa or IIIb, preferably in the form of a pharmaceutical composition, which is the third aspect of the present invention. The term "therapeutically effective amount" is an amount sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage, is within the responsibility of general practitioners and other medical doctors.

A compound may be administered alone or in combination with other treatments, either simultaneously or sequentially dependent upon the condition to be treated. Examples of treatments and therapies include, but are not limited to, chemotherapy (the administration of active agents, including, e.g. drugs; surgery; and radiation therapy. If the compound of formula IIIa or IIIb bears a carbamate-based nitrogen protecting group which may be removed in vivo, then the methods of treatment described in WO 00/12507 (ADEPT, GDEPT and PDT) may be used.

Pharmaceutical compositions according to the present invention, and for use in accordance with the present invention, may comprise, in addition to the active ingredient, i.e. a compound of formula IIIa or IIIb, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous, or intravenous.

Pharmaceutical compositions for oral administration may be in tablet, capsule, powder or liquid form. A tablet may comprise a solid carrier or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. A capsule may comprise a solid carrier such a gelatin.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Includes Other Forms

Unless otherwise specified, included in the above are the well known ionic, salt, solvate, and protected forms of these substitutents. For example, a reference to carboxylic acid (—COOH) also includes the anionic (carboxylate) form (—COO$^-$), a salt or solvate thereof, as well as conventional protected forms. Similarly, a reference to an amino group includes the protonated form (—N$^+$HR$^1$R$^2$), a salt or solvate of the amino group, for example, a hydrochloride salt, as well as conventional protected forms of an amino group. Similarly, a reference to a hydroxyl group also includes the anionic form (—O$^-$), a salt or solvate thereof, as well as conventional protected forms.

Isomers, Salts and Solvates

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R—, S—, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Preferably compounds of the present invention have the following stereochemistry at the C11 position:

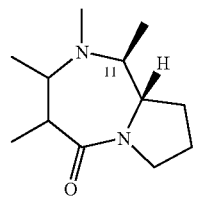

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g. C$_{1-7}$ alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hydroxyazo, and nitro/aci-nitro.

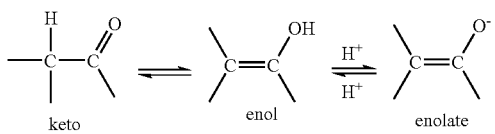

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; and the like.

Unless otherwise specified, a reference to a particular compound includes all such isomeric forms, including (wholly or partially) racemic and other mixtures thereof. Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

Unless otherwise specified, a reference to a particular compound also includes ionic, salt, solvate, and protected forms of thereof, for example, as discussed below.

It may be convenient or desirable to prepare, purify, and/or handle a corresponding salt of the active compound, for example, a pharmaceutically-acceptable salt. Examples of pharmaceutically acceptable salts are discussed in Berge, et al., *J. Pharm. Sci.*, 66, 1-19 (1977).

For example, if the compound is anionic, or has a functional group which may be anionic (e.g. —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{+3}$. Examples of suitable organic cations include, but are not limited to, ammonium ion (i.e. NH$_4^+$) and substituted ammonium ions (e.g. NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g. —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylactic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

A particular salt form of interest can be formed from compounds of formula IIIa and IIIb, where R$^{10}$ and R$^{15}$ form an imine bond, by reacting said compound with a bisulphite salt to form a bisulphite derivative of the PBD. These compounds can be represented as:

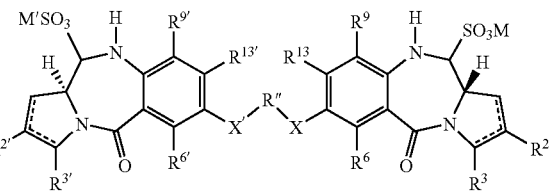

IVa

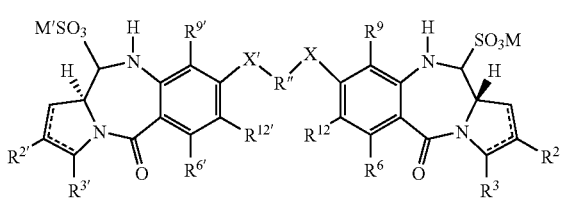

IVb where M and M' are independently monovalent pharmaceutically acceptable cations, or together form a divalent pharmaceutically acceptable cation, and the other groups are as previously defined.

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

Solvates of particular relevance to the present invention are those where the solvent adds across the imine bond of the PBD moiety, which is illustrated below where the solvent is water or an alcohol (R$^B$OH, where R$^B$ is an ether substitutent as described above):

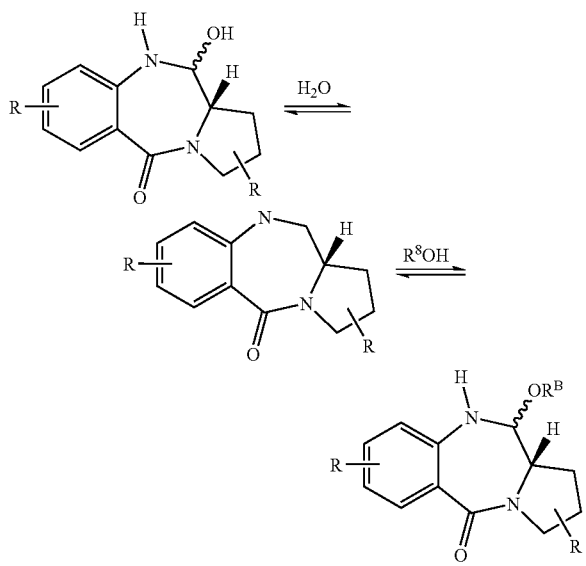

These forms can be called the carbinolamine and carbinolamine ether forms of the PBD. The balance of these equilibria depend on the conditions in which the compounds are found, as well as the nature of the moiety itself.

In general any nucleophilic solvent is capable of forming such solvates as illustrated above for hydroxylic solvents. Other nucleophilic solvents include thiols and amines.

These solvates may be isolated in solid form, for example, by lyophilisation.

General Synthetic Routes

The synthesis of PBD compounds is extensively discussed in WO 00/12508, which discussion is incorporated herein by reference.

As discussed in that patent application, a key step in a preferred route to PBDs is a cyclisation to produce the B-ring, involving generation of an aldehyde (or functional equivalent thereof) at what will be the 11-position, and attack thereon by the Pro-N10-nitrogen:

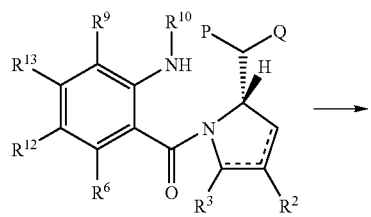

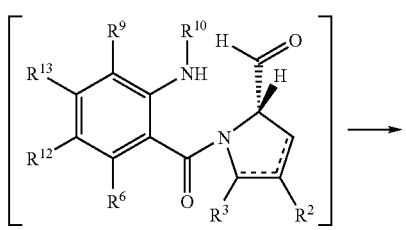

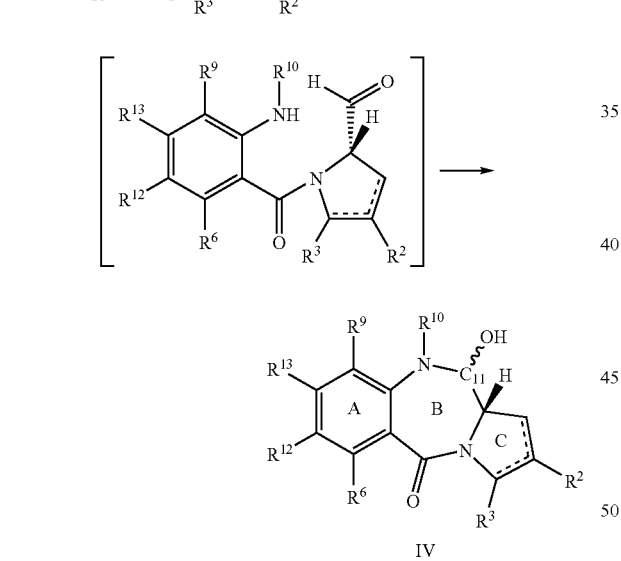

wherein the substitutents are as defined in the second aspect of the invention and $R^{12}$ and $R^{13}$ are either $OR^{14}$ and $R^4$ respectively or $R^4$ and $OR^{14}$ repectively i.e. the protected hydroxyl group may be at either the C7 or C8 position with the other position being $R^4$. The "masked aldehyde" —CPQ may be an acetal or thioacetal, in which case the cyclisation involves unmasking. Alternatively, it may be an alcohol —CHOH, in which case the reaction involves oxidation, e.g. by means of TPAP, TEMPO or DMSO (Swern oxidation).

The masked aldehyde compound can be produced by condensing a corresponding 2,4-substituted pyrrolidine with a 2-nitrobenzoic acid:

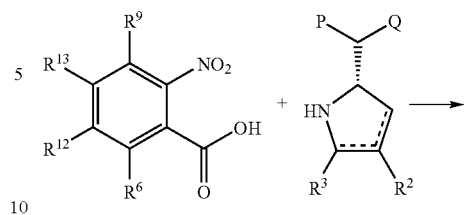

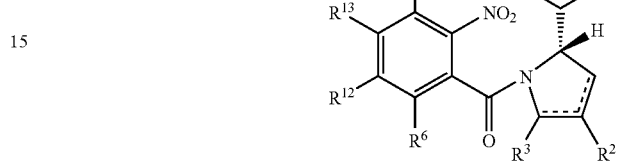

The nitro group can then be reduced to —$NH_2$ and protected by reaction with a suitable agent, e.g. a chloroformate, which provides the removable nitrogen protecting group in the compound of formula IV.

A process involving the oxidation-cyclization procedure is illustrated in scheme 1 (an alternative type of cyclisation will be described later with reference to scheme 2).

Scheme 1

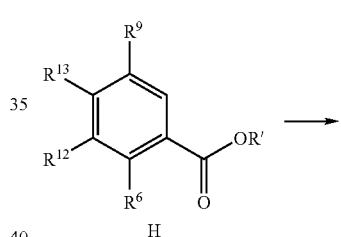

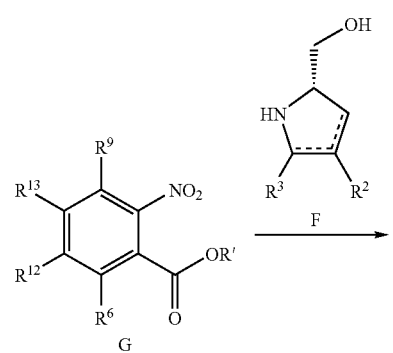

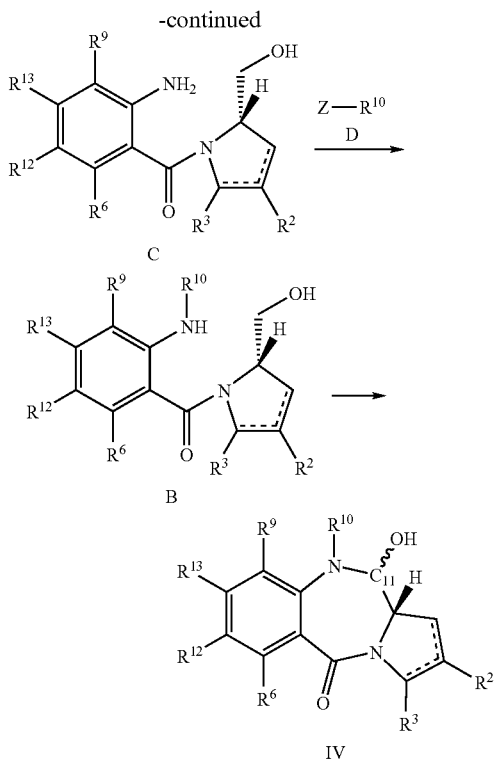

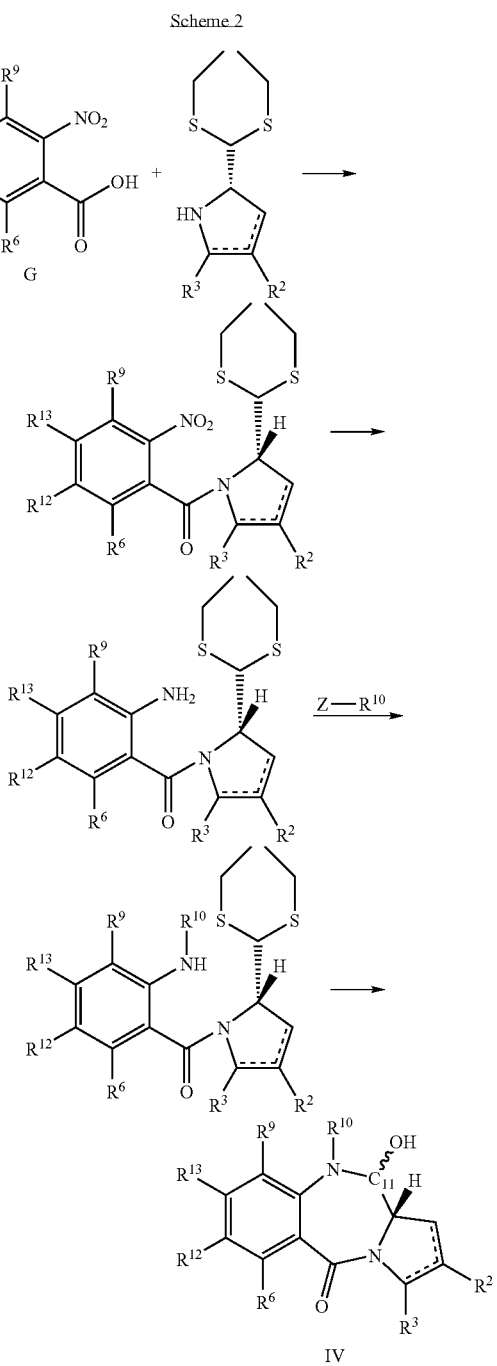

Exposure of the alcohol (B) (in which the Pro-N10-nitrogen is generally protected as carbamate) to tetrapropylammonium perruthenate (TPAP)/N-methylmorpholine N-oxide (NMO) over A4 sieves results in oxidation accompanied by spontaneous B-ring closure to afford the desired product IV. The TPAP/NMO oxidation procedure is found to be particularly convenient for small scale reactions while the use of DMSO-based oxidation methods, particularly Swern oxidation, proves superior for larger scale work (e.g. >1 g). A particularly preferred oxidising agent is (diacetoxyiodo)benzene (1.1 eq) and TEMPO (0.1 eq) dissolved in $CH_2Cl_2$.

The uncyclized alcohol (B) may be prepared by the reaction of a nitrogen protection reagent of formula D, which is preferably a chloroformate or acid chloride, to a solution of the amino alcohol C, generally in solution, generally in the presence of a base such as pyridine (preferably 2 equivalents) at a moderate temperature (e.g. at 0° C.). Under these conditions little or no O-acylation is usually observed.

The key amino alcohol C may be prepared by reduction of the corresponding nitro compound E, by choosing a method which will leave the rest of the molecule intact. Treatment of E with tin (II) chloride in a suitable solvent, e.g. refluxing methanol, generally affords, after the removal of the tin salts, the desired product in high yield.

Exposure of E to hydrazine/Raney nickel avoids the production of tin salts and may result in a higher yield of C, although this method is less compatible with the range of possible C and A-ring substitutents. For instance, if there is C-ring unsaturation (either in the ring itself, or in $R_2$ or $R_3$), this technique may be unsuitable.

The nitro compound of formula E may be prepared by coupling the appropriate o-nitrobenzoyl chloride to a compound of formula F, e.g. in the presence of $K_2CO_3$ at −25° C. under a $N_2$ atmosphere. Compounds of formula F can be readily prepared, for example by olefination of the ketone derived from L-trans-hydroxy proline. The ketone intermediate can also be exploited by conversion to the enol triflate for use in palladium mediated coupling reactions.

The o-nitrobenzoyl chloride is synthesised from the o-nitrobenzoic acid (or alkyl ester after hydrolysis) of formula G, which itself is prepared from the vanillic acid (or alkyl ester) derivative H. Many of these are commercially available and some are disclosed in Althuis, T. H. and Hess, H. J., *J. Medicinal Chem.*, 20(1), 146-266 (1977).

Alternative Cyclisation (Scheme 2)

In scheme 1, the final or penultimate step was an oxidative cyclisation. An alternative, using thioacetal coupling, is shown in scheme 2. Mercury-mediated unmasking causes cyclisation to the protected PBD compound IV.

The thioacetal compound may be prepared as shown in scheme 2: the thioacetal protected C-ring [prepared via a literature method: Langley, D. R. & Thurston, D. E., *J. Organic Chemistry*, 52, 91-97 (1987)] is coupled to the o-nitrobenzoic acid (or alkyl ester after hydrolysis) (G) using a literature procedure. The resulting nitro compound cannot be reduced by hydrogenation, because of the thioacetal group; so the tin(II) chloride method is used to afford the amine. This is then N-protected, e.g., by reaction with a chloroformate or acid chloride, such as 2,2,2-trichloroethylchloroformate.

Acetal-containing C-rings can be used as an alternative in this type of route with deprotection involving other methods, including the use of acidic conditions.

Alternative Routes to PBDs

Alternative methods of synthesising N10 protected PBDs are disclosed in co-pending application PCT/GB2004/003873 (filed 10 Sep. 2004) which claims priority from GB0321295.8 (filed 11 Sep. 2003), which describes the use of isocyanate intermediates.

Formation of Compounds IIIa and IIIb (Scheme 3)

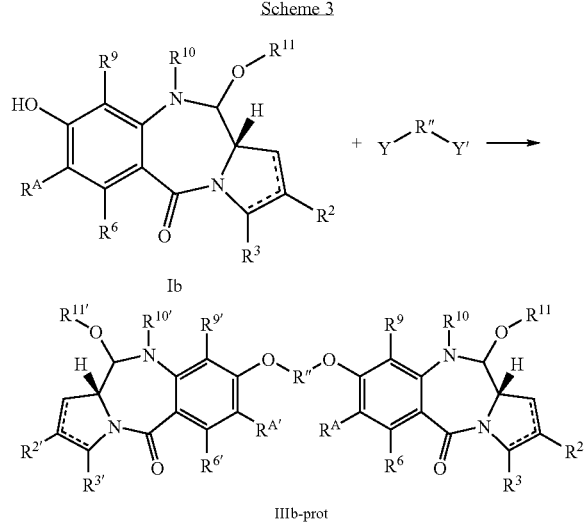

Formation of the protected compound IIIb dimer from compound Ib is illustrated, however, protected compound IIIa is formed in an analogous manner with compound Ia as the starting material.

The PBD dimer compound IIIa or IIIb may be synthesized by dimerisation of compounds of formula Ia or Ib respectively following deprotection of the OH group at either the C7 or C8 position. The synthesis route illustrated in scheme 3 shows compounds when the dimer linkage is of the formula —O—$(CH_2)_n$—O—.

The protected dimer IIIa or IIIb may be formed from compounds of formula Ia or Ib respectively through reaction with a disubstituted linking chain. The linking chain is preferably of the general form Y—R"—Y' where R" is as previously defined and Y and Y' are groups which can be reacted with an alcohol to form an ether linkage. Y and Y' are preferably independently selected from I, Br, Cl, OH, mesylate or tosylate. In a preferred aspect, Y and Y' are the same. In a preferred aspect Y and Y' are both iodo-groups.

Where Y and/or Y' is I, Br, Cl, mesylate or tosylate, the Y—R"—Y' reactant is coupled to the compound of formula Ia or Ib by a simple elimination reaction with Y and Y' as leaving groups. For example where the linking chain is —O—$CH_2$—$CH_2$—$CH_2$—O—, the compound of formula Ia or Ib is reacted with 1,3-diiodopropane in the presence of $K_2CO_3$. Generally, where the linking chain is a straight chain alkyl ether of the form —O—$(CH_2)_n$—O—, the compound of formula Ia or Ib is preferably reacted with the corresponding 1,n-diiodoalkane.

Where Y and/or Y' is OH, the Y—R"—Y' reactant is coupled to the compound of formula Ia or Ib under Mitsunobu conditions.

It is important that the OH protecting group at C11 in formula Ia or Ib is orthogonal to the OH protecting group at C7 and/or C8. This allows the C7 and/or C8 protection to be removed to give the free alcohol to allow dimerisation whilst the C11 OH group remains protected and therefore unreactive under the dimerisation conditions.

Following dimerisation, the imine bond in the compound of formula IIIb-prot can be deprotected by standard methods to yield the unprotected compound IIIb (which may be in its carbinolamine or carboinolamine ether form, depending on the solvents used). For example if $R^{10}$ is Alloc, then the deprotection is carried using palladium to remove the N10 protecting group, followed by the elimination of water. If $R^{10}$ is Troc, then the deprotection is carried out using a Cd/Pb couple to yield the compound of formula IIIb.

Compound IIIa may be formed in an analogous manner via deprotection of the protected imine.

If the nitrogen protecting group ($R^{10}$) is such that the desired end product still contains it, e.g. if it is removable in vivo, then the C11 deprotected forms of compounds of formula IIIa or IIIb may be synthesised by removal of the oxygen protecting groups under suitable conditions to leave the $R^{10}$ group in unaffected.

The above described methods are suited to the synthesis of dimers where both the PBD monomers have the same substitutent pattern. One method of synthesising a dimer where the substitutent pattern of the two PBD monomers is not the same involves protecting one end of the compound Y—R"—Y' (or using an already protected compound), coupling a PBD monomer to the unprotected end, deprotecting the other end and coupling a different PBD monomer to the free end. This route is shown in scheme 4.

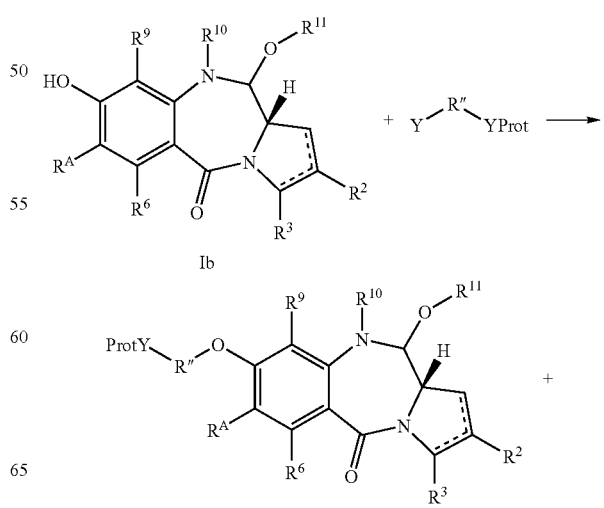

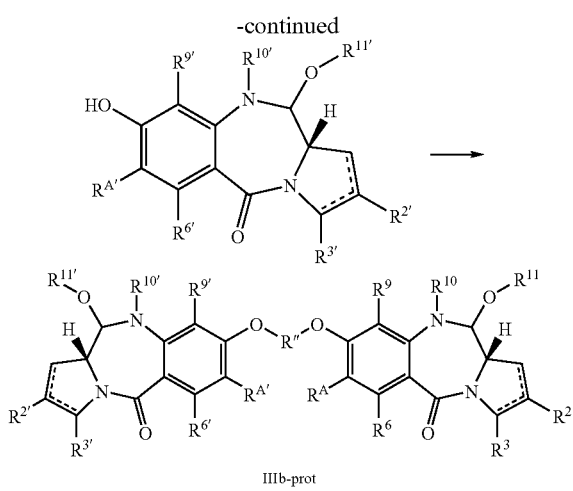

IIIb-prot

Where YProt, is a protected version, or precursor to Y'. If Y' is protected then the protecting group used should be orthogonal to those on the rest of the molecule, in particular, $R^{10}$ and $R^{11}$. One example of this route, would be to have Y as —OH and YProt as —O-benzyl. The first monomer could be joined by Mitsunobu coupling, the benzyl hydroxy deprotected, and then the free hydroxy coupled to the second monomer by a further Mitsunobu reaction.

Formation of Compound of Formula Ia or Ib

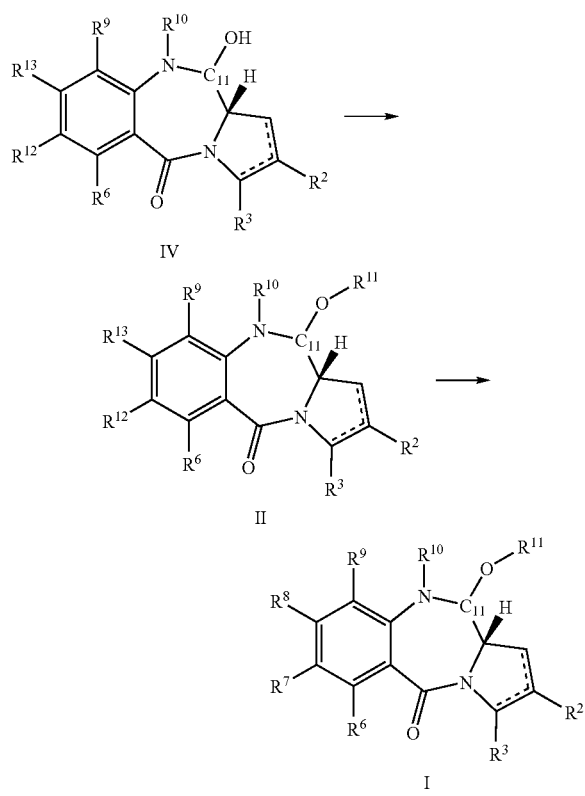

Following cyclisation to form the B-ring, the C11-alcohol IV is then preferably protected, by conventional means to provide II. For example, if $R^{11}$ is THP, the protection can take place by reacting IV with dihydropyran (DHP) and catalytic p-toluene sulfonic acid. Cleavage of the C7 or C8-protecting group from II then provides the corresponding C7 or C8 alcohol. For example, where the C7 or C8 protecting group ($R^{12}$ or $R^{13}$) is a benzyl ether, this deprotection may be performed by reaction with $H_2$ catalysed by palladium on carbon.

This protection at the C11 position and deprotection of the C7 or C8 alcohol allows subsequent reaction of selectively the C7 or C8 alcohol position, for example to form the dimer compound IIIa or IIIb leaving the C11 position unaffected.

Further Preferences

The following preferences may apply to all aspects of the invention as described above, or may relate to a single aspect. The preferences may be combined together in any combination.

$R^9$ is preferably H.

$R^2$ is preferably R, and is more preferably an optionally substituted $C_{5-20}$ aryl group. Most preferred is an optionally substituted phenyl group.

$R^6$ is preferably selected from H, OH, OR, SH, $NH_2$, nitro and halo, and is more preferably H or halo, and most preferably is H.

$R^4$ is preferably independently selected from H, OR, SH, SR, $NH_2$, NHR, NRR', and halo, and more preferably independently selected from H and OR, where R is preferably selected from optionally substituted $C_{1-7}$ alkyl, $C_{3-10}$ heterocyclyl and $C_{5-10}$ aryl groups.

In the first aspect of the invention, $R^{10}$ is preferably BOC or Troc. $R^{11}$ is preferably THP or a silyl oxygen protecting group (for example TBS) and $R^4$ is preferably selected from OMe and H. In a most preferred first aspect of the invention, $R^{10}$ is BOC, $R^{11}$ is THP and $R^4$ is OMe.

In the second aspect of the invention, at least one of $R^{14}$ is preferably a benzyl ether and $R^4$ is preferably OMe or H. $R^{11}$ is preferably THP or a silyl oxygen protecting group (for example TBS). Accordingly, in a particularly preferred embodiment of the second aspect of the invention $R^4$ is OMe and $R^{11}$ is THP or TBS. Furthermore, $R^{10}$ is preferably BOC.

In some embodiments of the third aspect of the invention, $R^{10}$ is preferably BOC and $R^{15}$ is O—$R^{11}$, wherein $R^{11}$ is preferably THP or a silyl oxygen protecting group (for example TBS).

In other embodiments of the third aspect of the invention, $R^{10}$ and $R^{15}$ together form a double bond between N10 and C11.

In some aspects of the third embodiment of the invention, the two PBD monomer units are linked at the C7 and C7' positions. In other aspects of the third embodiment of the invention, the two PBD monomer units are linked at the C8 and C8' positions.

In preferred aspects of the third embodiment of the invention, the substitutent groups on C7, C8, N10 and C11 are the same on each monomer unit that makes up the dimers of the third aspect of the invention. In is further preferred that the substitutent groups on all positions of each mononmer unit that make up the dimer are the same.

Novel compounds of the present invention preferably have $R^{10}$ and $R^{15}$ forming a double bond between N10 and C11. Preferably, the novel compounds of the invention are dimers through C7 or C8, i.e. the $R^7$ or $R^8$ groups of each monomer form together a dimer bridge having the formula —X—R"—X— linking the monomers. More preferably, the dimer bridge is of formula —O—$(CH_2)_n$—O—, where n is 3 to 12, more preferably for the dimers linked at the C8 position, n is 7 to 12, more preferably n is 7 to 11 and even more preferably n is 7, 9 or 11; for the dimer linked at the C7 position, n is preferably 3 to 12, more preferably 3, 5, or 7. The preferences for $R^6$, $R^7$ and $R^9$ are as expressed above. Preferably, $R^{12}$ and $R^{13}$ are independently selected from H, OH, OR, SH, $NH_2$, nitro and halo. More preferably $R^{12}$ and $R^{13}$ are independently selected from H, OH and OR. Most preferred is $R^{12}$ and $R^{13}$ as OMe.

If R is optionally substituted $C_{1-12}$ alkyl, it is preferred that it is optionally substituted $C_{1-7}$ alkyl.

EXAMPLE 1

Synthesis of PBD Monomer-(11S,11aS)-10-(tert-Butyloxycarbonyl)-7-hydroxy-8-methoxy-11-(tetrahydroxy-pyran-2-yloxy)-1,2,3,10,11,11a-hexahydro-5H-pyrrolo[2,1-c][1,4]benzodiazepine-5-one (7)

(a) (5-Benzyloxy-4-methoxy-2-nitrobenzoyl)-pyrrolidine-2-methanol (2)

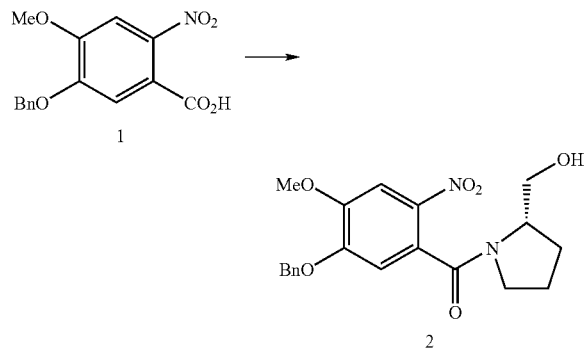

1-(3-dimethylaminopropyl)-3-ethylcarbodiimide (EDCI) (6.33 g, 33.0 mmol, 1.0 equiv) was added to a stirred solution of the acid 1 (10 g, 33.0 mol, 1.0 equiv) in anhydrous DCM (300 mL) under a nitrogen atmosphere at 0° C. After stirring for 10 minutes the mixture was treated with HOBt (4.46 g, 33.0 mmol, 1.0 equiv) and few drops of DMF and the resulting mixture was allowed to warm to room temperature and stirred for 2 h. The mixture was again cooled down to 0° C. and treated with dropwise with a solution of pyrrolidinemethanol (5 g, 49.50 mmol, 1.5 equiv) in anhydrous DCM (100 mL). When the reaction mixture was complete, as indicated by TLC (EtOAc), the reaction mixture was diluted with DCM, washed with 1N HCl (100 mL), saturated $NaHCO_3$ (100 mL), brine (100 mL), dried ($MgSO_4$), filtered and evaporated in vacuo. The title compound was isolated by flash column chromatography ($SiO_2$, 50% EtOAc-hexane) to afford the coupled compound 2 (10 g, 25.7 mol, 78%) as a brown oil: $[\alpha]^{20}{}_D=-77°$ (c=0.22, $CHCl_3$); $^1H$ NMR ($CDCl_3$, 400 MHz): δ 1.65-1.92 (m, 3H, 1-H, 2-H), 2.10-2.22 (m, 1H, 1-H), 2.96-3.08 (m, 2H, 3-H), 3.62-3.90 (m, 2H, 11-H), 3.98 (s, 3H, 7-OMe), 4.29-4.45 (m, 2H, 11a-H, OH), 5.24 (s, 2H, OBn), 6.81 (s, 1H, 6-H), 7.31-7.47 (m, 5H, Ph), 7.72 (s, 1H, 9H); $^{13}C$ NMR ($CDCl_3$, 400 MHz): δ 24.3, 28.4, 49.4, 56.5, 61.4, 66.0, 71.4, 101.4, 110.9, 127.0, 127.1, 127.4, 128.3, 128.5, 128.81, 128.87, 135.0, 137.3, 149.6, 153.4; IR (neat): 3391, 2971, 2888, 1620, 1576, 1523, 1441, 1336, 1277, 1222, 1061 $cm^{-1}$; MS (FAB) m/z (relative intensity) 409 ([M+Na]$^+$, 58), 387 ($M^+$, 100), 285 (13).

(b) (2-Amino-5-benzyloxy-4-methoxybenzoyl)-pyrrolidine-2-methanol (3)

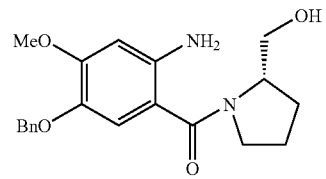

A solution of the nitro compound 2 (15.49 g, 40.12 mmol, 1.0 equiv) and tin (II) chloride (45.27 g, 200.64 mol, 5.0 equiv) in methanol (300 mL) was heated at reflux for 4 h. Excess solvent was removed by rotary evaporation under reduced pressure. The residue was treated carefully with a saturated aqueous sodium bicarbonate solution to basify the mixture to pH 9. The resulting suspension was allowed to stir overnight with ethyl acetate (100 mL), and filtrated through Celite to remove precipitated tin salts. The aqueous phase was extracted with EtOAc (2×50 mL), and the combined organic phase washed with brine (50 mL), dried ($MgSO_4$), and evaporated in vavuo to provide 3 as a pink oil, which was used in the subsequent reaction without further purification: $[\alpha]^{20}{}_D=-97°$ (c=0.18, $CHCl_3$); $^1H$ NMR ($CDCl_3$, 400 MHz): δ 1.50-1.81 (m, 3H, 1-H, 2-H), 2.05-2.15 (m, 1H, 1-H), 3.03-3.16 (m, 1H, 3-H), 3.23-3.36 (m, 1H, 3-H), 3.56-3.78 (m, 2H, 11-H), 3.88 (s, 3H, 7-OMe), 4.21-4.38 (m, 1H, 11a-H), 4.47-4.75 (m, 1H, 3-H), 5.03 (d, 1H, J=12.4 Hz, OBn), 5.10 (d, 1H, J=12.4 Hz, OBn), 6.26 (s, 1H, 9-H), 6.66 (s, 1H, 6-H), 7.28-7.41 (m, 5H, Ph); $^{13}C$ NMR ($CDCl_3$, 400 MHz): δ 24.8, 28.5, 51.1, 55.7, 61.1, 67.5, 72.5, 100.8, 116.9, 127.5, 127.7, 128.4, 137.4, 138.8, 142.6, 153.0, 171.1, 171.7; IR (neat): 3436, 33.52, 29.67, 28.73, 1621, 1589, 1513, 1448, 1402, 1264, 1216, 1172, 1110, 1025 $cm^{-1}$; MS (FAB) m/z (relative intensity) 379 ([M+Na]$^+$, 5), 357 ($M^+$, 100), 255 (58).

(c) N-[5-Benzyloxy-2-(tert-butyloxycarbonylamino)-4-methoxybenzoyl]-pyrrolidine-2-methanol (4)

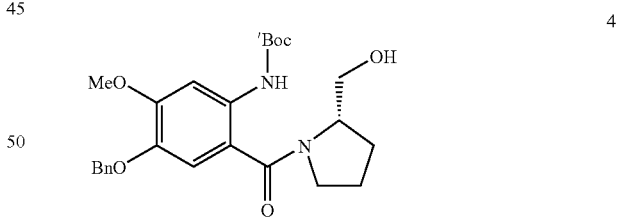

A solution of amine 3 (8 g, 22.47 mmol, 1.0 equiv) and Di-tert-butyl dicarbonate (7.35 g, 33.70 mmol, 1.5 equiv) in THF (150 mL) was heated at reflux overnight. The reaction mixture was allowed to cool to RT and excess THF was removed under reduced pressure to give the crude product. The residue was subjected to flash column chromatography ($SiO_2$, 30% EtOAc-hexane) to afford the product 4 (6.2 g, 13.59 mmol, 60%) as yellow oil: $[\alpha]^{20}{}_D=-106°$ (c=0.198, $CHCl_3$); $^1H$ NMR ($CDCl_3$, 400 MHz): δ 1.47 (s, 9H, Boc), 1.50-1.77 (m, 3H, 1-H, 2-H), 2.03-2.15 (m, 1H, 1-H), 2.83-3.00 (m, 1H, 3-H), 3.09-3.24 (m, 1H, 3-H), 3.56-3.84 (m, 2H, 11-H), 3.90 (s, 3H, 7-OMe), 4.21-4.43 (m, 2H, 11a-H, OH), 5.07 (d, 1H, J=13 Hz, OBn), 5.19 (d, 1H, J=13 Hz, OBn), 6.68

(s, 1H, 6-H), 7.26-7.38 (m, 5H, Ph), 7.85 (s, 1H, 9-H), 8.60 (s, 1H, NH); $^{13}$C NMR (CDCl$_3$, 400 MHz): δ 21.0, 28.33, 28.36, 51.1, 56.0, 61.1, 66.8, 71.6, 80.3, 104.4, 127.2, 127.8, 128.5, 133.5, 137.1, 141.4, 152.1, 153.1, 171.6; IR (neat): 3350, 2975, 1721, 1596, 1520, 1453, 1395, 1240, 1158, 1113, 1049 cm$^{-1}$; MS (FAB) m/z (relative intensity) 479 ([M+Na]$^+$, 40), 457 (M$^+$, 100), 357 (51).

(d) (11S,11aS)-7-Benzyloxy-10-(tert-butyloxycarbonyl)-11-hydroxy-8-methoxy-1,2,3,10,11,11a-hexahydro-5H-pyrrolo[2,1-c][1,4]benzodiazepine-5-one (5)

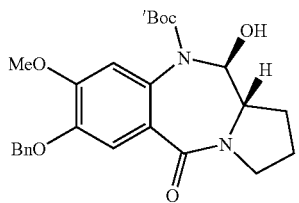

To a solution of Boc protected amine alcohol 4 (6.2 g, 13.59 mmol, 1.0 equiv) in DCM (50 mL), BAIB (4.82 g, 14.95 mmol, 1.1 equiv) and TEMPO (0.21 g, 1.35 mmol, 0.1 equiv) were added and the mixture was stirred overnight. When the reaction was complete as indicated by TLC (SiO$_2$, 50% EtOAc-hexane), the reaction mixture was diluted with DCM (100 mL) and washed with saturated Na$_2$S$_2$O$_3$ (60 mL). The aqueous layer was extracted with DCM (2×50 mL) and the combined organic layer washed with brine (50 mL) and dried (MgSO$_4$). Removal of excess solvent under reduced pressure afforded a crude solid which washed with cold EtOAc to give cyclized PBD 5 (4.9 g, 10.8 mmol, 79%) as white solid: $[\alpha]^{20}_D$=+146° (c=0.178, CHCl$_3$); $^1$H NMR (CDCl$_3$, 400 MHz): δ 1.40 (s, 9H, Boc),1.93-2.18 (m, 4H, 1-H, 2-H), 3.42-3.50 (m, 1H, 11a-H), 3.51-3.61 (m, 1H, 3-H), 3.56-3.79 (m, 2H, 3-H, OH), 3.87 (s, 3H, 7-OMe), 5.13 (d, 1H, J=12 Hz, OBn), 5.20 (d, 1H, J=12 Hz, OBn), 5.51-5.62 (m, 1H, 11-H), 6.63 (s, 1H, 9-H), 7.29-7.41 (m, 4H, 6-H, Ph), 7.43-7.48 (m, 2H, Ph); $^{13}$C NMR (CDCl$_3$, 400 MHz): δ 23.0, 28.2, 28.7, 46.3, 56.1, 59.6, 70.9, 76.7, 77.0, 77.3, 81.7, 85.7, 112.3, 112.9, 125.4, 127.5, 128.0, 128.5, 129.6, 136.4, 147.2, 151.0, 159.0, 166.9; IR (neat): 3372, 2977, 2879, 1698, 1622, 1514, 1450, 1393, 1368, 1326, 1279, 1215, 1162, 1135, 1103, 1052, 1025 cm$^{-1}$; MS (FAB) m/z (relative intensity) 477 ([M+Na]$^+$, 35), 455 (M$^+$, 100), 399 (85), 337 (20).

(e) (11S,11aS)-7-Benzyloxy-10-(tert-butyloxycarbonyl)-8-methoxy-11-(tetrahydroxy-pyran-2-yloxy)-1,2,3,10,11,11a-hexahydro-5H-pyrrolo[2,1-c][1,4]benzodiazepine-5-one (6)

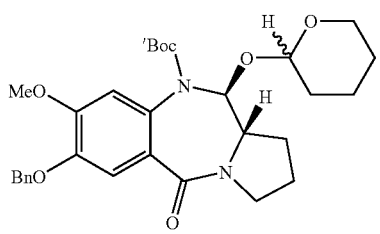

A catalytic amount of PTSA was added to a solution of DHP (2.87 g, 34.14 mmol, 5.0 equiv) in EtOAc (10 mL) at 0° C. After stirring 10 minutes, the cyclized compound 5 (3.1 g, 6.8 mmol, 1.0 equiv) was added portion-wise to the mixture and the resulting mixture was stirred until starting material disappearance by TLC (SiO$_2$, 50% EtOAc-hexane). The mixture was diluted with EtOAc (100 mL), washed with saturated NaHCO$_3$ (30 mL), brine (30 mL) and dried (MgSO$_4$). Removal of excess solvent afforded the protected compound 6 (3.5 g, 6.5 mmol, 95% yield, mixture of diastereomers from THP protecting group), which was used in the subsequent reaction without further purification: $[\alpha]^{20}_D$=+33° (c=0.21, CHCl$_3$); $^1$H NMR (CDCl$_3$, 400 MHz): δ 1.36 (s, 18H, Boc), 1.47-1.92 (m, 12H, THP), 1.93-2.20 (m, 8H, 1-H, 2-H), 3.41-3.75 (m, 8H, 3-H, 11a-H, THP), 3.84-4.09 (m, 8H, 7-OMe, THP), 4.82-5.28 (m, 6H, OBn, THP), 5.69-5.79 (d, 1H, 11-H), 5.80-5.91 (d, 1H, 11-H), 6.54 (s, 1H, 9-H), 6.91 (s, 1H, 9-H), 7.27-7.47 (m, 12H, 6-H, Ph); $^{13}$C NMR (CDCl$_3$, 400 MHz): δ 19.8, 23.2, 25.31, 25.34, 25.4, 28.1, 28.2, 28.8, 29.1, 30.7, 30.9, 46.2, 55.9, 56.2, 60.0, 60.1, 63.3, 63.4, 70.94, 70.98, 81.0, 81.3, 88.2, 91.2, 98.4, 100.3, 112.0, 112.1, 113.6, 114.2, 126.4, 127.50, 127.54, 127.9, 128.0, 128.56, 128.58, 130.2, 136.5, 136.6, 147.4, 147.7, 151.0, 151.4, 159.0, 159.5, 167.2, 167.4; IR (neat): 3410, 2944, 2873, 1703, 1645, 1604, 1513, 1448, 1393, 1326, 1271, 1216, 1163, 1022 cm$^{-1}$; MS (FAB) m/z (relative intensity) 561 ([M+Na]$^+$, 5), 539 (M$^+$, 100), 337 (82), 483 (24).

(f) (11S,11aS)-10-(tert-Butyloxycarbonyl)-7-hydroxy-8-methoxy-11-(tetrahydroxy-pyran-2-yloxy)-1,2,3,10,11,11a-hexahydro-5H-pyrrolo[2,1-c][1,4]benzodiazepine-5-one (7)

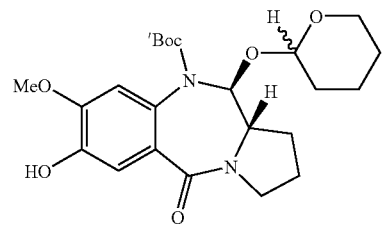

A catalytic amount of 10% palladium on carbon (380 mg) was added to a solution of THP protected compound 6 (3.8 g, 7 mmol) in absolute alcohol (30 mL). The reaction mixture was hydrogenated for 3 h at 35 Psi. When the reaction was complete as indicated by TLC (SiO$_2$, 50% EtOAc-hexane) the reaction mixture was filtered through Celite, and removal of excess solvent under reduced pressure afforded the phenol 7 (2.8 g, 6.25 mmol, 90% yield, mixture of diastereomers from THP protecting group) as a white solid: $[\alpha]^{20}_D$=+52° (c=0.183, CHCl$_3$); $^1$H NMR (CDCl$_3$, 400 MHz): δ 1.35 (s, 18H, Boc), 1.48-1.68 (m, 6H, THP), 1.69-1.88 (m, 6H, THP), 1.91-2.18 (m, 8H, 1-H, 2-H), 3.44-3.75 (m, 8H, 3-H, 11a-H, THP), 3.84-4.02 (m, 8H, 7-OMe, THP), 4.96-5.09 (m, 1H, THP), 5.10-5.18 (m, 1H, THP), 5.69-5.76 (d, 1H, 11-H), 5.77-5.87 (d, 1H, 11-H), 6.03 (s, 1H, OH), 6.14 (s, 1H, OH), 6.49 (s, 1H, 9-H), 6.86 (s, 1H, 9-H), 7.28 (s, 1H, 6-H), 7.32 (s, 1H, 6-H); $^{13}$C NMR (CDCl$_3$, 400 MHz): δ 19.8, 20.5, 23.1, 23.2, 25.2, 25.3, 28.1, 28.2, 28.8, 29.1, 30.8, 31.2, 46.2, 55.9, 56.1, 59.9, 60.1, 63.3, 64.6, 80.9, 88.1, 91.1, 95.2, 100.4, 112.6, 113.3, 113.6, 114.2, 127.1, 129.0, 145.0, 145.3, 148.1, 148.5, 155.1, 167.1, 167.3; IR (neat): 3306, 2946, 1703, 1632, 1511, 1453, 1394, 1368, 1334, 1274, 1212, 1163, 1116, 1023 cm$^{-1}$; MS (FAB) m/z (relative intensity) 471 ([M+Na]$^+$, 5), 449 (M$^+$, 100), 246 (50), 393 (22).

EXAMPLES 2-11

Formation of PBD Dimmers Linked at the C-7 Position (9)

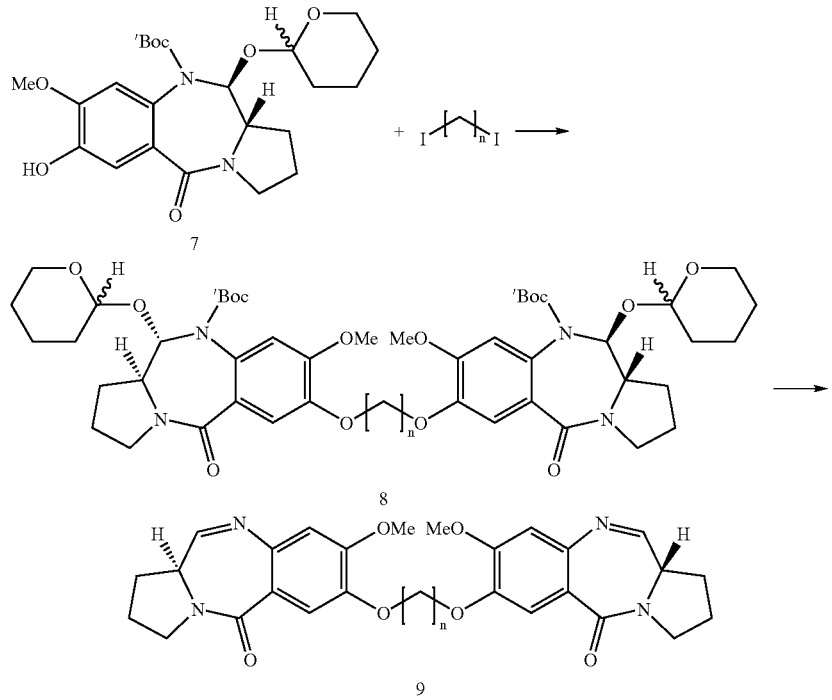

n = 3, 4, 5, 6, 7, 8, 9, 10, 11, 12

EXAMPLE 2 (n=3)

(a) 1,1'-[(Propane-1,3-diyl)dioxy]bis[(11S,11aS)-10-(tert-butyloxycarbonyl)-8-methoxy-11-(tetrahydro-pyran-2-yloxy)-1,2,3,10,11,11a-hexahydro-5H-pyrrolo[2,1-c][1,4]benzodiazepine-5-one] (8a)

Diiodopropane (0.1 g, 0.22 mmol, 0.5 equiv) was added to the mixture of monomer 7 (0.2 g, 0.44 mmol, 1.0 equiv) and potassium carbonate (0.98 mmol, 2.2 equiv) in dry DMF (30 mL), and the resulting mixture was heated to 90° C. under a nitrogen atmosphere for 5 hours. Removal of excess solvent under reduced pressure afforded a crude solid, which was subjected to flash column chromatography (SiO$_2$, 50% EtOAc-hexane) to afford the dimerized compound 8a (80 mg, 0.08 mmol, 38% yield, mixture of diastereomers from THP protecting group as a solid: [α]$^{20}_D$=+31° (c=0.16, CHCl$_3$); $^1$H NMR (CDCl$_3$, 400 MHz): δ 1.35 (s, 36H, Boc), 1.44-1.67 (m, 16H, THP), 1.68-1.86 (m, 8H, THP), 1.91-2.20 (m, 16H, 1-H, 2-H), 2.35-2.44 (m, 4H, 13-H), 3.42-3.75 (m, 16H, 3-H, 11a-H, THP), 3.84-4.02 (m, 16H, 7-OMe, THP), 4.19-4.38 (m, 8H, 12-H), 5.01-5.10 (m, 2H, THP), 5.11-5.20 (m, 2H, THP), 5.69-5.77 (d, 2H, 11-H), 5.79-5.89 (d, 2H, 11-H), 6.50 (s, 2H, 9-H), 6.88 (s, 2H, 9-H), 7.22 (s, 2H, 6-H), 7.26 (s, 2H, 6-H); $^{13}$C NMR (CDCl$_3$, 400 MHz): δ 19.8, 20.5, 23.1, 23.2, 25.3, 28.1, 28.2, 28.8, 29.0, 29.1, 30.9, 31.2, 46.3, 55.9, 56.1, 60.0, 60.1, 63.3, 64.5, 65.4, 81.0, 88.1, 91.2, 95.9, 100.2, 111.5, 113.5, 114.1, 129.9, 139.6, 144.5, 147.3, 147.8, 155.9, 167.4, 167.6; IR (neat): 3306, 2945, 1704, 1643, 1605, 1513, 1450, 1393, 1327, 1217, 1164, 1022 cm$^{-1}$; MS (FAB) m/z (relative intensity) 937 (M$^+$, 100), 735 (25), 954 (14).

(b) 1,1'-[(Propane-1,3-diyl)dioxy]bis[(11aS)-8-methoxy-1,2,3,11a-tetrahydro-5H-pyrrolo[2,1-c][1,4]benzodiazepine-5-one] (9a)

95% TFA (3 mL) was added drop-wise to dimer compound 8a (80 mg, 0.08 mmol) at 0° C. This was then stirred for 1 hr and the mixture was poured into saturated NaHCO$_3$ (30 mL) solution to naturalize the reaction mixture. The mixture was extracted with chloroform (3×20 mL). The organic layer was then washed water (20 mL), brine (20 mL) then dried (MgSO$_4$) and filtrated. The excess solvent was removed under reduced pressure to give the crude product, which was subjected to flash column chromatography (SiO$_2$, 2% methanol-chloroform). Removal of excess eluent under reduced pressure without heating afforded the final product 9a (31 mg, 0.06 mmol, 75%) as a solid: [α]$^{20}_D$=+515° (c=0.10, CHCl$_3$); $^1$H NMR (CDCl$_3$, 400 MHz): δ 2.01-2.11 (m, 4H, 2-H, 2'-H), 2.28-2.36 (m, 4H, 1-H, 1'-H), 2.38-2.45 (m, 2H, 13-H), 3.52-3.61 (m, 2H, 3-H, 3'-H), 3.67-3.75 (m, 2H, 11a-H, 11a'-H), 3.77-3.85 (m, 2H, 3-H, 3'-H), 3.90 (s, 6H, 7-OMe, 7'-OMe), 4.23-4.30 (m, 4H, 12-H, 12'-H), 6.79 (s, 2H, 9-H, 9'-H), 7.53 (s, 2H, 6-H, 6'-H), 7.65 (d, 2H, J=4, 11-H, 11'-H); $^{13}$C NMR (CDCl$_3$, 400 MHz): δ 24.1, 29.0, 29.6, 46.6, 53.7, 56.0, 65.6, 109.6, 112.9, 120.2, 140.7, 146.9, 151.8, 162.3, 164.6; IR (neat): 3350, 2956, 1599, 1506, 1447, 1385, 1262, 1216, 1091 cm$^{-1}$; MS (FAB) m/z (relative intensity) 597 ([M+2×MeOH]$^{+\cdot}$, 22), 565 ([M+MeOH]$^{+\cdot}$, 25), 533 (M$^{+\cdot}$, 100).

EXAMPLE 3 (n=4)

(a) 1,1'-[(Butane-1,4-diyl)dioxy]bis[(11S,11aS)-10-(tert-butyloxycarbonyl)-8-methoxy-11-(tetrahydro-pyran-2-yloxy)-1,2,3,10,11,11a-hexahydro-5H-pyrrolo[2,1-c][1,4]benzodiazepine-5-one] (8b)

1,4-Diiodobutane (69.1 mg, was added to the mixture of monomer 7 (0.2 g, 0.44 mmol, 1.0 equiv) and potassium carbonate (0.98 mmol, 2.2 equiv) in dry DMF (30 mL), and the resulting mixture was heated to 90° C. under a nitrogen atmosphere for 5 h. Removal of excess solvent under reduced pressure afforded a crude solid, which was subjected to flash column chromatography (SiO$_2$, 50% EtOAc-hexane) to afford the dimerized compound 8b (134 mg, 0.14 mmol, 63% yield, mixture of diastereomers from THP protecting group as a solid: [α]$^{20}$$_D$=+36° (c=0.19, CHCl$_3$); $^1$H NMR (CDCl$_3$, 400 MHz): δ 1.35 (s, 36H, Boc), 1.45-1.67 (m, 16H, THP), 1.68-1.86 (m, 8H, THP), 1.90-2.21 (m, 24H, 1-H, 2-H, 13-H), 3.44-3.78 (m, 16H, 3-H, 11a-H, THP), 3.84-4.02 (m, 16H, 7-OMe, THP), 4.04-4.25 (m, 8H, 12-H), 5.02-5.10 (m, 2H, THP), 5.11-5.20 (m, 2H, THP), 5.69-5.77 (d, 2H, 11-H), 5.79-5.89 (d, 2H, 11-H), 6.51 (s, 2H, 9-H), 6.88 (s, 2H, 9-H), 7.19 (s, 2H, 6-H), 7.28 (s, 2H, 6-H); $^{13}$C NMR (CDCl$_3$, 400 MHz): δ 19.8, 20.5, 23.1, 23.2, 25.3, 25.9, 28.1, 28.2, 28.9, 29.1, 30.9, 31.2, 46.2, 55.9, 56.2, 60.1, 63.3, 63.6, 68.6, 80.9, 88.2, 91.2, 96.2, 100.2, 111.1, 111.4, 113.4, 114.1, 118.5, 126.4, 129.8, 143.1, 147.9, 148.2, 151.5, 151.8, 155.8, 167.4, 167.6; IR (neat): 2945, 1704, 1644, 1604, 1513, 1449, 1392, 1327, 1217, 1163, 1022 cm$^{-1}$; MS (FAB) m/z (relative intensity) 973 ([M+Na]$^{+\cdot}$, 11), 951 (M$^{+\cdot}$, 100), 749 (36).

(b) 1,1'-[(Butane-1,4-diyl)dioxy]bis[(11aS)-8-methoxy-1,2,3,11a-tetrahydro-5H-pyrrolo[2,1-c][1,4]benzodiazepine-5-one] (9b)

95% TFA (3 mL) was added drop-wise to dimer compound 8b (134 mg, 0.14 mmol) at 0° C. This was then stirred for 1 hr and the mixture was poured into saturated NaHCO$_3$ (30 mL) solution to naturalize the reaction mixture. The mixture was extracted with chloroform (3×20 mL). The organic layer was then washed water (20 mL), brine (20 mL) then dried (MgSO$_4$) and filtrated. The excess solvent was removed under reduced pressure to give the crude product, which was subjected to flash column chromatography (SiO$_2$, 2% methanol-chloroform). Removal of excess eluent under reduced pressure without heating afforded the final product 9b (60 mg, 0.11 mmol, 78%) as a solid: [α]$^{20}$$_D$=+477° (c=0.09, CHCl$_3$); $^1$H NMR (CDCl$_3$, 400 MHz): δ 1.88-2.06 (m, 8H, 2-H, 2'-H, 13-H, 13'-H), 2.16-2.36 (m, 4H, 1-H, 1'-H), 3.46-3.57 (m, 2H, 3-H, 3'-H), 3.63-3.69 (m, 2H, 11a-H, 11a'-H), 3.60-3.69 (m, 2H, 3-H, 3'-H), 3.82 (s, 6H, 7-OMe, 7'-OMe), 3.98-4.19 (m, 4H, 12-H, 12'-H), 6.72 (s, 2H, 9-H, 9'-H), 7.44 (s, 2H, 6-H, 6'-H), 7.59 (d, 2H, J=4, 11-H, 11'-H); $^{13}$C NMR (CDCl$_3$, 400 MHz): δ 24.1, 25.8, 29.65, 46.6, 53.7, 56.0, 68.6, 109.6, 112.6, 120.2, 140.6, 147.0, 151.7, 162.8, 164.6; IR (neat): 3354, 2950, 1622, 1600, 1506, 1447, 1387, 1262, 1216, 1092, 1026 cm$^{-1}$; MS (FAB) m/z (relative intensity) 611 ([M+2×MeOH]$^{+\cdot}$, 9), 579 ([M+MeOH]$^{+\cdot}$, 19), 547 (M$^{+\cdot}$, 100).

EXAMPLE 4 (n=5)

(a) 1,1'-[(Pentane-1,5-diyl)dioxy]bis[(11S,11aS)-10-(tert-butyloxycarbonyl)-8-methoxy-11-(tetrahydro-pyran-2-yloxy)-1,2,3,10,11,11a-hexahydro-5H-pyrrolo[2,1-c][1,4]benzodiazepine-5-one] (8c)

1,5-Diiodopentane (72.2 mg, 0.22 mmol, 0.5 equiv) was added to the mixture of monomer 7 (0.2 g, 0.44 mmol, 1.0 equiv) and potassium carbonate (0.98 mmol, 2.2 equiv) in dry DMF (30 mL), and the resulting mixture was heated to 90° C. under a nitrogen atmosphere for 5 hours. Removal of excess solvent under reduced pressure afforded a crude solid, which was subjected to flash column chromatography (SiO$_2$, 50% EtOAc-hexane) to afford the dimerized compound 8c (160 mg, 0.1 6 mmol, 74% yield, mixture of diastereomers from THP protecting group) as a solid: [α]$^{20}$$_D$=+40° (c=0.16, CHCl$_3$); $^1$H NMR (CDCl$_3$, 400 MHz): δ 1.35 (s, 36H, Boc), 1.45-1.86 (m, 28H, 14-H, THP), 1.88-2.22 (m, 24H, 1-H, 2-H, 13-H), 3.44-3.77 (m, 16H, 3-H, 11a-H, THP), 3.82-4.02 (m, 16H, 7-OMe, THP), 4.03-4.19 (m, 8H, 12-H), 5.02-5.10 (m, 2H, THP), 5.11-5.20 (m, 2H, THP), 5.69-5.77 (d, 2H, 11-H), 5.79-5.89 (d, 2H, 11-H), 6.51 (s, 2H, 9-H), 6.88 (s, 2H, 9-H), 7.19 (s, 2H, 6-H), 7.22 (s, 2H, 6-H); $^{13}$C NMR (CDCl$_3$, 400 MHz): δ 19.8, 20.4, 22.5, 23.1, 23.2, 25.3, 28.1, 28.2, 28.8, 29.1, 30.9, 31.2, 46.3, 55.9, 56.2, 60.0, 60.1, 63.3, 64.4, 68.8, 80.9, 81.2, 88.3, 91.4, 96.0, 100.4, 111.2, 113.5, 114.1, 126.5, 129.8, 135.8, 147.4, 148.0, 150.9, 154.4, 167.4, 167.6; IR (neat): 2945, 1704, 1643, 1604, 1513, 1449, 1392, 1327, 1217, 1163, 1022 cm$^{-1}$; MS (FAB) m/z (relative intensity) 987 ([M+Na]$^{+\cdot}$, 14), 965 (M$^{+\cdot}$, 100), 863 (9).

(b) 1,11-[(Pentane-1,5-diyl)dioxy]bis[(11aS)-8-methoxy-1,2,3,11a-tetrahydro-5H-pyrrolo[2,1-c][1,4]benzodiazepine-5-one] (9c)

95% TFA (3 mL) was added drop-wise to dimer compound 8c (160 mg, 0.16 mmol) at 0° C. This was then stirred for 1 hr and the mixture was poured into saturated NaHCO$_3$ (30 mL) solution to naturalize the reaction mixture. The mixture was extracted with chloroform (3×20 mL). The organic layer was then washed water (20 mL), brine (20 mL) then dried (MgSO$_4$) and filtrated. The excess solvent was removed under reduced pressure to give the crude product, which was subjected to flash column chromatography (SiO$_2$, 2% methanol-chloroform). Removal of excess eluent under reduced pressure without heating afforded the final product 9c (72 mg, 0.13 mmol, 81%) as a solid: [α]$^{20}$$_D$=+416° (c=0.12, CHCl$_3$); $^1$H NMR (CDCl$_3$, 400 MHz): δ 1.62-1.71 (m, 2H, 14-H), 1.88-1.99 (m, 4H, 13-H, 13'-H), 2.01-2.11 (m, 4H, 2-H, 2'-H), 2.26-2.36 (m, 4H, 1-H, 1'-H), 3.53-3.62 (m, 2H, 3-H, 3'-H), 3.69-3.75 (m, 2H, 11a-H, 11a'-H), 3.76-3.85 (m, 2H, 3-H, 3'-H), 3.90 (s, 6H, 7-OMe, 7'-OMe), 4.02-4.21 (m, 4H, 12-H, 12'-H), 6.79 (s, 2H, 9-H, 9'-H), 7.50 (s, 2H, 6-H, 6'-H), 7.65 (d, 2H, J=4, 11-H, 11'-H); $^{13}$C NMR (CDCl$_3$, 400 MHz): δ 22.5, 24.1, 28.8, 29.6, 46.6, 53.7, 56.0, 68.9, 109.6, 112.6, 120.2, 140.5, 147.0, 151.7, 162.3, 164.6; IR (neat): 3325, 2946, 1600, 1505, 1448, 1386, 1262, 1217, 1091, 1023 cm$^{-1}$; MS (FAB) m/z (relative intensity) 625 ([M+2×MeOH]$^{+\cdot}$, 19), 593 ([M+MeOH]$^{+\cdot}$, 25), 561 (M$^{+\cdot}$, 100).

EXAMPLE 5 (n=6)

(a) 1,1'-[(Hexane-1,6-diyl)dioxy]bis[(11S,11aS)-10-(tert-butyloxycarbonyl)-8-methoxy-11-(tetrahydropyran-2-yloxy)-1,2,3,10,11,11a-hexahydro-5H-pyrrolo[2,1-c][1,4]benzodiazepine-5-one] (8d)

1,6-Diiodohexane (75.3 mg, 0.00 mmol, 0.5 equiv) was added to the mixture of monomer 7 (0.2 g, 0.44 mmol, 1.0 equiv) and potassium carbonate (0.98 mmol, 2.2 equiv) in dry DMF (30 mL), and the resulting mixture was heated to 90° C. under a nitrogen atmosphere for 5 hours. Removal of excess solvent under reduced pressure afforded a crude solid, which was subjected to flash column chromatography (SiO$_2$, 50% EtOAc-hexane) to afford the dimerized compound 8d (174 mg, 0.17 mmol, 79% yield, mixture of diastereomers from THP protecting group) as a solid: $[\alpha]^{20}_D$=+44° (c=0.16, CHCl$_3$); $^1$H NMR (CDCl$_3$, 400 MHz): δ 1.25-1.67 (m, 60H, 14-H, Boc, THP), 1.70-2.24 (m, 32H, 1-H, 2-H, 13-H, THP), 3.44-3.77 (m, 16H, 3-H, 11a-H, THP), 3.84-4.18 (m, 24H, 12-H, 7-OMe, THP), 5.02-5.10 (m, 2H, THP), 5.11-5.20 (m, 2H, THP), 5.69-5.77 (d, 2H, 11-H), 5.79-5.89 (d, 2H, 11-H), 6.51 (s, 2H, 9-H), 6.87 (s, 2H, 9-H), 7.18 (s, 2H, 6-H), 7.22 (s, 2H, 6-H); $^{13}$C NMR (CDCl$_3$, 400 MHz): δ 19.8, 20.3, 23.1, 23.2, 25.3, 25.8, 28.1, 28.2, 28.9, 29.0, 29.1, 30.9, 31.2, 46.3, 55.9, 56.2, 60.0, 60.1, 63.3, 64.1, 68.9, 80.9, 81.2, 88.2, 91.1, 95.0, 100.5, 111.2, 111.7, 113.5, 114.1, 118.2, 127.1, 134.8, 147.7, 148.0, 155.2, 162.3, 163.0, 167.4, 167.6; IR (neat): 2943, 1703, 1644, 1604, 1513, 1449, 1392, 1327, 1217, 1163, 1022 cm$^{-1}$; MS (FAB) m/z (relative intensity) 1001 ([M+Na]$^+$·, 10), 979 (M$^+$·, 100), 777 (24), 877 (12).

(b) 1,1'-[(Hexane-1,6-diyl)dioxy]bis[(11aS)-8-methoxy-1,2,3,11a-tetrahydro-5H-pyrrolo[2,1-c][1,4]benzodiazepine-5-one] (9d)

95% TFA (3 mL) was added drop-wise to dimer compound 8d (174 mg, 0.17 mmol) at 0° C. This was then stirred for 1 hr and the mixture was poured into saturated NaHCO$_3$ (30 mL) solution to naturalize the reaction mixture. The mixture was extracted with chloroform (3×20 mL). The organic layer was then washed water (20 mL), brine (20 mL) then dried (MgSO$_4$) and filtrated. The excess solvent was removed under reduced pressure to give the crude product, which was subjected to flash column chromatography (SiO$_2$, 2% methanol-chloroform). Removal of excess eluent under reduced pressure without heating afforded the final product 9d (86 mg, 0.15 mmol, 88%) as a solid: $[\alpha]^{20}_D$=+500° (c=0.09, CHCl$_3$); $^1$H NMR (CDCl$_3$, 400 MHz): δ 1.39-1.55 (m, 4H, 14-H, 14'-H), 1.72-1.89 (m, 4H, 13-H, 13'-H), 1.91-2.05 (m, 4H, 2-H, 2'-H), 2.17-2.31 (m, 4H, 1-H, 1'-H), 3.45-3.56 (m, 2H, 3-H, 3'-H), 3.62-3.69 (m, 2H, 11a-H, 11a'-H), 3.70-3.79 (m, 2H, 3-H, 3'-H), 3.83 (s, 6H, 7-OMe, 7'-OMe), 3.95-4.13 (m, 4H, 12-H, 12'-H), 6.73 (s, 2H, 9-H, 9'-H), 7.43 (s, 2H, 6-H, 6'-H), 7.58 (d, 2H, J=4, 11-H, 11'-H); $^{13}$C NMR (CDCl$_3$, 400 MHz): δ 24.1, 25.7, 29.0, 29.6, 46.6, 53.7, 56.0, 69.0, 109.6, 112.5, 120.2, 140.5, 147.1, 151.7, 162.8, 164.6; IR (neat): 3385, 2945, 1622, 1599, 1506, 1447, 1387, 1261, 1217, 1093 cm$^{-1}$; MS (FAB) m/z (relative intensity) 639 ([M+2× MeOH]$^+$·, 4), 607 ([M+MeOH]$^+$·, 12), 575 (M$^+$·, 100).

EXAMPLE 6 (n=7)

(a) 1,1'-[(Heptane-1,7-diyl)dioxy]bis[(11S,11aS)-10-(tert-butyloxycarbonyl)-8-methoxy-11-(tetrahydropyran-2-yloxy)-1,2,3,10,11,11a-hexahydro-5H-pyrrolo[2,1-c][1,4]benzodiazepine-5-one] (8e)

1,7-Dibromoheptane (57.5 mg, 0.22 mmol, 0.5 equiv) was added to the mixture of monomer 7 (0.2 g, 0.44 mmol, 1.0 equiv) potassium carbonate (0.98 mmol, 2.2 equiv) and a catalytic amount of potassium iodide in dry DMF (30 mL), and the resulting mixture was heated to 90° C. under a nitrogen atmosphere for 5 h. Removal of excess solvent under reduced pressure afforded a crude solid, which was subjected to flash column chromatography (SiO$_2$, 50% EtOAc-hexane) to afford the dimerized compound 8e (190 mg, 0.19 mmol, 88% yield, mixture of diastereomers from THP protecting group) as a solid: $[\alpha]^{20}_D$=+59° (c=0.16, CHCl$_3$); $^1$H NMR (CDCl$_3$, 400 MHz): δ 1.25-1.67 (m, 64H, 14-H, 15-H, Boc, THP), 1.68-1.92 (16H, 13-H, THP), 1.93-2.21 (m, 16H, 1-H, 2-H), 3.44-3.75 (m, 16H, 3-H, 11a-H, THP), 3.84-4.17 (m, 24H, 12-H, 7-OMe, THP), 5.02-5.10 (m, 2H, THP), 5.11-5.20 (m, 2H, THP), 5.69-5.77 (d, 2H, 11-H), 5.79-5.89 (d, 2H, 11-H), 6.51 (s, 2H, 9-H), 6.87 (s, 2H, 9-H), 7.19 (s, 2H, 6-H), 7.22 (s, 2H, 6-H); $^{13}$C NMR (CDCl$_3$, 400 MHz): δ 19.8, 20.4, 23.1, 23.2, 25.3, 25.9, 28.1, 28.2, 28.9, 29.0, 29.1, 30.9, 31.2, 46.3, 55.9, 56.2, 60.0, 60.1, 63.3, 64.4, 69.0, 80.6, 80.9, 88.2, 91.2, 96.4, 100.2, 111.3, 111.9, 113.4, 114.0, 115.5, 116.1, 126.3, 129.7, 149.6, 149.9, 151.1, 155.5, 167.4, 167.6; IR (neat): 2942, 1704, 1643, 1604, 1514, 1450, 1392, 1327, 1218, 1164, 1022 cm$^{-1}$; MS (FAB) m/z (relative intensity) 1015 ([M+Na]$^+$·, 12), 993 (M$^+$·, 100), 791 (23), 891 (9).

(b) 1,1'-[(Heptane-1,7-diyl)dioxy]bis[(11aS)-8-methoxy-1,2,3,11a-tetrahydro-5H-pyrrolo[2,1-c][1,4]benzodiazepine-5-one] (9e)

95% TFA (3 mL) was added drop-wise to dimer compound 8e (195 mg, 0.19 mmol) at 0° C. This was then stirred for 1 hr and the mixture was poured into saturated NaHCO$_3$ (30 mL) solution to naturalize the reaction mixture. The mixture was extracted with chloroform (3×20 mL). The organic layer was then washed water (20 mL), brine (20 mL) then dried (MgSO$_4$) and filtrated. The excess solvent was removed under reduced pressure to give the crude product, which was subjected to flash column chromatography (SiO$_2$, 2% methanol-chloroform). Removal of excess eluent under reduced pressure without heating afforded the final product 9e (76 mg, 0.12 mmol, 68%) as a solid: $[\alpha]^{20}_D$=+473° (c=0.14, CHCl$_3$); $^1$H NMR (CDCl$_3$, 400 MHz): δ 1.41-1.55 (m, 6H, 14-H, 14'-H, 15-H), 1.85-1.94 (m, 4H, 13-H, 13'-H), 2.04-2.10 (m, 4H, 2-H, 2'-H), 2.28-2.38 (m, 4H, 1-H, 1'-H), 3.56-3.63 (m, 2H, 3-H, 3'-H), 3.72-3.76 (m, 2H, 11a-H, 11a'-H), 3.79-3.85 (m, 2H, 3-H, 3'-H), 3.92 (s, 6H, 7-OMe, 7'-OMe), 4.01-4.19 (m, 4H, 12-H, 12'-H), 6.79 (s, 2H, 9-H, 9'-H), 7.49 (s, 2H, 6-H, 6'-H), 7.64 (d, 2H, J=4, 11-H, 11'-H); $^{13}$C NMR (CDCl$_3$, 400 MHz): δ 24.1, 25.9, 29.0, 29.2, 29.6, 46.6, 53.7, 56.0, 69.1, 109.6, 112.5, 120.2, 140.5, 147.1, 151.6, 162.2, 164.6; IR (neat): 3325, 2935, 1600, 1506, 1448, 1388, 1261, 1217, 1022 cm$^{-1}$; MS (FAB) m/z (relative intensity) 653 ([M+2× MeOH]$^+$·, 14), 621 ([M+MeOH]$^+$·, 20), 589 (M$^+$·, 100).

EXAMPLE 7 (n=8)

(a) 1,1'-[(Octane-1,8-diyl)dioxy]bis[(11S,11aS)-10-(tert-butyloxycarbonyl)-8-methoxy-11-(tetrahydropyran-2-yloxy)-1,2,3,10,11,11a-hexahydro-5H-pyrrolo[2,1-c][1,4]benzodiazepine-5-one] (8f)

1,8-Diiodooctane (81.6 mg, 0.22 mmol, 0.5 equiv) was added to the mixture of monomer 7 (0.2 g, 0.44 mmol, 1.0 equiv) and potassium carbonate (0.98 mmol, 2.2 equiv) in dry DMF (30 mL), and the resulting mixture was heated to 90° C. under a nitrogen atmosphere for 5 h. Removal of excess solvent under reduced pressure afforded a crude solid, which was subjected to flash column chromatography (SiO$_2$, 50% EtOAc-hexane) to afford the dimerized compound 8f (191 mg, 0.18 mmol, 85% yield, mixture of diastereomers from THP protecting group) as a solid: $[\alpha]^{20}_D=+50°$ (c=0.15, CHCl$_3$); $^1$H NMR (CDCl$_3$, 400 MHz): δ 1.27-1.66 (m, 68H, 14-H, 15-H, Boc, THP), 1.68-1.91 (16H, 3-H, THP), 1.93-2.20 (m, 16H, 1-H, 2-H), 3.45-3.75 (m, 16H, 3-H, 11a-H, THP), 3.83-4.14 (m, 24H, 12-H, 7-OMe, THP), 5.02-5.10 (m, 2H, THP), 5.11-5.20 (m, 2H, THP), 5.69-5.77 (d, 2H, 11-H), 5.79-5.89 (d, 2H, 11-H), 6.51 (s, 2H, 9-H), 6.87 (s, 2H, 9-H), 7.19 (s, 2H, 6-H), 7.22 (s, 2H, 6-H); $^{13}$C NMR (CDCl$_3$, 400 MHz): δ 19.8, 20.4, 23.1, 23.2, 25.3, 25.9, 28.1, 28.2, 28.9, 29.0, 29.1, 29.3, 30.9, 31.2, 46.3, 55.9, 56.2, 60.0, 60.1, 63.3, 64.4, 69.0, 80.9, 81.2, 88.2, 91.2, 95.8, 100.2, 111.1, 111.7, 113.4, 114.0, 122.0, 126.4, 129.7, 138.0, 147.8, 148.1, 150.1, 150.5, 155.7, 167.4, 167.6; IR (neat): 2941, 1704, 1643, 1604, 1514, 1450, 1392, 1327, 1218, 1164, 1022 cm$^{-1}$; MS (FAB) m/z (relative intensity) 1029 ([M+Na]$^{+\cdot}$, 30), 1007 (M$^{+\cdot}$, 100), 905 (15).

(b) 1,1'-[(Octane-1,8-diyl)dioxy]bis[(11aS)-8-methoxy-1,2,3,11a-tetrahydro-5H-pyrrolo[2,1-c][1,4]benzodiazepine-5-one] (9f)

95% TFA (3 mL) was added drop-wise to dimer compound 8f (191 mg, 0.18 mmol) at 0° C. This was then stirred for 1 hr and the mixture was poured into saturated NaHCO$_3$ (30 mL) solution to naturalize the reaction mixture. The mixture was extracted with chloroform (3×20 mL). The organic layer was then washed water (20 mL), brine (20 mL) then dried (MgSO$_4$) and filtrated. The excess solvent was removed under reduced pressure to give the crude product, which was subjected to flash column chromatography (SiO$_2$, 2% methanol-chloroform). Removal of excess eluent under reduced pressure without heating afforded the final product 9f (106 mg, 0.17 mmol, 97%) as a solid: $[\alpha]^{20}_D=+467°$ (c=0.14, CHCl$_3$); $^1$H NMR (CDCl$_3$, 400 MHz): δ 1.34-1.53 (m, 8H, 14-H, 14'-H, 15-H, 15'-H), 1.78-1.91 (m, 4H, 13-H, 13'-H), 1.96-2.10 (m, 4H, 2-H, 2'-H), 2.25-2.38 (m, 4H, 1-H, 1'-H), 3.54-3.63 (m, 2H, 3-H, 3'-H), 3.70-3.76 (m, 2H, 11a-H, 11a'-H), 3.77-3.88 (m, 2H, 3-H, 3'-H), 3.90 (s, 6H, 7-OMe, 7'-OMe), 4.04-4.17 (m, 4H, 12-H, 12'-H), 6.81 (s, 2H, 9-H, 9'-H), 7.52 (s, 2H, 6-H, 6'-H), 7.67 (d, 2H, J=4, 11-H, 11'-H); $^{13}$C NMR (CDCl$_3$, 400 MHz): δ 24.1, 25.8, 29.0, 29.1, 29.6, 46.6, 53.7, 56.0, 69.0, 109.6, 112.5, 120.2, 140.5, 147.1, 151.6, 162.3, 164.6; IR (neat): 3326, 2937, 1599, 1506, 1448, 1387, 1262, 1217, 1092, 1023 cm$^{-1}$; MS (FAB) m/z (relative intensity) 667 ([M+2×MeOH]$^{+\cdot}$, 7), 635 ([M+MeOH]$^{+\cdot}$, 15), 603 (M$^{+\cdot}$, 100).

EXAMPLE 8 (n=9)

(a) 1,1'-[(Nonane-1,9-diyl)dioxy]bis[(11S,11aS)-10-(tert-butyloxycarbonyl)-8-methoxy-11-(tetrahydro-pyran-2-yloxy)-1,2,3,10,11,11a-hexahydro-5H-pyrrolo[2,1-c][1,4]benzodiazepine-5-one] (8g)

1,9-Dibromononane (63.7 mg, 0.22 mmol, 0.5 equiv) was added to the mixture of monomer 7 (0.2 g, 0.44 mmol, 1.0 equiv) potassium carbonate (0.98 mmol, 2.2 equiv) and a catalytic amount of potassium iodide in dry DMF (30 mL), and the resulting mixture was heated to 90° C. under a nitrogen atmosphere for 5 h. Removal of excess solvent under reduced pressure afforded a crude solid, which was subjected to flash column chromatography (SiO$_2$, 50% EtOAc-hexane) to afford the dimerized compound 8g (181 mg, 0.17 mmol, 79% yield, mixture of diastereomers from THP protecting group) as a solid: $[\alpha]^{20}_D=+56°$ (c=0.16, CHCl$_3$); $^1$H NMR (CDCl$_3$, 400 MHz): δ 1.27-1.66 (m, 72H, 14-H, 15-H, 16-H, Boc, THP), 1.68-1.92 (16H, 13-H, THP), 1.93-2.20 (m, 16H, 1-H, 2-H), 3.45-3.75 (m, 16H, 3-H, 11a-H, THP), 3.83-4.14 (m, 24H, 12-H, 7-OMe, THP), 5.02-5.10 (m, 2H, THP), 5.12-5.19 (m, 2H, THP), 5.69-5.77 (d, 2H, 11-H), 5.79-5.89 (d, 2H, 11-H), 6.51 (s, 2H, 9-H), 6.87 (s, 2H, 9-H), 7.19 (s, 2H, 6-H), 7.22 (s, 2H, 6-H); $^{13}$C NMR (CDCl$_3$, 400 MHz): δ 19.8, 20.4, 23.1, 23.2, 25.2, 25.3, 25.9, 28.1, 28.2, 28.9, 29.0, 29.1, 29.2, 29.3, 29.4, 30.9, 31.2, 46.2, 55.9, 56.2, 60.0, 60.1, 63.3, 64.4, 69.0, 69.1, 80.9, 81.2, 88.2, 91.2, 95.8, 100.2, 111.1, 111.5, 113.4, 114.0, 120.5, 129.6, 138.2, 147.8, 148.1, 151.2, 151.5, 161.9, 167.4, 167.6; IR (neat): 2938, 1703, 1643, 1604, 1513, 1449, 1392, 1327, 1217, 1163, 1022 cm$^{-1}$; MS (FAB) m/z (relative intensity) 1043 ([M+Na]$^{+\cdot}$, 21), 1021 (M$^{+\cdot}$, 100), 819 (20), 919 (16).

(b) 1,1'-[(Nonane-1,9-diyl)dioxy]bis[(11aS)-8-methoxy-1,2,3,11a-tetrahydro-5H-pyrrolo[2,1-c][1,4]benzodiazepine-5-one] (9g)

95% TFA (3 mL) was added drop-wise to dimer compound 8g (170 mg, 0.18 mmol) at 0° C. This was then stirred for 1 hr and the mixture was poured into saturated NaHCO$_3$ (30 mL) solution to naturalize the reaction mixture. The mixture was extracted with chloroform (3×20 mL). The organic layer was then washed water (20 mL), brine (20 mL) then dried (MgSO$_4$) and filtrated. The excess solvent was removed under reduced pressure to give the crude product, which was subjected to flash column chromatography (SiO$_2$, 2% methanol-chloroform). Removal of excess eluent under reduced pressure without heating afforded the final product 9g (93 mg, 0.15 mmol, 88%) as a solid: $[\alpha]^{20}_D=+547°$ (c=0.13, CHCl$_3$); $^1$H NMR (CDCl$_3$, 400 MHz): δ 1.31-1.53 (m, 10H, 14-H, 14'-H, 15-H, 15'-H, 16-H), 1.83-1.94 (m, 4H, 13-H, 13'-H), 2.00-2.12 (m, 4H, 2-H, 2'-H), 2.27-2.38 (m, 4H, 1-H, 1'-H), 3.54-3.64 (m, 2H, 3-H, 3'-H), 3.69-3.78 (m, 2H, 11a-H, 11a'-H), 3.79-3.87 (m, 2H, 3-H, 3'-H), 3.92 (s, 6H, 7-OMe, 7'-OMe), 4.01-4.19 (m, 4H, 12-H, 12'-H), 6.81 (s, 2H, 9-H, 9'-H), 7.52 (s, 2H, 6-H, 6'-H), 7.67 (d, 2H, J=4, 11-H, 11'-H); $^{13}$C NMR (CDCl$_3$, 400 MHz): δ 24.1, 25.9, 29.0, 29.3, 29.4, 29.6, 46.6, 53.7, 56.0, 69.1, 109.6, 112.5, 120.2, 140.5, 147.1, 151.6, 162.2, 164.6; IR (neat): 3325, 2933, 1600, 1507, 1448, 1388, 1261, 1217, 1092, 1024 cm$^{-1}$; MS (FAB) m/z (relative intensity) 617 (M$^{+\cdot}$, 100), 635 (10), 785 (6).

EXAMPLE 9 (n=10)

(a) 1,1'-[(Decane-1,10-diyl)dioxy]bis[(11S,11aS)-10-(tert-butyloxycarbonyl)-8-methoxy-11-(tetrahydro-pyran-2-yloxy)-1,2,3,10,11,11a-hexahydro-5H-pyrrolo[2,1-c][1,4]benzodiazepine-5-one] (8h)

1,10-Diiododecane (87.8 mg, 0.22 mmol, 0.5 equiv) was added to the mixture of monomer 7 (0.2 g, 0.44 mmol, 1.0 equiv) and potassium carbonate (0.98 mmol, 2.2 equiv) in dry DMF (30 mL), and the resulting mixture was heated to 90° C. under a nitrogen atmosphere for 5 h. Removal of excess solvent under reduced pressure afforded a crude solid, which was subjected to flash column chromatography (SiO$_2$, 50% EtOAc-hexane) to afford the dimerized compound 8h (191 mg, 0.1 8 mmol, 82% yield, mixture of diastereomers from THP protecting group) as a solid: $[\alpha]^{20}_D=+75°$ (c=0.10, CHCl$_3$); $^1$H NMR (CDCl$_3$, 400 MHz): δ 1.25-1.59 (m, 76H, 14-H, 15-H, 16-H, Boc, THP), 1.68-1.92 (16H, 13-H, THP), 1.93-2.20 (m, 16H, 1-H, 2-H), 3.45-3.75 (m, 16H, 3-H, 11a-H, THP), 3.83-4.14 (m, 24H, 12-H, 7-OMe, THP), 5.02-5.10 (m, 2H, THP), 5.12-5.19 (m, 2H, THP), 5.69-5.77 (d, 2H, 11-H), 5.79-5.89 (d, 2H, 11-H), 6.49 (s, 2H, 9-H), 6.86 (s, 2H, 9-H), 7.17 (s, 2H, 6-H), 7.21 (s, 2H, 6-H); $^{13}$C NMR (CDCl$_3$, 400 MHz): δ 19.9, 20.4, 23.1, 23.2, 25.2, 25.3, 25.9, 28.1, 28.2, 28.9, 29.0, 29.1, 29.2, 29.3, 29.5, 30.9, 31.3, 46.3, 55.9, 56.2, 60.0, 60.1, 63.3, 69.1, 80.9, 81.2, 88.2, 91.2, 95.8, 100.2, 111.1, 111.5, 113.4, 114.0, 121.6, 126.4, 141.0, 143.1, 148.1, 148.4, 155.4, 167.4, 167.6; IR (neat): 2937, 1703, 1643, 1604, 1513, 1450, 1392, 1327, 1218, 1164, 1022 cm$^{-1}$; MS (FAB) m/z (relative intensity) 1057 ([M+Na]$^+$·, 34), 1035 (M$^+$·, 100), 833 (26), 933 (25).

(b) 1,1'-[(Decane-1,10-diyl)dioxy]bis[(11aS)-8-methoxy-1,2,3,11a-tetrahydro-5H-pyrrolo[2,1-c][1,4]benzodiazepine-5-one] (9h)

95% TFA (3 mL) was added drop-wise to dimer compound 8h (191 mg, 0.18 mmol) at 0° C. This was then stirred for 1 hr and the mixture was poured into saturated NaHCO$_3$ (30 mL) solution to naturalize the reaction mixture. The mixture was extracted with chloroform (3×20 mL). The organic layer was then washed water (20 mL), brine (20 mL) then dried (MgSO$_4$) and filtrated. The excess solvent was removed under reduced pressure to give the crude product, which was subjected to flash column chromatography (SiO$_2$, 2% methanol-chloroform). Removal of excess eluent under reduced pressure without heating afforded the final product 9h (103 mg, 0.16 mmol, 90%) as a solid: $[\alpha]^{20}_D$=+387° (c=0.17, CHCl$_3$); $^1$H NMR (CDCl$_3$, 400 MHz): δ 1.25-1.50 (m, 12H, 14-H, 14'-H, 15-H, 15'-H, 16-H, 16'-H), 1.72-1.92 (m, 4H, 13-H, 13'-H), 1.98-2.09 (m, 4H, 2-H, 2'-H), 2.25-2.38 (m, 4H, 1-H, 1'-H), 3.52-3.62 (m, 2H, 3-H, 3'-H), 3.68-3.73 (m, 2H, 11a-H, 11a'-H), 3.76-3.85 (m, 2H, 3-H, 3'-H), 3.90 (s, 6H, 7-OMe, 7'-OMe), 3.95-4.19 (m, 4H, 12-H, 12'-H), 6.79 (s, 2H, 9-H; 9'-H), 7.50 (s, 2H, 6-H, 6'-H), 7.64 (d, 2H, J=4, 11-H, 11'-H); $^{13}$C NMR (CDCl$_3$, 400 MHz): δ 24.1, 25.9, 29.0, 29.3, 29.4, 29.6, 46.6, 53.7, 56.0, 69.7, 109.6, 112.5, 120.2, 140.5, 147.1, 151.6, 162.2, 164.6; IR (neat): 3325, 2931, 1600, 1506, 1448, 1388, 1262, 1217, 1092, 1024 cm$^{-1}$; MS (FAB) m/z (relative intensity) 695 ([M+2×MeOH]$^+$·, 14), 663 ([M+MeOH]$^+$·, 20), 631 (M$^+$·, 100).

EXAMPLE 10 (n=11)

(a) 1,1'-[(Undecane-1,11-diyl)dioxy]bis[(11S,11aS)-10-(tert-butyloxycarbonyl)-8-methoxy-11-(tetrahydro-pyran-2-yloxy)-1,2,3,10,11,11a-hexahydro-5H-pyrrolo[2,1-c][1,4]benzodiazepine-5-one] (8i)

1,1'-Dibromoundecane (70.0 mg, 0.22 mmol, 0.5 equiv) was added to the mixture of monomer 7 (0.2 g, 0.44 mmol, 1.0 equiv) potassium carbonate (0.98 mmol, 2.2 equiv) and a catalytic amount of potassium iodide in dry DMF (30 mL), and the resulting mixture was heated to 90° C. under a nitrogen atmosphere for 5 h. Removal of excess solvent under reduced pressure afforded a crude solid, which was subjected to flash column chromatography (SiO$_2$, 50% EtOAc-hexane) to afford the dimerized compound 8i (217 mg, 0.20 mmol, 94% yield, mixture of diastereomers from THP protecting group) as a solid: $[\alpha]^{20}_D$=+52° (c=0.17, CHCl$_3$); $^1$H NMR (CDCl$_3$, 400 MHz): δ 1.27-1.60 (m, 80H, 14-H, 15-H, 16-H, 17-H, Boc, THP), 1.71-1.89 (16H, 13-H, THP), 1.93-2.20 (m, 16H, 1-H, 2-H), 3.45-3.75 (m, 16H, 3-H, 11a-H, THP), 3.83-4.14 (m, 24H, 12-H, 7-OMe, THP), 5.02-5.10 (m, 2H, THP), 5.12-5.19 (m, 2H, THP), 5.69-5.77 (d, 2H, 11-H), 5.79-5.89 (d, 2H, 11-H), 6.51 (s, 2H, 9-H), 6.87 (s, 2H, 9-H), 7.19 (s, 2H, 6-H), 7.22 (s, 2H, 6-H); $^{13}$C NMR (CDCl$_3$, 400 MHz): δ 19.9, 20.4, 23.1, 23.2, 25.3, 25.9, 28.1, 28.2, 28.9, 29.0, 29.1, 29.2, 29.3, 29.5, 30.9, 31.2, 46.3, 55.9, 56.2, 60.0, 60.1, 63.3, 64.4, 69.1, 80.9, 81.2, 88.2, 91.2, 95.8, 100.2, 111.1, 111.5, 113.4, 114.0, 126.3, 129.6, 134.1, 138.8, 148.0, 148.4, 155.3, 155.6, 167.4, 167.6; IR (neat): 2935, 1704, 1643, 1604, 1513, 1449, 1392, 1327, 1218, 1164, 1022 cm$^{-1}$; MS (FAB) m/z (relative intensity) 1071 ([M+Na]$^+$·, 16), 1049 (M$^+$·, 100), 947 (15), 847 (13).

(b) 1,1'-[(Undecane-1,11-diyl)dioxy]bis[(11aS)-8-methoxy-1,2,3,11a-tetrahydro-5H-pyrrolo[2,1-c][1,4]benzodiazepine-5-one] (9i)

95% TFA (3 mL) was added drop-wise to dimer compound 8i (217 mg, 0.20 mmol) at 0° C. This was then stirred for 1 hr and the mixture was poured into saturated NaHCO$_3$ (30 mL) solution to naturalize the reaction mixture. The mixture was extracted with chloroform (3×20 mL). The organic layer was then washed water (20 mL), brine (20 mL) then dried (MgSO$_4$) and filtrated. The excess solvent was removed under reduced pressure to give the crude product, which was subjected to flash column chromatography (SiO$_2$, 2% methanol-chloroform). Removal of excess eluent under reduced pressure without heating afforded the final product 9i (113 mg, 0.17 mmol, 87%) as a solid: $[\alpha]^{20}_D$=+401° (c=0.19, CHCl$_3$); $^1$H NMR (CDCl$_3$, 400 MHz): δ 1.26-1.52 (m, 14H, 14-H, 14'-H, 15-H, 15'-H, 16-H, 16'-H, 17-H), 1.84-1.92 (m, 4H, 13-H, 13'-H), 2.01-2.11 (m, 4H, 2-H, 2'-H), 2.27-2.36 (m, 4H, 1-H, 1'-H), 3.55-3.64 (m, 2H, 3-H, 3'-H), 3.70-3.76 (m, 2H, 11a-H, 11a'-H), 3.78-3.87 (m, 2H, 3-H, 3'-H), 3.92 (s, 6H, 7-OMe, 7'-OMe), 4.02-4.20 (m, 4H, 12-H, 12'-H), 6.81 (s, 2H, 9-H, 9'-H), 7.52 (s, 2H, 6-H, 6'-H), 7.67 (d, 2H, J=4, 11-H, 11'-H); $^{13}$C NMR (CDCl$_3$, 400 MHz): δ 24.1, 25.9, 29.0, 29.3, 29.5, 29.6, 46.6, 53.7, 56.0, 69.1, 109.6, 112.5, 120.2, 140.5, 147.1, 151.6, 162.2, 164.6; IR (neat): 3325, 2928, 1600, 1507, 1448, 1261, 1217, 1023 cm$^{-1}$; MS (FAB) m/z (relative intensity) 709 ([M+2×MeOH]$^+$·, 14), 677 ([M+MeOH]$^+$·, 20), 645 (M$^+$·, 100).

EXAMPLE 11 (n=12)

(a) 1,1'-[(Dodecane-1,12-diyl)dioxy]bis[(11S,11aS)-10-(tert-butyloxycarbonyl)-8-methoxy-11-(tetrahydro-pyran-2-yloxy)-1,2,3,10,11,11a-hexahydro-5H-pyrrolo[2,1-c][1,4]benzodiazepine-5-one] (8j)

1,12-Dibromododecane (73.1 mg, 0.22 mmol, 0.5 equiv) was added to the mixture of monomer 7 (0.2 g, 0.44 mmol, 1.0 equiv) potassium carbonate (0.98 mmol, 2.2 equiv) and a catalytic amount of potassium iodide in dry DMF (30 mL), and the resulting mixture was heated to 90° C. under a nitrogen atmosphere for 5 h. Removal of excess solvent under reduced pressure afforded a crude solid, which was subjected to flash column chromatography (SiO$_2$, 50% EtOAc-hexane) to afford the dimerized compound 8j (208 mg, 0.19 mmol, 87% yield, mixture of diastereomers from THP protecting group) as a solid: $[\alpha]^{20}_D$=+50° (c=0.20, CHCl$_3$); $^1$H NMR (CDCl$_3$, 400 MHz): δ 1.26-1.68 (m, 84H, 14-H, 15-H, 16-H, 17-H, Boc, THP), 1.69-1.89 (16H, 13-H, THP), 1.93-2.20 (m, 16H, 1-H, 2-H), 3.44-3.75 (m, 16H, 3-H, 11a-H, THP), 3.83-4.14 (m, 24H, 12-H, 7-OMe, THP), 5.02-5.10 (m, 2H, THP), 5.12-5.19 (m, 2H, THP), 5.69-5.77 (d, 2H, 11-H), 5.79-5.89 (d, 2H, 11-H), 6.50 (s, 2H, 9-H), 6.87 (s, 2H, 9-H), 7.19 (s, 2H, 6-H), 7.22 (s, 2H, 6-H); $^{13}$C NMR (CDCl$_3$, 400 MHz): δ 19.9, 20.4, 23.1, 23.2, 25.2, 25.3, 25.9, 28.1, 28.2, 28.9, 29.0, 29.1, 29.2, 29.3, 29.56, 29.58, 30.9, 31.2, 46.2, 55.9, 56.2, 60.0, 60.1, 63.3, 64.4, 69.12, 69.15, 80.9, 81.2, 88.2, 91.2, 95.8, 100.2, 111.1, 111.5, 113.4, 114.0, 126.3, 129.6, 134.1, 138.8, 147.8, 148.1, 151.5, 155.3, 167.4, 167.6; IR (neat): 2932, 1703, 1643, 1604, 1513, 1450, 1392, 1327, 1218, 1164, 1022 cm$^{-1}$; MS (FAB) m/z (relative intensity) 1085 ([M+Na]$^+$, 28), 1063 (M$^+$, 100), 961 (17), 861 (13).

(b) 1,1'-[(Dodecane-1,12-diyl)dioxy]bis[(11aS)-8-methoxy-1,2,3,11a-tetrahydro-5H-pyrrolo[2,1-c][1,4]benzodiazepine-5-one] (9j)

95% TFA (3 mL) was added drop-wise to dimer compound 8j (208 mg, 0.19 mmol) at 0° C. This was then stirred for 1 hr and the mixture was poured into saturated NaHCO$_3$ (30 mL) solution to naturalize the reaction mixture. The mixture was extracted with chloroform (3×20 mL). The organic layer was then washed water (20 mL), brine (20 mL) then dried (MgSO$_4$) and filtrated. The excess solvent was removed under reduced pressure to give the crude product, which was subjected to flash column chromatography (SiO$_2$, 2% methanol-chloroform). Removal of excess eluent under reduced pressure without heating afforded the final product 9j (107 mg, 0.16 mmol, 85%) as a solid: $[\alpha]^{20}_D$=+506° (c=0.15, CHCl$_3$); $^1$H NMR (CDCl$_3$, 400 MHz): δ 1.26-1.52 (m, 16H, 14-H, 14'-H, 15-H, 15'-H, 16-H, 16'-H, 17-H, 17'-H), 1.83-1.92 (m, 4H, 13-H, 13'-H), 2.01-2.12 (m, 4H, 2-H, 2'-H), 2.28-2.37 (m, 4H, 1-H, 1'-H), 3.55-3.64 (m, 2H, 3-H, 3'-H), 3.70-3.77 (m, 2H, 11a-H, 11a'-H), 3.78-3.87 (m, 2H, 3-H, 3'-H), 3.92 (s, 6H, 7-OMe, 7'-OMe), 4.03-4.19 (m, 4H, 12-H, 12'-H), 6.81 (s, 2H, 9-H, 9'-H), 7.52 (s, 2H, 6-H, 6'-H), 7.67 (d, 2H, J=4, 11-H, 11'-H); $^{13}$C NMR (CDCl$_3$, 400 MHz): δ 24.1, 25.9, 29.0, 29.3, 29.54, 29.57, 29.6, 46.6, 53.7, 56.0, 69.1, 109.6, 112.5, 120.2, 140.5, 147.1, 151.6, 162.2, 164.6,; IR (neat): 3338, 2926, 1600, 1507, 1448, 1261, 1217, 1024 cm$^{-1}$; MS (FAB) m/z (relative intensity) 723 ([M+2×MeOH]$^+$, 14), 691 ([M+MeOH]$^+$, 20), 659 (M$^+$, 100).

EXAMPLE 12

Synthesis of PBD Monomer—(11S,11aS)-8-Hydroxy-10-(tert-butyloxycarbonyl)-7-methoxy-11-(tetrahydroxy-pyran-2-yloxy)-1,2,3,10,11,11a-hexahydro-5H-pyrrolo[2,1-c][1,4]benzodiazepine-5-one (14)

(a) N-[4-Benzyloxy-5-methoxy-2-(tert-butyloxycarbonylamino)benzoyl]-pyrrolidine-2-methanol (11)

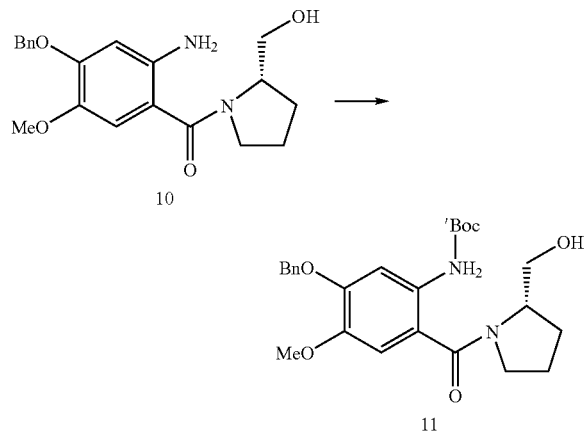

A solution of amine 10 (8 g, 22.47 mmol, 1.0 equiv) and Di-tert-butyl dicarbonate (7.35 g, 33.70 mmol, 1.5 equiv) in THF (150 mL) was heated at reflux overnight. The reaction mixture was allowed to cool to RT and excess THF was removed under reduced pressure to give the crude product. The residue was subjected to flash column chromatography (SiO$_2$, 30% EtOAc-hexane) to afford the product 11 (6.2 g, 13.59 mmol, 60%) as yellow oil: $[\alpha]^{20}_D$=−95° (c=0.17, CHCl$_3$); $^1$H NMR (CDCl$_3$, 400 MHz): δ 1.50 (s, 9H, Boc), 1.64-1.80 (m, 2H, 1-H, 2-H), 1.86-1.95 (m, 1H, 2-H), 2.14-2.23 (m, 1H, 1-H), 3.46-3.54 (m, 1H, 3-H), 3.56-3.64 (m, 1H, 3-H), 3.67-3.77 (m, 1H, 11-H), 3.81-3.89 (m, 4H, 11-H, 7-OMe), 4.29-4.48 (m, 2H, 11a-H, OH), 5.14 (m, 2H, OBn), 6.82 (s, 1H, 6-H), 7.29-7.33 (m, 1H, Ph), 7.34-7.39 (m, 2H, Ph), 7.46-7.49 (m, 2H, Ph), 7.89 (s, 1H, 9-H), 8.38 (br s, 1H, NH); $^{13}$C NMR (CDCl$_3$, 400 MHz): δ 21.8, 28.3, 28.4, 52.4, 57.5, 61.8, 67.5, 71.5, 81.1, 107.0, 112.6, 128.3, 128.6, 128.8, 129.2, 133.2, 137.1, 144.7, 151.3, 153.9, 171.9; IR (neat): cm$^{-1}$; MS (FAB) m/z (relative intensity) 479 ([M+Na]$^+$, 20), 457 (M$^+$, 100), 357 (25), 255 (23), 401 (21).

(b) (11S,11aS)-8-Benzyloxy-10-(tert-butyloxycarbonyl)-11-hydroxy-7-methoxy-1,2,3,10,11,11a-hexahydro-5H-pyrrolo[2,1-c][1,4]benzodiazepine-5-one (12)

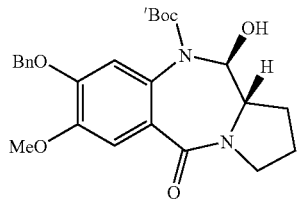

To a solution of Boc protected amine alcohol 11 (6.2 g, 13.59 mmol, 1.0 equiv) in DCM (50 mL), BAIB (4.82 g, 14.95 mmol, 1.0 equiv) and TEMPO (0.21 g, 1.35 mmol, 0.1 equiv) were added and the mixture was stirred overnight. When the reaction was complete as indicated by TLC (SiO$_2$, 50% EtOAc-hexane), the reaction mixture was diluted with DCM (100 mL) and washed with saturated Na$_2$S$_2$O$_3$ (60 mL). The aqueous layer was extracted with DCM (2×50 mL) and the combined organic layer washed with brine (50 mL) and dried (MgSO$_4$). Removal of excess solvent under reduced pressure afforded a crude solid which washed with cold EtOAc to give cyclized PBD 12 (4.9 g, 10.8 mmol, 79%) as white solid: $[\alpha]^{20}_D$=+136° (c=0.190, CHCl$_3$); $^1$H NMR (CDCl$_3$, 400 MHz): δ 1.28 (s, 9H, Boc),1.95-2.18 (m, 4H, 1-H, 2-H), 3.43-3.50 (m, 1H, 11a-H), 3.53-3.66 (m, 2H, 3-H, OH), 3.67-3.78 (m, 1H, 3-H), 3.95 (s, 3H, 7-OMe), 5.10 (d, 1H, J=12 Hz, OBn), 5.22 (d, 1H, J=12 Hz, OBn), 5.51-5.59 (m, 1H, 11-H), 6.66 (s, 1H, 9-H), 7.26 (s, 1H, 6-H), 7.33-7.34 (m, 1H, Ph), 7.38-7.41 (m, 2H, Ph), 7.41-7.45 (m, 2H, Ph); $^{13}$C NMR (CDCl$_3$, 400 MHz): δ 23.0, 28.1, 28.7, 46.3, 56.1, 59.7, 71.1, 81.6, 85.6, 110.7, 114.6, 126.0, 127.0, 128.1, 128.7, 129.1, 130.2, 136.4, 148.5, 149.8, 155.4, 167.0; IR (neat): 3374, 2974, 1699, 1623, 1602, 1511, 1454, 1433, 1324, 1161, 1050 cm$^{-1}$; MS (FAB) m/z (relative intensity) 477 ([M+Na]$^+$, 25), 455 (M$^+$, 100), 399 (94), 337 (60), 437 (45).

(c) (11S,11aS)-8-Benzyloxy-10-(tert-butyloxycarbonyl)-7-methoxy-11-(tetrahydroxy-pyran-2-yloxy)-1,2,3,10,11,11a-hexahydro-5H-pyrrolo[2,1-c][1,4]benzodiazepine-5-one (13)

(d) (11S,11aS)-8-Hydroxy-10-(tert-butyloxycarbonyl)-7-methoxy-11-(tetrahydroxy-pyran-2-yloxy)-1,2,3,10,11,11a-hexahydro-5H-pyrrolo[2,1-c][1,4]benzodiazepine-5-one (14)

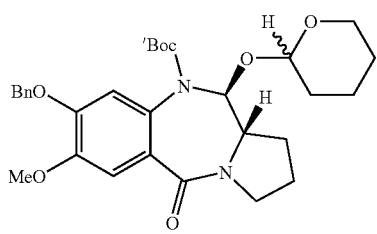

13

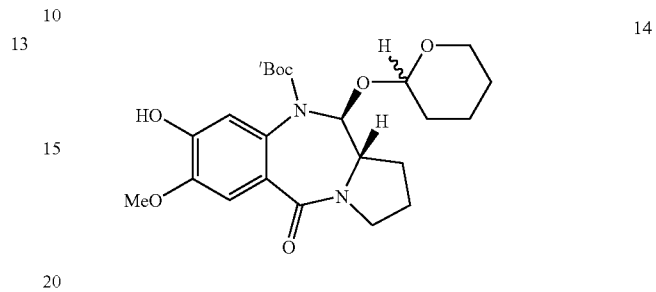

14

A catalytic amount of PTSA was added to a solution of DHP (2.87 g, 34.14 mmol, 5 equiv) in EtOAc (10 mL) at 0° C. After stirring 10 minutes, the cyclized compound 12 (3.1 g, 6.8 mmol, 1.0 equiv) was added portion-wise to the mixture and the resulting mixture was stirred until starting material disappearance by TLC ($SiO_2$, 50% EtOAc-hexane). The mixture was diluted with EtOAc (100 mL), washed with saturated $NaHCO_3$ (30 mL), brine (30 mL) and dried ($MgSO_4$). Removal of excess solvent afforded the protected compound 13 (3.5 g, 6.5 mmol, 95% yield, mixture of diastereomers from THP protecting group), which was used in the subsequent reaction without further purification: $[\alpha]^{20}_D=+64°$ (c=0.58, $CHCl_3$); $^1$H NMR ($CDCl_3$, 400 MHz): δ 1.12-1.80 (m, 30H, Boc, THP), 1.90-2.14 (m, 8H, 1-H, 2-H), 3.39-3.70 (m, 8H, 3-H, 11a-H, THP), 3.81-3.99 (m, 8H, 7-OMe, THP), 4.89-4.94 (m, 1H, THP), 5.05-5.26 (m, 5H, OBn, THP), 5.65-5.70 (d, 1H, 11-H), 5.74-5.81 (d, 1H, 11-H), 6.49 (s, 1H, 9-H), 6.88 (s, 1H, 9-H), 7.20-7.36 (m, 12H, 6-H, Ph); $^{13}$C NMR ($CDCl_3$, 400 MHz): δ 18.8, 19.6, 22.0, 22.2, 24.21, 24.25, 26.9, 27.0, 27.8, 28.0, 29.7, 30.2, 45.2, 55.06, 55.09, 58.95, 59.1, 62.2, 63.5, 69.9, 70.3, 79.8, 87.0, 90.2, 94.5, 99.5, 109.1, 109.6, 114.5, 114.7, 125.8, 126.93, 126.99, 127.65, 127.69, 128.7, 135.6, 135.7, 147.6, 147.9, 149.0, 149.1, 153.8, 166.3, 166.5; IR (neat): 3410, 2945, 2873, 1704, 1643, 1604, 1511, 1454, 1431, 1402, 1326, 1272, 1202, 1163, 1116, 1022 cm$^{-1}$; MS (FAB) m/z (relative intensity) 561 ([M+Na]$^+$, 57), 539 ($M^+$, 78), 337 (100), 540 (27), 338 (24).

A catalytic amount of 10% palladium on carbon (380 mg) was added to a solution of THP protected compound 13 (3.8 g, 7 mmol) in absolute alcohol (30 mL). The reaction mixture was hydrogenated for 3 h at 35 Psi. When the reaction was complete as indicated by TLC ($SiO_2$, 50% EtOAc-hexane) the reaction mixture was filtered through Celite, and removal of excess solvent under reduced pressure afforded the phenol 14 (2.8 g, 6.25 mmol, 90% yield, mixture of diastereomers from THP protecting group) as a white solid: $[\alpha]^{20}_D=+84°$ (c=0.48, $CHCl_3$; $^1$H NMR ($CDCl_3$, 400 MHz): δ 1.35 (s, 18H, Boc), 1.48-1.68 (m, 6H, THP), 1.69-1.88 (m, 6H, THP), 1.91-2.18 (m, 8H, 1-H, 2-H), 3.44-3.75 (m, 8H, 3-H, 11a-H, THP), 3.84-4.02 (m, 8H, 7-OMe, THP), 4.96-5.09 (m, 1H, THP), 5.10-5.18 (m, 1H, THP), 5.69-5.76 (d, 1H, 11-H), 5.77-5.87 (d, 1H, 11-H), 6.03 (s, 1H, OH), 6.14 (s, 1H, OH), 6.49 (s, 1H, 9-H), 6.86 (s, 1H, 9-H), 7.28 (s, 1H, 6-H), 7.32 (s, 1H, 6-H); $^{13}$C NMR ($CDCl_3$, 400 MHz): δ 19.9, 20.7, 23.1, 23.2, 25.1, 25.3, 28.0, 28.1, 28.9, 29.1, 30.8, 31.2, 46.3, 56.13, 56.19, 60.0, 60.2, 63.4, 64.5, 81.0, 81.1, 87.9, 91.1, 95.8, 100.7, 109.6, 110.0, 116.4, 117.0, 125.5, 125.9, 130.2, 130.5, 145.7, 145.8, 147.4, 147.5, 154.9, 155.3, 167.4, 167.6; IR (neat): 3266, 2947, 1703, 1631, 1612, 1514, 1468, 1411, 1368, 1331, 1275, 1201, 1163, 1116, 1023 cm$^{-1}$; MS (FAB) m/z (relative intensity) 471 ([M+Na]$^+$, 15), 449 ($M^+$, 99), 246 (100), 347 (25).

EXAMPLES 13-22

Synthesis of PBD Dimers Linked at the C-8 Position

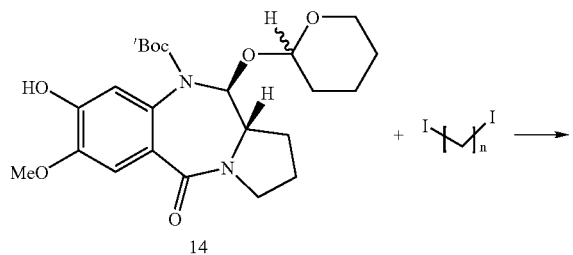

14

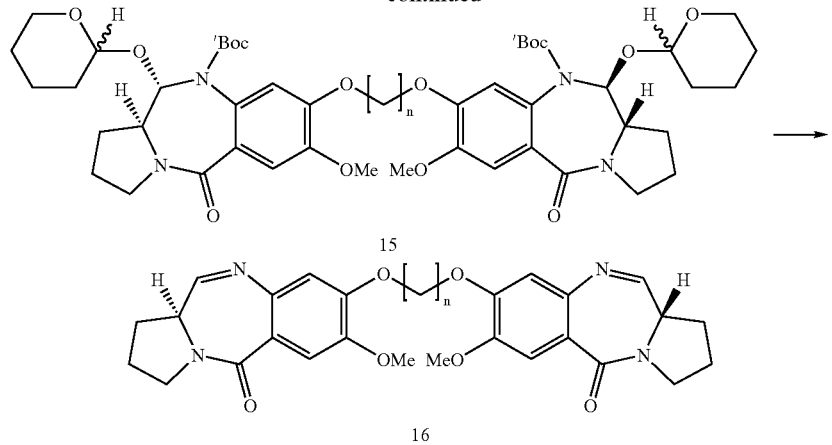

15

16 n = 3, 4, 5, 6, 7, 8, 9, 10, 11, 12

EXAMPLE 13 (n=3)

(a) 1,1'-[(Propane-1,3-diyl)dioxy]bis[(11S,11aS)-10-(tert-butyloxycarbonyl)-7-methoxy-11-(tetrahydropyran-2-yloxy)-1,2,3,10,11,11a-hexahydro-5H-pyrrolo[2,1-c][1,4]benzodiazepine-5-one] (15a)

1,3-Diiodopropane (66 mg, 0.22 mmol, 0.5 equiv) was added to the mixture of monomer 14 (0.2 g, 0.44 mmol, 1.0 equiv) and potassium carbonate (0.98 mmol, 2.2 equiv) in dry DMF (30 mL), and the resulting mixture was heated to 90° C. under a nitrogen atmosphere for 5 h. Removal of excess solvent under reduced pressure afforded a crude solid, which was subjected to flash column chromatography (SiO$_2$, 50% EtOAc-hexane) to afford the dimerized compound 15a (90 mg, 0.09 mmol, 43% yield, mixture of diastereomers from THP protecting group) as a solid: $[\alpha]^{20}_D$=+57° (c=0.14, CHCl$_3$); $^1$H NMR (CDCl$_3$, 400 MHz): δ 1.20-1.84 (m, 60H, Boc, THP), 1.91-2.20 (m, 16H, 1-H, 2-H), 2.34-2.46 (m, 4H, 13-H), 3.40-3.74 (m, 16H, 3-H, 11a-H, THP), 3.79-3.99 (m, 16H, 7-OMe, THP), 4.12-4.30 (m, 8H, 12-H), 4.97-5.15 (m, 4H, THP), 5.66-5.75 (d, 2H, 11-H), 5.77-5.89 (d, 2H, 11-H), 6.55 (s, 2H, 9-H), 6.89 (s, 2H, 9-H), 7.16 (s, 2H, 6-H), 7.20 (s, 2H, 6-H); $^{13}$C NMR (CDCl$_3$, 400 MHz): δ 19.9, 20.5, 23.1, 23.2, 25.2, 25.3, 28.1, 28.2, 28.9, 29.0, 29.1, 30.9, 31.3, 46.3, 56.0, 56.1, 60.0, 60.2, 63.4, 64.5, 65.3, 65.7, 81.0, 81.1, 88.1, 91.2, 95.7, 100.3, 110.1, 110.8, 114.7, 115.2, 127.5, 129.8, 148.5, 148.8, 150.0, 155.1, 167.4, 167.6; IR (neat): 3426, 2943, 1703, 1643, 1604, 1513, 1454, 1432, 1326, 1270, 1201, 1163, 1023 cm$^{-1}$; MS (FAB) m/z (relative intensity) 959 ([M+Na]$^+$, 100), 937 (M$^+$, 62), 835 (67), 735 (60).

(b) 1,1'-[(Propane-1,3-diyl)dioxy]bis[(11aS)-7-methoxy-1,2,3,11a-tetrahydro-5H-pyrrolo[2,1-c][1,4]benzodiazepine-5-one] (16a)

95% TFA (3 mL) was added drop-wise to dimer compound 15a (75 mg, 0.08 mmol) at 0° C. This was then stirred for 1 h and the mixture was poured into saturated NaHCO$_3$ (30 mL) solution to naturalize the reaction mixture. The mixture was extracted with chloroform (3×20 mL). The organic layer was then washed water (20 mL), brine (20 mL) then dried (MgSO$_4$) and filtrated. The excess solvent was removed under reduced pressure to give the crude product, which was subjected to flash column chromatography (SiO$_2$, 2% methanol-chloroform). Removal of excess eluent under reduced pressure without heating afforded the final product 16a (30 mg, 0.05 mmol, 70%) as a solid: $[\alpha]^{20}_D$=+477° (c=0.11, CHCl$_3$); $^1$H NMR (CDCl$_3$, 400 MHz): δ 2.01-2.06 (m, 4H, 2-H, 2'-H), 2.28-2.31 (m, 4H, 1-H, 1'-H), 2.39-2.42 (m, 2H, 13-H), 3.55-3.60 (m, 2H, 3-H, 3'-H), 3.67-3.73 (m, 2H, 11a-H, 11a'-H), 3.77-3.87 (m, 2H, 3-H, 3'-H), 3.91 (s, 6H, 7-OMe, 7'-OMe), 4.23-4.31 (m, 4H, 12-H, 12'-H), 6.84 (s, 2H, 9-H, 9'-H), 7.50 (s, 2H, 6-H, 6'-H), 7.64 (d, 2H, J=4, 11-H, 11'-H); $^{13}$C NMR (CDCl$_3$, 400 MHz): δ 24.1, 28.4, 29.6, 46.6, 53.6, 56.1, 58.4, 65.4, 110.8, 111.6, 120.4, 140.6, 147.8, 150.6, 162.3, 164.6; IR (neat): 3350, 2951, 1600, 1505, 1434, 1262, 1217, 1021 cm$^{-1}$; MS (FAB) m/z (relative intensity) 597 ([M+2×MeOH]$^+$, 16), 565 ([M+MeOH]$^+$, 5), 533 (M$^+$, 100).

EXAMPLE 14 (n=4)

(a) 1,1'-[(Butane-1,4-diyl)dioxy]bis[(11S,11aS)-10-(tert-butyloxycarbonyl)-7-methoxy-11-(tetrahydropyran-2-yloxy)-1,2,3,10,11,11a-hexahydro-5H-pyrrolo[2,1-c][1,4]benzodiazepine-5-one] (15b)

1,4-Diiodobutane (69.1 mg, 0.22 mmol, 0.5 equiv) was added to the mixture of monomer 14 (0.2 g, 0.44 mmol, 1.0 equiv) and potassium carbonate (0.98 mmol, 2.2 equiv) in dry DMF (30 mL), and the resulting mixture was heated to 90° C. under a nitrogen atmosphere for 5 h. Removal of excess solvent under reduced pressure afforded a crude solid, which was subjected to flash column chromatography (SiO$_2$, 50% EtOAc-hexane) to afford the dimerized compound 15b (210 mg, 0.22 mmol, 99% yield, mixture of diastereomers from THP protecting group) as a solid: $[\alpha]^{20}_D$=−11° (c=0.18, CHCl$_3$); $^1$H NMR (CDCl$_3$, 400 MHz): δ 1.21-1.87 (m, 60H, Boc, THP), 1.94-2.21 (m, 24H, 1-H, 2-H, 13-H), 3.43-3.77 (m, 16H, 3-H, 11a-H, THP), 3.86-4.01 (m, 16H, 7-OMe, THP), 4.02-4.19 (m, 8H, 12-H), 4.97-5.15 (m, 4H, THP), 5.66-5.75 (d, 2H, 11-H), 5.77-5.89 (d, 2H, 11-H), 6.53 (s, 2H, 9-H), 6.88 (s, 2H, 9-H), 7.20 (s, 2H, 6-H), 7.24 (s, 2H, 6-H); $^{13}$C NMR (CDCl$_3$, 400 MHz): δ 19.9, 20.6, 23.1, 23.2, 25.3, 25.9, 28.1, 28.2, 28.8, 29.1, 29.2, 30.9, 31.3, 46.3, 56.0, 56.1, 60.0, 60.1, 63.4, 64.6, 68.4, 68.8, 80.9, 81.2, 88.3, 91.2, 95.7, 100.4, 110.1, 110.7, 114.6, 115.1, 127.5, 129.8, 148.5, 148.8, 150.0, 155.0, 167.3, 167.6; IR (neat): 3472, 2945, 1704, 1643, 1604, 1513, 1454, 1432, 1327, 1271, 1202, 1163, 1023 cm$^{-1}$; MS (FAB) m/z (relative intensity) 973 ([M+Na]$^+$, 46), 951 (M$^+$, 100), 968 (86), 849 (82), 749 (34).

(b) 1,1'-[(Butane-1,4-diyl)dioxy]bis[(11aS)-7-methoxy-1,2,3,11a-tetrahydro-5H-pyrrolo[2,1-c][1,4]benzodiazepine-5-one] (16b)

95% TFA (3 mL) was added drop-wise to dimer compound 15b (170 mg, 0.17 mmol) at 0° C. This was then stirred for 1 hr and the mixture was poured into saturated NaHCO$_3$ (30 mL) solution to naturalize the reaction mixture. The mixture was extracted with chloroform (3×20 mL). The organic layer was then washed water (20 mL), brine (20 mL) then dried (MgSO$_4$) and filtrated. The excess solvent was removed under reduced pressure to give the crude product, which was subjected to flash column chromatography (SiO$_2$, 2% methanol-chloroform). Removal of excess eluent under reduced pressure without heating afforded the final product 16b (58 mg, 0.1 mmol, 62%) as a solid: $[\alpha]^{20}_D$=+517° (c=0.18, CHCl$_3$); $^1$H NMR (CDCl$_3$, 400 MHz): δ 2.04-2.09 (m, 8H, 2-H, 2'-H, 13-H, 13'-H), 2.30-2.36 (m, 4H, 1-H, 1'-H), 3.57-3.62 (m, 2H, 3-H, 3'-H), 3.71-3.74 (m, 2H, 11a-H, 11a'-H), 3.79-3.85 (m, 2H, 3-H, 3'-H), 3.93 (s, 6H, 7-OMe, 7'-OMe), 4.11-4.21 (m, 4H, 12-H, 12'-H), 6.82 (s, 2H, 9-H, 9'-H), 7.52 (s, 2H, 6-H, 6'-H), 7.66 (d, 2H, J=4; 11-H, 11'-H); $^{13}$C NMR (CDCl$_3$, 400 MHz): δ 24.1, 25.7, 29.4, 46.6, 53.7, 56.1, 68.5, 110.5, 111.5, 120.2, 140.6, 147.8, 150.7, 162.3, 164.6; IR (neat): 3316, 2972, 1601, 1505, 1433, 1381, 1262, 1217, 1091 cm$^{-1}$; MS (FAB) m/z (relative intensity) 611 ([M+2×MeOH]$^+$, 32), 579 ([M+MeOH]$^+$, 11), 547 (M$^+$, 100).

EXAMPLE 15 (n=5)

(a) 1,1'-[(Pentane-1,5-diyl)dioxy]bis[(11S,11aS)-10-(tert-butyloxycarbonyl)-7-methoxy-11-(tetrahydropyran-2-yloxy)-1,2,3,10,11,11a-hexahydro-5H-pyrrolo[2,1-c][1,4]benzodiazepine-5-one] (15c)

1,5-Diiodopentane (72.2 mg, 0.22 mmol, 0.5 equiv) was added to the mixture of monomer 14 (0.2 g, 0.44 mmol, 1.0 equiv) and potassium carbonate (0.98 mmol, 2.2 equiv) in dry DMF (30 mL), and the resulting mixture was heated to 90° C. under a nitrogen atmosphere for 5 h. Removal of excess solvent under reduced pressure afforded a crude solid, which was subjected to flash column chromatography (SiO$_2$, 50% EtOAc-hexane) to afford the dimerized compound 15c (212 mg, 0.21 mmol, 98% yield, mixture of diastereomers from THP protecting group) as a solid: $[\alpha]^{20}_D$=+40° (c=0.22, CHCl$_3$); $^1$H NMR (CDCl$_3$, 400 MHz): δ 1.21-1.83 (m, 64H, 14-H, Boc, THP), 1.88-2.18 (m, 24H, 1-H, 2-H, 13-H), 3.41-3.73 (m, 16H, 3-H, 11a-H, THP), 3.84-4.10 (m, 24H, 12-H, 7-OMe, THP), 4.97-5.15 (m, 4H, THP), 5.66-5.75 (d, 2H, 11-H), 5.77-5.89 (d, 2H, 11-H), 6.50(s, 2H, 9-H), 6.84 (s, 2H, 9-H), 7.17 (s, 2H, 6-H), 7.21 (s, 2H, 6-H); $^{13}$C NMR (CDCl$_3$, 400 MHz): δ 19.9, 20.5, 21.0, 22.7, 23.1, 23.3, 25.3, 28.1, 28.2, 28.9, 29.1, 31.0, 31.3, 46.3, 56.0, 56.1, 60.0, 60.1, 63.4, 64.6, 68.7, 69.0, 80.9, 81.3, 88.2, 91.2, 95.7, 100.4, 110.2, 110.7, 114.5, 115.0, 126.3, 129.7, 129.8, 148.5, 148.8, 150.0, 155.1, 167.4, 167.6; IR (neat): 3431, 2945, 1704, 1643, 1604, 1513, 1453, 1432, 1327, 1271, 1202, 1163, 1023 cm$^{-1}$; MS (FAB) m/z (relative intensity) 987 ([M+Na]$^+$, 37), 965 (M$^+$, 100), 763 (92), 863 (75), 982 (49).

(b) 1,1'-[(Pentane-1,5-diyl)dioxy]bis[(11aS)-7-methoxy-1,2,3,11a-tetrahydro-5H-pyrrolo[2,1-c][1,4]benzodiazepine-5-one] (16c)

95% TFA (3 mL) was added drop-wise to dimer compound 15c (180 mg, 0.19 mmol) at 0° C. This was then stirred for 1 hr and the mixture was poured into saturated NaHCO$_3$ (30 mL) solution to naturalize the reaction mixture. The mixture was extracted with chloroform (3×20 mL). The organic layer was then washed water (20 mL), brine (20 mL) then dried (MgSO$_4$) and filtrated. The excess solvent was removed under reduced pressure to give the crude product, which was subjected to flash column chromatography (SiO$_2$, 2% methanol-chloroform). Removal of excess eluent under reduced pressure without heating afforded the final product 16c (70 mg, 0.12 mmol, 65%) as a solid: $[\alpha]^{20}_D$=+626° (c=0.17, CHCl$_3$); $^1$H NMR (CDCl$_3$, 400 MHz): δ 1.62-1.71 (m, 2H, 14-H), 1.89-1.99 (m, 4H, 13-H, 13'-H), 2.0-2.11 (m, 4H, 2-H, 2'-H), 2.25-2.36 (m, 4H, 1-H, 1'-H), 3.53-3.62 (m, 2H, 3-H, 3'-H), 3.66-3.76 (m, 2H, 11a-H, 11a'-H), 3.77-3.85 (m, 2H, 3-H, 3'-H), 3.92 (s, 6H, 7-OMe, 7'-OMe), 4.01-4.16 (m, 4H, 12-H, 12'-H), 6.78 (s, 2H, 9-H, 9'-H), 7.50 (s, 2H, 6-H, 6'-H), 7.64 (d, 2H, J=4, 11-H, 11'-H); $^{13}$C NMR (CDCl$_3$, 400 MHz): δ 22.5, 29.6, 46.6, 53.7, 56.1, 68.7, 110.5, 111.6, 120.1, 140.6, 147.8, 150.8, 162.3, 164.6; IR (neat): 3350, 2946, 1600, 1505, 1455, 1433, 1383, 1262, 1217, 1092, 1020 cm$^{-1}$; MS (FAB) m/z (relative intensity) 625 ([M+2×MeOH]$^+$, 4), 593 ([M+MeOH]$^+$, 12), 547 (M$^+$, 100).

EXAMPLE 16 (n=6)

(a) 1,1'-[(Hexane-1,6-diyl)dioxy]bis[(11S,11aS)-10-(tert-butyloxycarbonyl)-7-methoxy-11-(tetrahydropyran-2-yloxy)-1,2,3,10,11,11a-hexahydro-5H-pyrrolo[2,1-c][1,4]benzodiazepine-5-one] (15d)

1,6-Diiodohexane (75.3 mg, 0.22 mg, 0.5 equiv) was added to the mixture of monomer 14 (0.2 g, 0.44 mmol, 1.0 equiv) and potassium carbonate (0.98 mmol, 2.2 equiv) in dry DMF (30 mL), and the resulting mixture was heated to 90° C. under a nitrogen atmosphere for 5 h. Removal of excess solvent under reduced pressure afforded a crude solid, which was subjected to flash column chromatography (SiO$_2$, 50% EtOAc-hexane) to afford the dimerized compound 15d (190 mg, 0.19 mmol, 87% yield, mixture of diastereomers from THP protecting group) as a solid: $[\alpha]^{20}_D$=+11° (c=0.18, CHCl$_3$); $^1$H NMR (CDCl$_3$, 400 MHz): δ 1.25-1.66 (m, 60H, 14-H, Boc, THP), 1.68-2.85 (m, 8H, THP), 1.86-2.20 (m, 24H, 1-H, 2-H, 13-H), 3.44-3.73 (m, 16H, 3-H, 11a-H, THP), 3.86-4.10 (m, 24H, 12-H, 7-OMe, THP), 5.01-5.17 (m, 4H, THP), 5.68-5.76 (d, 2H, 11-H), 5.78-5.89 (d, 2H, 11-H), 6.50(s, 2H, 9-H), 6.87 (s, 2H, 9-H), 7.19 (s, 2H, 6-H), 7.23 (s, 2H, 6-H); $^{13}$C NMR (CDCl$_3$, 400 MHz): δ 19.8, 20.5, 23.1, 23.2, 25.3, 25.9, 28.1, 28.2, 28.9, 29.02, 29.06, 29.1, 29.2, 30.9, 31.2, 46.3, 56.1, 56.2, 60.0, 60.1, 63.3, 64.5, 68.8, 69.1, 80.9, 81.3, 88.2, 91.2, 95.7, 100.3, 110.1, 110.6, 114.5, 115.0, 126.3, 129.8, 148.5, 148.8, 150.0, 155.1, 167.4, 167.6; IR (neat): 2944, 1704, 1643, 1605, 1513, 1454, 1432, 1327, 1272, 1202, 1164, 1023 cm$^{-1}$; MS (FAB) m/z (relative intensity) 1001 ([M+Na]$^+$, 21), 979 (M$^+$, 100), 877 (26), 777 (17).

(b) 1,1'-[(Hexane-1,6-diyl)dioxy]bis[(11aS)-7-methoxy-1,2,3,11a-tetrahydro-5H-pyrrolo[2,1-c][1,4]benzodiazepine-5-one] (16d)

95% TFA (3 mL) was added drop-wise to dimer compound 15d (190 mg, 0.19 mmol) at 0° C. This was then stirred for 1 hr and the mixture was poured into saturated NaHCO$_3$ (30 mL) solution to naturalize the reaction mixture. The mixture was extracted with chloroform (3×20 mL). The organic layer was then washed water (20 mL), brine (20 mL) and dried (MgSO$_4$) and filtrated. The excess solvent was removed under reduced pressure to give the crude product, which was subjected to flash column chromatography (SiO$_2$, 2% methanol-chloroform). Removal of excess eluent under reduced pressure without heating afforded the final product 16d (99 mg, 0.17 mmol, 90%) as a solid: $[\alpha]^{20}{}_D$=+474° (c=0.19, CHCl$_3$); $^1$H NMR (CDCl$_3$, 400 MHz): δ 1.49-1.65 (m, 4H, 14-H, 14'-H), 1.82-1.97 (m, 4H, 13-H, 13'-H), 1.99-2.13 (m, 4H, 2-H, 2'-H), 2.26-2.41 (m, 4H, 1-H, 1'-H), 3.53-3.65 (m, 2H, 3-H, 3'-H), 3.68-3.76 (m, 2H, 11a-H, 11a'-H), 3.77-3.89 (m, 2H, 3-H, 3'-H), 3.94 (s, 6H, 7-OMe, 7'-OMe), 4.01-4.17 (m, 4H, 12-H, 12'-H), 6.80 (s, 2H, 9-H, 9'-H), 7.52 (s, 2H, 6-H, 6'-H), 7.66 (d, 2H, J=4, 11-H, 11'-H); $^{13}$C NMR (CDCl$_3$, 400 MHz): δ 24.1, 25.7, 28.8, 29.6, 46.6, 53.7, 56.1, 68.8, 110.4, 111.6, 120.1, 140.6, 147.8, 150.8, 162.3, 164.6; IR (neat): 3318, 2943, 1601, 1506, 1454, 1433, 1382, 1262, 1217, 1021 cm$^{-1}$; MS (FAB) m/z (relative intensity) 639 ([M+2×MeOH]$^+$·, 6), 607 ([M+MeOH]$^+$·, 23), 575 (M$^+$·, 100).

EXAMPLE 17 (n=7)

(a) 1,1'-[(Heptane-1,7-diyl)dioxy]bis[(11S,11aS)-10-(tert-butyloxycarbonyl)-7-methoxy-11-(tetrahydropyran-2-yloxy)-1,2,3,10,11,11a-hexahydro-5H-pyrrolo[2,1-c][1,4]benzodiazepine-5-one] (15e)

1,7-Dibromoheptane (57.5 mg, 0.22 mmol, 0.5 equiv) was added to the mixture of monomer 14 (0.2 g, 0.44 mmol, 1.0 equiv), potassium carbonate (0.98 mmol, 2.2 equiv) and a catalytic amount of potassium iodide in dry DMF (30 mL), and the resulting mixture was heated to 90° C. under a nitrogen atmosphere for 5 h. Removal of excess solvent under reduced pressure afforded a crude solid, which was subjected to flash column chromatography (SiO$_2$, 50% EtOAc-hexane) to afford the dimerized compound 15e (200 mg, 0.20 mmol, 91% yield, mixture of diastereomers from THP protecting group) as a solid: $[\alpha]^{20}{}_D$=+34° (c=0.13, CHCl$_3$); $^1$H NMR (CDCl$_3$, 400 MHz): δ 1.25-1.64 (m, 64H, 14-H, 15-H, Boc, THP), 1.67-1.92 (m, 16H, 13-H, THP), 1.93-2.19 (m, 16H, 1-H, 2-H), 3.41-3.73 (m, 16H, 3-H, 11a-H, THP), 3.86-4.08 (m, 24H, 12-H, 7-OMe, THP), 5.01-5.17 (m, 4H, THP), 5.68-5.76 (d, 2H, 11-H), 5.78-5.89 (d, 2H, 11-H), 6.49(s, 2H, 9-H), 6.85 (s, 2H, 9-H), 7.18 (s, 2H, 6-H), 7.22 (s, 2H, 6-H); $^{13}$C NMR (CDCl$_3$, 400 MHz): δ 19.8, 20.5, 23.1, 23.3, 25.3, 25.9, 28.1, 28.2, 28.9, 29.1, 29.2, 29.3, 30.9, 31.2, 46.3, 56.1, 56.2, 60.0, 60.2, 63.3, 64.5, 68.9, 69.1, 80.9, 81.3, 88.2, 91.2, 95.7, 100.3, 110.1, 110.6, 114.4, 115.0, 121.0, 129.8, 133.4, 148.4, 148.8, 155.1, 167.4, 167.6; IR (neat): 2942, 1704, 1643, 1605, 1513, 1454, 1432, 1327, 1272, 1202, 1164, 1023 cm$^{-1}$; MS (FAB) m/z (relative intensity) 1015 ([M+Na]$^+$·, 23), 993 (M$^+$·, 100), 891 (34), 791 (25).

(b) 1,1'-[(Heptane-1,7-diyl)dioxy]bis[(11aS)-7-methoxy-1,2,3,11a-tetrahydro-5H-pyrrolo[2,1-c][1,4]benzodiazepine-5-one] (16e)

95% TFA (3 mL) was added drop-wise to dimer compound 15e (200 mg, 0.2 mmol) at 0° C. This was then stirred for 1 hr and the mixture was poured into saturated NaHCO$_3$ (30 mL) solution to naturalize the reaction mixture. The mixture was extracted with chloroform (3×20 mL). The organic layer was then washed water (20 mL), brine (20 mL) then dried (MgSO$_4$) and filtrated. The excess solvent was removed under reduced pressure to give the crude product, which was subjected to flash column chromatography (SiO$_2$, 2% methanol-chloroform). Removal of excess eluent under reduced pressure without heating afforded the final product 16e (100 mg, 0.17 mmol, 85%) as a solid: $[\alpha]^{20}{}_D$=+484° (c=0.15, CHCl$_3$); $^1$H NMR (CDCl$_3$, 400 MHz): δ 1.39-1.56 (m, 6H, 14-H, 14'-H, 15-H), 1.83-1.94 (m, 4H, 13-H, 13'-H), 2.00-2.10 (m, 4H, 2-H, 2'-H), 2.26-2.38 (m, 4H, 1-H, 1'-H), 3.54-3.63 (m, 2H, 3-H, 3'-H), 3.70-3.77 (m, 2H, 11a-H, 11a'-H), 3.79-3.91 (m, 2H, 3-H, 3'-H), 3.93 (s, 6H, 7-OMe, 7'-OMe), 4.00-4.18 (m, 4H, 12-H, 12'-H), 6.79 (s, 2H, 9-H, 9'-H), 7.51 (s, 2H, 6-H, 6'-H), 7.65 (d, 2H, J=4, 11-H, 11'-H); $^{13}$C NMR (CDCl$_3$, 400 MHz): δ 24.1, 25.8, 28.8, 29.0, 46.6, 53.7, 56.1, 68.9, 110.4, 111.6, 120.0, 140.6, 147.8, 150.9, 162.3, 164.6; IR (neat): 3317, 2936, 1620, 1599, 1505, 1453, 1430, 1381, 1261, 1216, 1092, 1020 cm$^{-1}$; MS (FAB) m/z (relative intensity) 653 ([M+2×MeOH]$^+$·, 4), 621 ([M+MeOH]$^+$·, 3), 589 (M$^+$·, 100).

EXAMPLE 18 (n=8)

(a) 1,1'-[(Octane-1,8-diyl)dioxy]bis[(11S,11aS)-10-(tert-butyloxycarbonyl)-7-methoxy-11-(tetrahydropyran-2-yloxy)-1,2,3,10,11,11a-hexahydro-5H-pyrrolo[2,1-c][1,4]benzodiazepine-5-one] (15f)

1,8-Diiodooctane (81.6 mg, 0.22 mmol, 0.5 equiv) was added to the mixture of monomer 14 (0.2 g, 0.44 mmol, 1.0 equiv) and potassium carbonate (0.98 mmol, 2.2 equiv) in dry DMF (30 mL), and the resulting mixture was heated to 90° C. under a nitrogen atmosphere for 5 h. Removal of excess solvent under reduced pressure afforded a crude solid, which was subjected to flash column chromatography (SiO$_2$, 50% EtOAc-hexane) to afford the dimerized compound 15f (190 mg, 0.18 mmol, 85% yield, mixture of diastereomers from THP protecting group) as a solid: $[\alpha]^{20}{}_D$=+28° (c=0.16, CHCl$_3$); $^1$H NMR (CDCl$_3$, 400 MHz): δ 1.22-1.64 (m, 68H, 14-H, 15-H, Boc, THP), 1.67-1.91 (m, 16H, 13-H, THP), 1.93-2.19 (m, 16H, 1-H, 2-H), 3.41-3.72 (m, 16H, 3-H, 11a-H, THP), 3.85-4.08 (m, 24H, 12-H, 7-OMe, THP), 5.01-5.17 (m, 4H, THP), 5.68-5.76 (d, 2H, 11-H), 5.78-5.89 (d, 2H, 11-H), 6.49(s, 2H, 9-H), 6.85 (s, 2H, 9-H), 7.18 (s, 2H, 6-H), 7.22 (s, 2H, 6-H); $^{13}$C NMR (CDCl$_3$, 400 MHz): δ 19.8, 20.5, 23.1, 23.2, 25.3, 25.9, 28.1, 28.2, 28.9, 29.00, 29.04, 29.1, 29.3, 30.9, 31.2, 46.3, 56.1, 56.2, 60.0, 60.2, 63.3, 64.5, 68.9, 69.2, 80.9, 81.3, 88.2, 91.2, 95.7, 100.3, 110.1, 110.6, 114.4, 115.0, 126.4, 129.8, 133.4, 148.5, 148.8, 155.1, 167.4, 167.6; IR (neat): 2940, 1703, 1642, 1604, 1513, 1454, 1432, 1327, 1272, 1202, 1163, 1023 cm$^{-1}$; MS (FAB) m/z (relative intensity) 1029 ([M+Na]$^+$·, 54), 1007 (M$^+$·, 100), 905 (28), 805 (20).

(b) 1,1'-[(Octane-1,8-diyl)dioxy]bis[(11aS)-7-methoxy-1,2,3,11a-tetrahydro-5H-pyrrolo[2,1-c][1,4]benzodiazepine-5-one] (16f)

95% TFA (3 mL) was added drop-wise to dimer compound 15f (190 mg, 0.18 mmol) at 0° C. This was then stirred for 1 hr and the mixture was poured into saturated NaHCO$_3$ (30 mL) solution to naturalize the reaction mixture. The mixture was extracted with chloroform (3×20 mL). The organic layer was then washed water (20 mL), brine (20 mL) then dried (MgSO$_4$) and filtrated. The excess solvent was removed under reduced pressure to give the crude product, which was subjected to flash column chromatography (SiO$_2$, 2% methanol-chloroform). Removal of excess eluent under reduced pressure without heating afforded the final product 16f (105 mg, 0.17 mmol, 96%) as a solid: $[\alpha]^{20}_D$=+1330° (c=0.13, CHCl$_3$); $^1$H NMR (CDCl$_3$, 400 MHz): δ 1.32-1.58 (m, 8H, 14-H, 14'-H, 15-H, 15'-H), 1.78-1.92 (m, 4H, 13-H, 13'-H), 1.93-2.10 (m, 4H, 2-H, 2'-H), 2.26-2.38 (m, 4H, 1-H, 1'-H), 3.55-3.64 (m, 2H, 3-H, 3'-H), 3.70-3.76 (m, 2H, 11a-H, 11a'-H), 3.77-3.89 (m, 2H, 3-H, 3'-H), 3.93 (s, 6H, 7-OMe, 7'-OMe), 3.98-4.15 (m, 4H, 12-H, 12'-H), 6.79 (s, 2H, 9-H, 9'-H), 7.51 (s, 2H, 6-H, 6'-H), 7.65 (d, 2H, J=4.4, 11-H, 11'-H); $^{13}$C NMR (CDCl$_3$, 400 MHz): δ 24.1, 25.8, 28.8, 29.2; 29.6; 46.6; 53.7, 56.1, 69.0, 110.4, 111.6, 120.0, 140.6, 147.8, 150.9, 162.2, 164.67; IR (neat): 3326, 2934, 1599, 1505, 1455, 1431, 1382, 1261, 1216, 1092, 1019 cm$^{-1}$; MS (FAB) m/z (relative intensity) 667 ([M+2×MeOH]$^{+\cdot}$, 3), 635 ([M+MeOH]$^{+\cdot}$, 8), 603 (M$^{+\cdot}$, 100).

EXAMPLE 19 (n=9)

(a) 1,1'-[(Nonane-1,9-diyl)dioxy]bis[(11S,11aS)-10-(tert-butyloxycarbonyl)-7-methoxy-11-(tetrahydro-pyran-2-yloxy)-1,2,3,10,11,11a-hexahydro-5H-pyrrolo[2,1-c][1,4]benzodiazepine-5-one] (15g)

1,9-Dibromononane (63.7 mg, 0.22 mmol, 0.5 equiv) was added to the mixture of monomer 14 (0.2 g, 0.44 mmol, 1.0 equiv) potassium carbonate (0.98 mmol, 2.2 equiv) and a catalytic amount of potassium iodide in dry DMF (30 mL), and the resulting mixture was heated to 90° C. under a nitrogen atmosphere for 5 h. Removal of excess solvent under reduced pressure afforded a crude solid, which was subjected to flash column chromatography (SiO$_2$, 50% EtOAc-hexane) to afford the dimerized compound 15g (200 mg, 0.19 mmol, 89% yield, mixture of diastereomers from THP protecting group) as a solid: $[\alpha]^{20}_D$=+43° (c=0.16, CHCl$_3$); $^1$H NMR (CDCl$_3$, 400 MHz): δ 1.22-1.67 (m, 72H, 14-H, 15-H, 16-H, Boc, THP), 1.68-1.91 (m, 16H, 13-H, THP), 1.92-2.19 (m, 16H, 1-H, 2-H), 3.41-3.74 (m, 16H, 3-H, 11a-H, THP), 3.85-4.09 (m, 24H, 12-H, 7-OMe, THP), 5.01-5.17 (m, 4H, THP), 5.68-5.76 (d, 2H, 11-H), 5.78-5.89 (d, 2H, 11-H), 6.49(s, 2H, 9-H), 6.85 (s, 2H, 9-H), 7.18 (s, 2H, 6-H), 7.22 (s, 2H, 6-H); $^{13}$C NMR (CDCl$_3$, 400 MHz): δ 19.8, 20.5, 23.2, 23.3, 25.3, 25.9, 28.1, 28.2, 28.9, 29.01, 29.06, 29.1, 29.4, 30.9, 31.3, 46.3, 56.1, 56.2, 60.0, 60.2, 63.3, 64.5, 69.0, 69.2, 80.9, 81.3, 88.2, 91.2, 95.7, 100.3, 110.1, 110.6, 114.5, 115.0, 126.4, 129.8, 133.4, 148.5, 148.8, 155.1, 167.4, 167.6; IR (neat): 2939, 1703, 1642, 1604, 1513, 1454, 1432, 1327, 1271, 1202, 1163, 1023 cm$^{-1}$; MS (FAB) m/z (relative intensity) 1043 ([M+Na]$^{+\cdot}$, 45), 1021 (M$^{+\cdot}$, 100), 919 (28), 819 (19).

(b) 1,1'-[(Nonane-1,9-diyl)dioxy]bis[(11aS)-7-methoxy-1,2,3,11a-tetrahydro-5H-pyrrolo[2,1-c][1,4]benzodiazepine-5-one] (16g)

95% TFA (3 mL) was added drop-wise to dimer compound 15g (200 mg, 0.19 mmol) at 0° C. This was then stirred for 1 hr and the mixture was poured into saturated NaHCO$_3$ (30 mL) solution to naturalize the reaction mixture. The mixture was extracted with chloroform (3×20 mL). The organic layer was then washed water (20 mL), brine (20 mL) then dried (MgSO$_4$) and filtrated. The excess solvent was removed under reduced pressure to give the crude product, which was subjected to flash column chromatography (SiO$_2$, 2% methanol-chloroform). Removal of excess eluent under reduced pressure without heating afforded the final product 16g (98 mg, 0.15 mmol, 83%) as a solid: $[\alpha]^{20}_D$=+864° (c=0.14, CHCl$_3$); $^1$H NMR (CDCl$_3$, 400 MHz): δ 1.32-1.52 (m, 10H, 14-H, 14'-H, 15-H, 15'-H, 16-H), 1.83-1.90 (m, 4H, 13-H, 13'-H), 2.02-2.09 (m, 4H, 2-H, 2'-H), 2.27-2.36 (m, 4H, 1-H, 1'-H), 3.54-3.64 (m, 2H, 3-H, 3'-H), 3.70-3.77 (m, 2H, 11a-H, 11a'-H), 3.78-3.88 (m, 2H, 3-H, 3'-H), 3.93 (s, 6H, 7-OMe, 7'-OMe), 3.99-4.15 (m, 4H, 12-H, 12'-H), 6.80 (s, 2H, 9-H, 9'-H), 7.51 (s, 2H, 6-H, 6'-H), 7.65 (d, 2H, J=4.4, 11-H, 11'-H); $^{13}$C NMR (CDCl$_3$, 400 MHz): δ 24.1, 25.8, 28.8, 29.2, 29.3, 29.6, 46.6, 53.7, 56.1, 69.0, 110.4, 111.6, 120.0, 140.6, 147.8, 150.9, 162.8, 164.6; IR (neat): 2934, 1622, 1599, 1557, 1505, 1455, 1429, 1382, 1339, 1260, 1216, 1092, 1020 cm$^{-1}$; MS (FAB) m/z (relative intensity) 681 ([M+2×MeOH]$^{+\cdot}$, 6), 649 ([M+MeOH]$^{+\cdot}$, 12), 617 (M$^{+\cdot}$, 100).

EXAMPLE 20 (n=10)

(a) 1,1'-[(Decane-1,10-diyl)dioxy]bis[(11S,11aS)-10-(tert-butyloxycarbonyl)-7-methoxy-11-(tetrahydro-pyran-2-yloxy)-1,2,3,10,11,11a-hexahydro-5H-pyrrolo[2,1-c][1,4]benzodiazepine-5-one] (15h)

1,10-Diiododecane (87.8 mg, 0.22 mmol, 0.5 equiv) was added to the mixture of monomer 14 (0.2 g, 0.44 mmol, 1.0 equiv) and potassium carbonate (0.98 mmol, 2.2 equiv) in dry DMF (30 mL), and the resulting mixture was heated to 90° C. under a nitrogen atmosphere for 5 h. Removal of excess solvent under reduced pressure afforded a crude solid, which was subjected to flash column chromatography (SiO$_2$, 50% EtOAc-hexane) to afford the dimerized compound 15h (180 mg, 0.17 mmol, 79% yield, mixture of diastereomers from THP protecting group) as a solid: $[\alpha]^{20}_D$=+59° (c=0.16, CHCl$_3$); $^1$H NMR (CDCl$_3$, 400 MHz): δ 1.22-1.67 (m, 76H, 14-H, 15-H, 16-H, Boc, THP), 1.68-1.91 (m, 16H, 13-H, THP), 1.92-2.19 (m, 16H, 1-H, 2-H), 3.41-3.72 (m, 16H, 3-H, 11a-H, THP), 3.85-4.09 (m, 24H, 12-H, 7-OMe, THP), 5.01-5.17 (m, 4H, THP), 5.68-5.76 (d, 2H, 11-H), 5.78-5.89 (d, 2H, 11-H), 6.50 (s, 2H, 9-H), 6.85 (s, 2H, 9-H), 7.18 (s, 2H, 6-H), 7.21 (s, 2H, 6-H); $^{13}$C NMR (CDCl$_3$, 400 MHz): δ 19.8, 20.5, 23.2, 23.3, 25.3, 26.0, 28.1, 28.2, 28.9, 29.00, 29.04, 29.1, 29.4, 29.5, 30.9, 31.3, 46.3, 56.1, 56.2, 60.0, 60.2, 63.3, 64.5, 69.0, 69.2, 80.9, 81.3, 88.2, 91.2, 95.7, 100.3, 110.1, 110.6, 114.5, 115.0, 126.4, 129.8, 133.4, 148.5, 148.8, 155.1, 167.4, 167.6; IR (neat): 2938, 1703, 1642, 1605, 1513, 1454, 1432, 1327, 1271, 1202, 1163, 1023 cm$^{-1}$; MS (FAB) m/z (relative intensity) 1057 ([M+Na]$^{+\cdot}$, 48), 1035 (M$^{+\cdot}$, 100), 933 (26), 833 (20).

(b) 1,1'-[(Decane-1,10-diyl)dioxy]bis[(11aS)-7-methoxy-1,2,3,11a-tetrahydro-5H-pyrrolo[2,1-c][1,4]benzodiazepine-5-one] (16h)

95% TFA (3 mL) was added drop-wise to dimer compound 15h (180 mg, 0.17 mmol) at 0° C. This was then stirred for 1 hr and the mixture was poured into saturated NaHCO$_3$ (30 mL) solution to naturalize the reaction mixture. The mixture was extracted with chloroform (3×20 mL). The organic layer was then washed water (20 mL), brine (20 mL) then dried (MgSO$_4$) and filtrated. The excess solvent was removed under reduced pressure to give the crude product, which was subjected to flash column chromatography (SiO$_2$, 2% methanol-chloroform). Removal of excess eluent under reduced pressure without heating afforded the final product 16h (103 mg, 0.16 mmol, 96%) as a solid: $[\alpha]^{20}_D$=+500° (c=0.11, CHCl$_3$); $^1$H NMR (CDCl$_3$, 400 MHz): δ 1.26-1.50 (m, 12H, 14-H, 14'-H, 15-H, 15'-H, 16-H, 16'-H), 1.82-1.91 (m, 4H, 13-H, 13'-H), 1.98-2.09 (m, 4H, 2-H, 2'-H), 2.25-2.35 (m, 4H, 1-H, 1'-H), 3.54-3.61 (m, 2H, 3-H, 3'-H), 3.69-3.73 (m, 2H, 11a-H, 11a'-H), 3.78-3.83 (m, 2H, 3-H, 3'-H), 3.93 (s, 6H, 7-OMe, 7'-OMe), 3.98-4.14 (m, 4H, 12-H, 12'-H), 6.79 (s, 2H, 9-H, 9'-H), 7.50 (s, 2H, 6-H, 6'-H), 7.65 (d, 2H, J=4.4, 11-H, 11'-H); $^{13}$C NMR (CDCl$_3$, 400 MHz): δ 24.1, 25.8, 28.8, 29.3, 29.4, 29.6, 46.6, 53.7, 56.1, 69.0. 110.4, 111.6, 120.0, 140.6, 147.8, 150.9, 162.3, 164.6; IR (neat): 2928, 1599, 1557, 1505, 1455, 1430, 1382, 1261, 1216, 1092, 1019 cm$^{-1}$; MS (FAB) m/z (relative intensity) 695 ([M+2×MeOH]$^{+\cdot}$, 8), 663 ([M+MeOH]$^{+\cdot}$, 16), 631 (M$^{+\cdot}$, 100).

EXAMPLE 21 (n=11)

(a) 1,1'-[(Undecane-1,11-diyl)dioxy]bis[(11S,11aS)-10-(tert-butyloxycarbonyl)-7-methoxy-11-(tetrahydro-pyran-2-yloxy)-1,2,3,10,11,11a-hexahydro-5H-pyrrolo[2,1-c][1,4]benzodiazepine-5-one] (15i)

1,11-Dibromoundecane (70.0 mg, 0.22 mmol, 0.5 equiv) was added to the mixture of monomer 14 (0.2 g, 0.44 mmol, 1.0 equiv) potassium carbonate (0.98 mmol, 2.2 equiv) and a catalytic amount of potassium iodide in dry DMF (30 mL), and the resulting mixture was heated to 90° C. under a nitrogen atmosphere for 5 h. Removal of excess solvent under reduced pressure afforded a crude solid, which was subjected to flash column chromatography (SiO$_2$, 50% EtOAc-hexane) to afford the dimerized compound 15i (210 mg, 0.20 mmol, 91% yield, mixture of diastereomers from THP protecting group) as a solid: [α]$^{20}_D$=+33° (c=0.18, CHCl$_3$); $^1$H NMR (CDCl$_3$, 400 MHz): δ 1.22-1.66 (m, 80H, 14-H, 15-H, 16-H, 17-H, Boc, THP), 1.67-1.91 (m, 16H, 13-H, THP), 1.92-2.18 (m, 16H, 1-H, 2-H), 3.41-3.72 (m, 16H, 3-H, 11a-H, THP), 3.85-4.08 (m, 24H, 12-H, 7-OMe, THP), 4.99-5.15 (m, 4H, THP), 5.67-5.75 (d, 2H, 11-H), 5.77-5.88 (d, 2H, 11-H), 6.49 (s, 2H, 9-H), 6.85 (s, 2H, 9-H), 7.18 (s, 2H, 6-H), 7.21 (s, 2H, 6-H); $^{13}$C NMR (CDCl$_3$, 400 MHz): δ 19.8, 20.5, 23.2, 23.3, 25.3, 26.0, 28.1, 28.2, 28.9, 29.0, 29.1, 29.4, 29.5, 30.9, 31.3, 46.3, 56.1, 56.2, 60.0, 60.2, 63.3, 64.5, 69.0, 69.2, 80.9, 81.3, 88.2, 91.2, 95.7, 100.3, 110.1, 110.6, 114.5, 115.0, 126.4, 129.8, 133.4, 148.5, 148.8, 155.1, 167.4, 167.7; IR (neat): 2936, 1704, 1642, 1605, 1513, 1454, 1432, 1327, 1272, 1202, 1164, 1023 cm$^{-1}$; MS (FAB) m/z (relative intensity) 1071 ([M+Na]$^{+\cdot}$, 76), 1049 (M$^{+\cdot}$, 100), 947 (24), 847 (19).

(b) 1,1'-[(Undecane-1,11-diyl)dioxy]bis[(11aS)-7-methoxy-1,2,3,11a-tetrahydro-5H-pyrrolo[2,1-c][1,4]benzodiazepine-5-one] (16i)

95% TFA (3 mL) was added drop-wise to dimer compound 15i (210 mg, 0.20 mmol) at 0° C. This was then stirred for 1 hr and the mixture was poured into saturated NaHCO$_3$ (30 mL) solution to naturalize the reaction mixture. The mixture was extracted with chloroform (3×20 mL). The organic layer was then washed water (20 mL), brine (20 mL) then dried (MgSO$_4$) and filtrated. The excess solvent was removed under reduced pressure to give the crude product, which was subjected to flash column chromatography (SiO$_2$, 2% methanol-chloroform). Removal of excess eluent under reduced pressure without heating afforded the final product 16i (105 mg, 0.16 mmol, 81%) as a solid: [α]$^{20}_D$=+623° (c=0.13, CHCl$_3$); $^1$H NMR (CDCl$_3$, 400 MHz): δ 1.26-1.52 (m, 14H, 14-H, 14'-H, 15-H, 15'-H, 16-H, 16'-H, 17-H), 1.82-1.92 (m, 4H, 13-H, 13'-H), 1.99-2.12 (m, 4H, 2-H, 2'-H), 2.26-2.38 (m, 4H, 1-H, 1'-H), 3.55-3.64 (m, 2H, 3-H, 3'-H), 3.69-3.77 (m, 2H, 11a-H, 11a'-H), 3.78-3.91 (m, 2H, 3-H, 3'-H), 3.94 (s, 6H, 7-OMe, 7'-OMe), 4.99-4.24 (m, 9H, 12-H, 12'-H), 6.80 (s, 2H, 9-H, 9'-H), 7.51 (s, 2H, 6-H, 6'-H), 7.65 (d, 2H, J=4.4, 11-H, 11'-H); $^{13}$C NMR (CDCl$_3$, 400 MHz): δ 24.1, 25.9, 28.9, 29.3, 29.4, 29.6, 46.6, 53.7, 56.1, 69.1, 110.4, 111.5, 120.0, 140.6, 147.8, 150.9, 162.3, 164.6; IR (neat): 3321, 2927, 1599, 1505, 1455, 1431, 1382, 1261, 1216, 1092, 1022 cm$^{-1}$; MS (FAB) m/z (relative intensity) 709 ([M+2×MeOH]$^{+\cdot}$, 4), 677 ([M+MeOH]$^{+\cdot}$, 11), 645 (M$^{+\cdot}$, 100).

EXAMPLE 22 (n=12)

(a) 1,1'-[(Dodecane-1,12-diyl)dioxy]bis[(11S,11aS)-10-(tert-butyloxycarbonyl)-7-methoxy-11-(tetrahydro-pyran-2-yloxy)-1,2,3,10,11,11a-hexahydro-5H-pyrrolo[2,1-c][1,4]benzodiazepine-5-one] (15j)

1,12-Dibromododecane (73.1 mg, 0.22 mmol, 0.5 equiv) was added to the mixture of monomer 14 (0.2 g, 0.44 mmol, 1.0 equiv) potassium carbonate (0.98 mmol, 2.2 equiv) and a catalytic amount of potassium iodide in dry DMF (30 mL), and the resulting mixture was heated to 90° C. under a nitrogen atmosphere for 5 h. Removal of excess solvent under reduced pressure afforded a crude solid, which was subjected to flash column chromatography (SiO$_2$, 50% EtOAc-hexane) to afford the dimerized compound 15j (210 mg, 0.19 mmol, 89% yield, mixture of diastereomers from THP protecting group) as a solid: [α]$^{20}_D$=+50° (c=0.19, CHCl$_3$); $^1$H NMR (CDCl$_3$, 400 MHz): δ 1.22-1.66 (m, 84H, 14-H, 15-H, 16-H, 17-H, Boc, THP), 1.67-1.91 (m, 16H, 13-H, THP), 1.92-2.19 (m, 16H, 1-H, 2-H), 3.41-3.72 (m, 16H, 3-H, 11a-H, THP), 3.88-4.08 (m, 24H, 12-H, 7-OMe, THP), 5.00-5.15 (m, 4H, THP), 5.67-5.74 (d, 2H, 11-H), 5.78-5.87 (d, 2H, 11-H), 6.49 (s, 2H, 9-H), 6.85 (s, 2H, 9-H), 7.18 (s, 2H, 6-H), 7.21 (s, 2H, 6-H); $^{13}$C NMR (CDCl$_3$, 400 MHz): δ 19.8, 20.5, 23.1, 23.3, 25.3, 26.0, 28.1, 28.2, 28.91, 28.98, 29.0, 29.1, 29.4, 29.5, 29.6, 30.9, 31.3, 46.3, 56.1, 56.2, 60.0, 60.2, 63.3, 64.5, 69.0, 69.2, 80.9, 81.3, 88.2, 91.2, 95.7, 100.3, 110.1, 110.6, 114.5, 115.0, 126.4, 129.8, 133.4, 148.5, 148.8, 155.1, 167.4, 167.7; IR (neat): 2932, 1702, 1644, 1604, 1512, 1454, 1431, 1326, 1271, 1202, 1163, 1023 cm$^{-1}$; MS (FAB) m/z (relative intensity) 1085 ([M+Na]$^{+\cdot}$, 43), 1063 (M$^{+\cdot}$, 100), 961 (31), 861 (17).

(b) 1,1'-[(Dodecane-1,12-diyl)dioxy]bis[(11aS)-7-methoxy-1,2,3,11a-tetrahydro-5H-pyrrolo[2,1-c][1,4]benzodiazepine-5-one] (16j)

95% TFA (3 mL) was added drop-wise to dimer compound 15j (210 mg, 0.19 mmol) at 0° C. This was then stirred for 1 hr and the mixture was poured into saturated NaHCO$_3$ (30 mL) solution to naturalize the reaction mixture. The mixture was extracted with chloroform (3×20 mL). The organic layer was then washed water (20 mL), brine (20 mL) then dried (MgSO$_4$) and filtrated. The excess solvent was removed under reduced pressure to give the crude product, which was subjected to flash column chromatography (SiO$_2$, 2% methanol-chloroform). Removal of excess eluent under reduced pressure without heating afforded the final product 16j (112 mg, 0.17 mmol, 89%) as a solid: [α]$^{20}_D$=+637° (c=0.13, CHCl$_3$); $^1$H NMR (CDCl$_3$, 400 MHz): δ 1.24-1.51 (m, 16H, 14-H, 14'-H, 15-H, 15'-H, 16-H, 16'-H, 17-H; 17'-H); 1.78-1.93 (m, 4H, 13-H, 13'-H), 1.98-2.11 (m, 4H, 2-H, 2'-H), 2.25-2.38 (m, 4H, 1-H, 1'-H), 3.54-3.64 (m, 2H, 3-H, 3'-H), 3.68-3.76 (m, 2H, 11a-H, 11a'-H), 3.77-3.89 (m, 2H, 3-H, 3'-H), 3.93 (s, 6H, 7-OMe, 7'-OMe), 3.98-4.14 (m, 4H, 12-H, 12'-H), 6.79 (s, 2H, 9-H, 9'-H), 7.50 (s, 2H, 6-H, 6'-H), 7.64 (d, 2H, J=4.4, 11-H, 11'-H); $^{13}$C NMR (CDCl$_3$, 400 MHz): δ 24.1, 25.9, 28.9, 29.3, 29.5, 29.5, 29.6, 46.6, 53.7, 56.1, 69.1, 110.4, 111.5, 120.0, 140.6, 147.8, 150.9, 162.3, 164.6; IR (neat): 3338, 2926, 1599, 1506, 1456, 1431, 1381, 1261, 1216, 1092, 1023 cm$^{-1}$; MS (FAB) m/z (relative intensity) 723 ([M+2×MeOH]$^{+\cdot}$, 9), 691 ([M+MeOH]$^{+\cdot}$, 15), 659 (M$^{+\cdot}$, 100).

EXAMPLE 23

Synthesis of PBD Monomer—(11S,11aS)-10-(tert-Butyloxycarbonyl)-8-hydroxy-7-methoxy-2-methylidene-11-(tetrahydroxy-pyran-2-yloxy)-1,2,3,10,11,11a-hexahydro-5H-pyrrolo[2,1-c][1,4]benzodiazepine-5-one (27)

(a) N-[4-Benzyloxy-5-methoxy-2-nitro-benzoyl]-(2S,4R)-[4-hydroxypyrrolidine-2-carboxylate] (19)

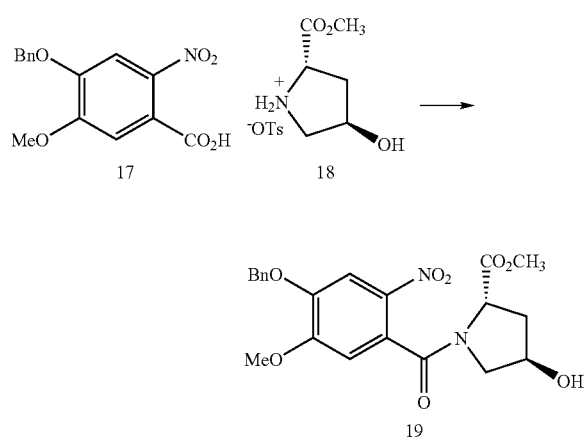

A catalytic amount of dry DMF (2 drops) was added to a solution of acid 17 (5 g, 16.4 mmol, 1.0 equiv.) in dry DCM (70 mL) and oxalyl chloride (1.6 mL, 2.3 g, 18.1 mmol, 1.1 equiv.) and then the reaction mixture was stirred overnight under nitrogen. The resulting solution was added dropwise to a solution of the salt 18 (5.74 g, 18.1 mmol, 1.1 equiv.; J. Org. Chem., 59, 13, 1994, 3621) and TEA (6.84 mL, 4.96 g, 49.2 mmol, 3.0 equiv.) in dry DCM (100 mL) at −20° C. (ethylene glycol/dry-ice). The reaction mixture was allowed to warm to room temperature and stirred overnight at which point TLC (SiO$_2$, EtOAc) revealed reaction completion. The mixture washed with 1N—HCl (50 mL), water (50 mL), saturated aqueous NaHCO$_3$ (50 mL), brine (50 mL) and dried over MgSO$_4$. The solvents were removed under vacuum to leave a yellow solid which was triturated with cold EtOAc to yield pure ester compound 19 (4.84 g, 11.2 mmol, 68%): [α]$^{28}_D$=−57° (c=0.20, CHCl$_3$); $^1$H NMR (CDCl$_3$, 400 MHz) (Rotamers): δ 1.22-1.38 (m, 1-H rotamers), 2.10-2.45 (m, 1-H), 3.10-3.18 (m, 3-H), 3.47 (s, CO$_2$Me rotamers), 3.49-3.53 (m, 3-H), 3.71-3.75 (m, 3-H rotamers), 3.80 (s, CO$_2$Me), 3.93 (s, 7-OMe rotamers), 3.97 (s, 7-OMe), 4.09-4.20 (m, 3-H rotamers, 11a-H rotamers), 4.42-4.49 (m, 2-H), 4.52-4.59 (m, 2-H rotamers), 4.83 (t, 11a-H, J=8.0 Hz), 5.20 (s, 2H, OCH$_2$Ph), 6.80 (s, 6-H rotamers), 6.85 (s, 6-H), 7.32-7.46 (m, 5H, Ph), 7.69 (s, 1H, 9-H); $^{13}$C NMR (CDCl$_3$, 100 MHz) (Rotamers): δ 38.0, 39.4, 52.3, 52.5, 54.6, 56.3, 56.6, 56.8, 57.2, 59.0, 69.2, 70.0, 71.4, 109.1, 109.7, 126.5, 127.3, 127.6, 128.5, 128.8, 135.2, 135.3, 137.3, 148.2, 148.3, 154.5, 154.9, 166.7, 167.0, 172.4, 172.5; IR (neat): 3433, 2950, 1742, 1626, 1577, 1521, 1454, 1432, 1336, 1277, 1213, 1073, 750 cm$^{-1}$; MS (ES$^+$) m/z (relative intensity) 431 ([M+H]$^+$, 100), 432 ([M+2H]$^+$, 25).

(b) N-[4-Benzyloxy-5-methoxy-2-nitro-benzoyl]-(2S,4R)-[4-hydroxy-2-(hydroxymethyl)pyrrolidine] (20)

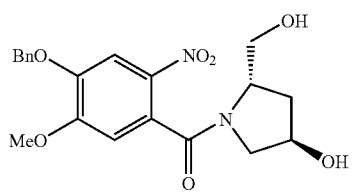

A solution of the ester 19 (3.8 g, 8.83 mmol, 1.0 equiv.) in THF (100 mL) was cooled to 0° C. and treated with LiBH$_4$ (0.29 g, 13.25 mmol, 1.5 equiv.) in portions. After stirring for 30 min at 0° C., the reaction mixture was allowed to warm to room temperature and stirred under a nitrogen atmosphere for 4 h at which time TLC (SiO$_2$, EtOAc) revealed complete consumption of ester 19. The mixture was cooled to 0° C. again and water (100 mL) was carefully added followed by 1N HCl (250 mL) which provoked vigorous effervescence. After evaporation of the THF in vacuo, the mixture was neutralised to pH 7 with 1N NaOH. The aqueous solution was then extracted with EtOAc (4×70 mL), the combined organic layers washed with brine (50 mL), dried (MgSO$_4$), filtered and evaporated in vacuo to furnished the pure diol 20 (3.2 g, 7.96 mmol, 90%), which was used in the subsequent reaction without further purification. [α]$^{29}_D$=−96° (c=0.15, CHCl$_3$); $^1$H NMR (CDCl$_3$, 400 MHz): δ 1.85-1.99 (m, 1H, 1-H), 2.09-2.28 (m, 1H, 1-H), 3.11-3.20 (m, 1H, 11-H), 3.25-3.39 (m, 1H, 11-H), 3.70-3.82 (m, 1H, 3-H), 3.85-4.04 (m, 5H, 3-H, 7-OMe, OH), 4.30-4.38 (m, 1H, 11a-H), 4.46-4.61 (m, 2H, 2-H), 5.20 (m, 2H, OCH$_2$Ph), 6.86 (s, 1H, 6-H), 7.29-7.50 (m, 5H, Ph), 7.74 (s, 1H, 9-H); $^{13}$C NMR (CDCl$_3$, 100 MHz): δ 37.1, 56.8, 56.9, 59.9, 65.0, 69.4, 71.4, 109.1, 109.3, 127.6, 127.7, 128.5, 128.8, 135.2, 137.2, 148.2, 155; IR (neat): 3357, 2938, 1614, 1576, 1520, 1454, 1434, 1333, 1276, 1220, 1069, 1048, 1006, 730, 698, 647 cm$^{-1}$; MS (ES$^+$) m/z (relative intensity) 426 ([M+Na]$^+$, 5), 403 ([M+H]$^+$, 100), 404 ([M+2H]$^+$, 40).

(c) N-[2-Amino-4-benzyloxy-5-methoxy-benzoyl]-(2S,4R)-[4-hydroxy-2-(hydroxymethyl)pyrrolidine] (21)

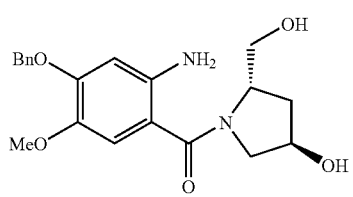

A mixture of diol 20 (26 g, 64.6 mmol, 1.0 equiv.) and SnCl$_2$.2H$_2$O (72.9 g, 323 mmol, 5.0 equiv.) in MeOH (300 mL), was heated at reflux and the progress of the reaction monitored by TLC (EtOAc). After 3 h, the MeOH was evaporated in vacuo and the resulting residue was cooled and treated carefully with saturated NaHCO$_3$ (400 mL). The mixture was diluted with EtOAc (800 mL), and after 12 h stirring at room temperature the inorganic precipitate was removed by filtration through celite. The organic layer was separated, washed with brine (100 mL), dried (MgSO$_4$), filtered and evaporated in vacuo to give a brown solid 21 which was used in the next reaction without further purification: $[\alpha]^{29}{}_D$=−69° (c=0.13, CHCl$_3$); $^1$H NMR (CDCl$_3$, 400 MHz): δ 1.70-1.82 (m, 1H, 1-H), 2.06-2.19 (m, 1H, 1-H), 3.52-3.85 (m, 9H, 3-H, 11-H, 7-OMe, 2×OH), 4.26-4.72 (m, 1H, 11a-H), 4.47-4.60 (m, 1H, 2-H), 5.10 (s, 2H, OCH$_2$Ph), 6.26 (s, 1H, 9-H), 6.78 (s, 1H, 6-H), 7.29-7.36 (m, 7H, Ph, NH$_2$); $^{13}$C NMR (CDCl$_3$, 100 MHz): δ 37.0, 57.1, 58.5, 59.0, 66.2, 69.4, 70.7, 103.4, 112.4, 112.9, 127.1, 128.0, 128.6, 136.5, 140.0, 141.9, 151.0, 172.8; IR (neat): 3358, 2939, 1619, 1589, 1512, 1455, 1432, 1408, 1263, 1231, 1171, 1113, 1012, 787, 735, 698, 644 cm$^{-1}$; MS (ES$^+$) m/z (relative intensity) 395 ([M+Na]$^{+\cdot}$, 4), 373 ([M+H]$^{+\cdot}$, 70), 374 ([M+2H]$^{+\cdot}$, 40), 256 (100), 257 (45).

(d) N-[4-Benzyloxy-5-methoxy-2-(tert-butyloxycarbonylamino)benzoyl]-(2S,4R)-[4-hydroxy-2-(hydroxymethyl)pyrrolidine] (22)

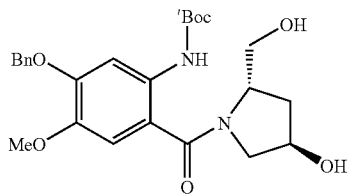

22

A solution of amine 21 (24 g, 64.6 mmol, 1.0 equiv.) and Di-tert-butyl dicarbonate (14.12 g, 64.6 mmol, 1.0 equiv.) in THF (300 mL) was heated at reflux overnight. The reaction mixture was allowed to cool to room temperature and excess THF was removed under reduced pressure to give the crude product. The residue was subjected to flash column chromatography (SiO$_2$, 30% EtOAc-hexane) to afford the product 22 (18.29 g, 38.75 mmol, 60%) as a yellow oil: $[\alpha]^{25}{}_D$=−46° (c=0.15, CHCl$_3$); $^1$H NMR (CDCl$_3$, 400 MHz): δ 1.46 (s, 9H, Boc), 1.71-1.84 (m, 1H, 1-H), 2.15-2.24 (m, 1H, 1-H), 2.78 (bs, 1H, OH), 3.54-3.76 (m, 3H, 3-H, 11-H), 3.77-3.94 (m, 4H, 3-H, 7-OMe), 4.26-4.43 (m, 1H, 11a-H), 5.15 (d, 2H, J=4.54 Hz, OCH$_2$Ph), 6.79 (s, 1H, 6-H), 7.26-7.49 (m, 6H, 9-H, Ph), 7.72 (s, 1H, NH); $^{13}$C NMR (CDCl$_3$, 100 MHz): δ 28.3, 37.2, 56.7, 59.4, 69.7, 70.8, 80.8, 108.1, 111.5, 118.8, 127.6, 128.1, 128.6, 130.4, 136.2, 145.1, 150.1, 153.6; IR (neat): 3358, 2971, 1717, 1597, 1519, 1454, 1432, 1404, 1367, 1241, 1157, 1118, 1016, 773, 698 cm$^{-1}$; MS (ES$^+$) m/z (relative intensity) 473 (M$^{+\cdot}$, 100), 474 ([M+2H]$^{+\cdot}$, 30), 256 (74), 373 (57), 416 (38).

(e) (11S,11aS)-8-Benzyloxy-10-(tert-butyloxycarbonyl)-11-hydroxy-7-methoxy-2-oxo-1,2,3,10,11,11a-hexahydro-5H-pyrrolo[2,1-c][1,4]benzodiazepine-5-one (23)

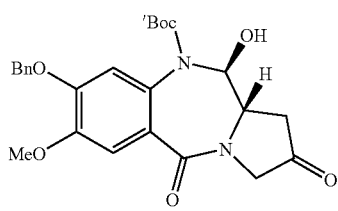

23

BAIB (17 g, 52.96 mmol, 5.0 equiv.) and TEMPO (0.17 g, 1.05 mmol, 0.1 equiv.) were added to a solution of Boc protected amine alcohol 22 (5.0 g, 10.59 mmol, 1.0 equiv.) in DCM (50 mL) and the mixture was allowed to stir overnight. When the reaction was complete as indicated by TLC (SiO$_2$, 50% EtOAc-hexane), the reaction mixture was diluted with DCM (100 mL) and washed with saturated Na$_2$S$_2$O$_3$ (60 mL). The aqueous layer was extracted with DCM (2×50 mL) and the combined organic layers were washed with brine (50 mL) and dried (MgSO$_4$). Removal of excess solvent under reduced pressure afforded a crude solid which washed with cold EtOAc to give cyclized compound 23 (2.3 g, 4.9 mmol, 46%) as a white solid: $[\alpha]^{25}{}_D$=+117° (c=0.14, CHCl$_3$); $^1$H NMR (CDCl$_3$, 400 MHz): δ 1.28 (s, 9H, Boc), 2.68-2.73 (m, 1H, 1-H), 2.90-3.02 (m, 1H, 1-H), 3.75-4.01 (m, 6H, 3-H, 11a-H, OH, 7-OMe), 4.22-4.46 (m, 1H, 3-H), 5.03-5.26 (m, 2H, OCH$_2$Ph), 5.55-5.69 (m, 1H, 11-H), 6.68 (s, 1H, 9-H), 7.23 (s, 1H, 6-H), 7.33-7.45 (m, 5H, Ph); $^{13}$C NMR (CDCl$_3$, 100 MHz): δ 28.0, 40.3, 52.6, 56.2, 56.6, 71.1, 86.0, 110.7, 114.6, 123.9, 127.0, 128.2, 128.6, 128.8, 129.1, 130.3, 136.2, 149.0, 150.5, 167.7, 207.9; IR (neat): 3389, 2978, 1762, 1700, 1637, 1603, 1511, 1456, 1431, 1368, 1329, 1256, 1221, 1157, 1118, 1059, 767 cm$^{-1}$; MS (ES$^+$) m/z (relative intensity) 469 (M$^{+\cdot}$, 27), 413 (100), 351 (61), 256 (30).

(f) (11S,11aS)-10-(tert-Butyloxycarbonyl)-8,11-dihydroxy-7-methoxy-2-oxo-1,2,3,10,11,11a-hexahydro-5H-pyrrolo[2,1-c][1,4]benzodiazepine-5-one (24)

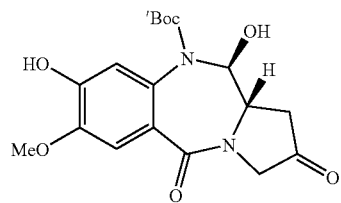

24

A catalytic amount of 10% palladium on carbon (0.23 g) was added to a solution of cyclized compound 23 (2.3 g, 4.9 mmol) in absolute alcohol (50 mL). The reaction mixture was hydrogenated for 4 h at 30 Psi. When the reaction was complete as indicated by TLC (SiO$_2$, 50% EtOAc-hexane) the reaction mixture was filtered through Celite, and removal of excess solvent under reduced pressure afforded the phenol 24 (4.7 g, 2.64 mmol, 53%) as a white solid: $[\alpha]^{25}{}_D$=+115° (c=0.10, MeOH); $^1$H NMR (CDCl$_3$, 400 MHz): δ 1.39 (s, 9H, Boc), 2.68-2.80 (m, 1H, 1-H), 2.87-3.02 (m, 1H, 1-H), 3.84-4.06 (m, 6H, 3-H, 11a-H, OH, 7-OMe), 4.22-4.35 (m, 1H, 3-H), 5.53-5.71 (m, 1H, 11-H), 6.02 (s, 1H, OH), 6.73 (s, 1H, 9-H), 7.20 (s, 1H, 6-H); $^{13}$C NMR (CDCl$_3$, 100 MHz): δ 28.1, 40.4, 52.6, 56.2, 56.7, 85.9, 110.1, 115.9, 123.1, 129.9, 145.9, 148.2, 167.8, 208.1; IR (neat): 3355, 2977, 1760, 1685, 1606, 1515, 1469, 1415, 1369, 1332, 1297, 1212, 1162, 1132, 1042, 767 cm$^{-1}$; MS (ES$^+$) m/z (relative intensity) 379 (M$^{+\cdot}$, 93), 380 ([M+2H]$^{+\cdot}$, 25), 364 (100), 396 (75), 420 (45).

(g) (11S,11aS)-10-(tert-Butyloxycarbonyl)-7-methoxy-2-oxo-8,11-di(tetrahydroxy-pyran-2-yloxy)-1,2,3,10,11,11a-hexahydro-5H-pyrrolo[2,1-c][1,4]benzodiazepine-5-one (25)

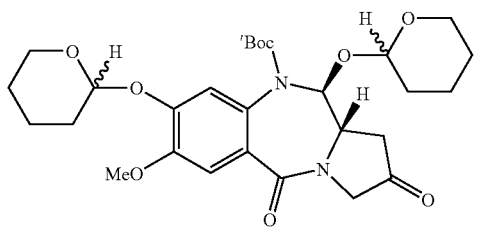

25

A catalytic amount of PTSA was added to a solution of DHP (4.8 mL, 52.8 mmol, 10.0 equiv.) in EtOAc (10 mL) at 0° C. After stirring for 10 minutes, the phenolic compound 24 (2.0 g, 5.28 mmol, 1.0 equiv.) was added portionwise to the mixture and stirred until the disappearance of starting material was observed by TLC (SiO$_2$, 50% EtOAc-hexane). The mixture was diluted with EtOAc (100 mL), washed with saturated NaHCO$_3$ (30 mL), brine (30 mL) and dried (MgSO$_4$). Removal of excess solvent under reduced pressure afforded a crude solid which was subjected to flash column chromatography (SiO$_2$, 30% EtOAc-hexane) to give the protected compound 25 (1.8 g, 3.4 mmol, 65% yield, mixture of diastereomers from THP protecting group) $[\alpha]^{24}_D$=+110° (c=0.10, CHCl$_3$); $^1$H NMR (CDCl$_3$, 400 MHz): δ 1.34 (s, 18H, Boc), 1.42-1.81 (m, 18H, THP), 1.83-2.14 (m, 6H, THP), 2.55-2.65 (m, 1H, 1-H), 2.82-3.00 (m, 3H, 1-H), 3.51-3.66 (m, 4H, THP), 3.82-4.05(m, 14H, 3-H, 11a-H, 7-OMe, THP), 4.23-4.44 (m, 2H, 3-H), 4.96-5.06 (m, 1H, THP), 5.12-5.20 (m, 1H, THP), 5.26-5.41 (m, 1H, THP), 5.43-5.50 (m, 1H, THP), 5.77-5.86 (d, 1H, 11-H), 5.90-6.01 (d, 1H, 11-H), 6.86-6.90 (2×s, 1H, 9-H), 7.15-7.22 (3×s, 3H, 6-H, 9-H); $^{13}$C NMR (CDCl$_3$, 100 MHz): δ 18.2, 18.6, 18.8, 20.0, 20.2, 20.6, 25.1, 25.2 (×2), 27.9, 28.0, 28.1, 28.2, 30.0, 30.1, 30.6, 30.9, 31.1, 31.2, 40.4, 40.8, 52.7, 52.8, 56.2, 56.9, 57.0, 61.6, 62.0, 62.1, 63.6, 63.9, 64.7, 81.5, 88.3, 91.2, 96.6, 100.4, 110.5, 110.9, 118.2, 125.9, 129.5, 129.6, 148.6, 148.7, 168.1, 168.2, 208.3, 208.5; IR (neat): 2941, 1762, 1702, 1649, 1604, 1508, 1454, 1429, 1393, 1367, 1324, 1256, 1197, 1162, 1115, 1072, 1021, 960, 904, 870, 731 cm$^{-1}$; MS (ES$^+$) m/z (relative intensity) 547 (M$^+$·, 56), 548 ([M+2H]$^+$·, 20), 261 (100), 345 (94).

(h) (11S,11aS)-10-(tert-Butyloxycarbonyl)-7-methoxy-2-methylidene-8,11-di(tetrahydroxy-pyran-2-yloxy)-1,2,3,10,11,11a-hexahydro-5H-pyrrolo[2,1-c][1,4]benzodiazepine-5-one (26)

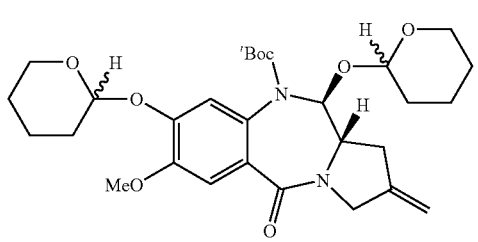

26

Potassium tert-butoxide (4.1 g, 36 mmol, 10.0 equiv.) was added portionwise to a suspension of methyltriphenylphosphonium bromide (12.8 g, 36 mmol, 10.0 equiv.) in THF (50 mL) at 0° C., under nitrogen. After stirring for 2 h at 0° C., a solution of the ketone 25 (2.0 g, 3.6 mmol, 1.0 equiv.) was added dropwise and the mixture allowed to warm to room temperature. After stirring overnight, the reaction mixture was diluted with EtOAc (250 mL) and water (250 mL) and the organic layer separated, washed with brine, dried (MgSO$_4$), filtered and evaporated in vacuo to give a dark red oil, which was shown to contain a mixture of several components by TLC (SiO$_2$, 50% EtOAc-hexane). Purification by flash chromatography (SiO$_2$, 30% EtOAc-hexane) isolated the pure olefin 26 as a white solid (1.4 g, 2.59 mmol, 72% yield, mixture of diastereomers from THP protecting group: $[\alpha]^{22}_D$=+105° (c=0.20, CHCl$_3$); $^1$H NMR (CDCl$_3$, 400 MHz): δ 1.32 (s, 18H, Boc), 1.40-1.81 (m, 18H, THP), 1.83-2.14 (m, 6H, THP), 2.50-2.59 (m, 1H, 1-H), 2.69-2.95 (m, 3H, 1-H), 3.51-3.72 (m, 6H, 11a-H, THP), 3.82-4.03(m, 10H, 7-OMe, THP), 4.04-4.18 (m, 2H, 3-H), 4.23-4.38 (m, 2H, 3-H), 4.96-5.19 (m, 6H, 2a-H, THP), 5.22-5.48 (m, 2H, THP), 5.62-5.71 (d, 1H, 11-H), 5.75-5.87 (d, 1H, 11-H), 6.77-6.90 (2×s, 1H, 9-H), 7.10-7.20 (3×s, 3H, 6-H, 9-H); $^{13}$C NMR (CDCl$_3$, 100 MHz): δ 18.3, 18.7, 18.8, 19.9, 20.0, 20.6, 25.1, 25.2, 25.3, 27.9, 28.0, 28.2, 30.1, 30.2, 30.4, 30.7, 31.0, 31.2, 31.3, 35.1, 35.5, 50.7, 56.2, 59.8, 60.0, 61.6, 62.0, 62.1, 63.4, 63.6, 64.5, 81.1, 81.2, 88.0, 90.9, 96.0, 96.3, 96.5, 96.7, 98.4, 99.6, 100.3, 109.4, 109.5, 110.3, 110.7, 118.1, 120.3, 127.3, 129.6, 129.7, 129.8, 142.3, 147.9, 148.1, 148.8, 149.4, 155.2, 168.1, 168.2; IR (neat): 2940, 2866, 1702, 1639, 1604, 1508, 1453, 1431, 1393, 1367, 1324, 1198, 1162, 1114, 1072, 1019, 960, 906, 870, 727, 644 cm$^{-1}$; MS (ES$^+$) m/z (relative intensity) 545 (M$^+$·, 38), 546 ([M+2H]$^+$·, 15), 343 (100), 259 (95), 344 (23).

(i) (11S,11aS)-10-(tert-Butyloxycarbonyl)-8-hydroxy-7-methoxy-2-methylidene-11-(tetrahydroxy-pyran-2-yloxy)-1,2,3,10,11,11a-hexahydro-5H-pyrrolo[2,1-c][1,4]benzodiazepine-5-one (27)

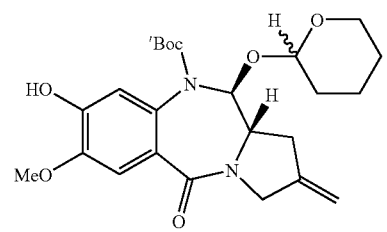

27

A solution of THF/AcOH/H$_2$O (2:1:1, 5 mL) was added to the olefin 26 (1.8 g, 3.3 mmol) and the resulting mixture was stirred for 3 h at which point TLC (SiO$_2$, 50% EtOAc-hexane) revealed complete reaction. The mixture was then neutralized with saturated NaHCO$_3$ and extracted with EtOAc (3×30 mL) and the combined organic layers were washed with brine (50 mL) and dried (MgSO$_4$). Removal of excess solvent under reduced pressure gave the crude product. The residue was subjected to flash chromatography (SiO$_2$, 50% EtOAc-hexane) to afford the product 27 (1.34 g, 2.9 mmol, 87% yield, mixture of diastereomers from THP protecting group): $[\alpha]^{27}_D$=+81° (c=0.16, CHCl$_3$); $^1$H NMR (CDCl$_3$, 400 MHz): δ 1.32 (s, 18H, Boc), 1.45-1.64 (m, 8H, THP), 1.66-1.84 (m, 4H, THP), 2.50-2.58 (m, 1H, 1-H), 2.68-2.80 (m, 1H, 1-H), 2.84-2.96 (m, 2H, 1-H), 3.51-3.67 (m, 4H, 11a-H, THP), 3.87-4.00 (m, 8H, 7-OMe, THP), 4.04-4.18 (m, 2H, 3-H), 4.23-4.38 (m, 2H, 3-H), 4.96-5.19 (m, 6H, 2a-H, THP), 5.65-5.72 (d, 1H, 11-H), 5.75-5.88 (d, 1H, 11-H), 5.97 (s, 1H, 8-OH), 6.00 (s, 1H, 8-OH), 6.63 (s, 1H, 9-H), 6.92 (s, 1H, 9-H), 7.17 (s, 1H, 6-H), 7.21 (s, 1H, 6-H); $^{13}$C NMR (CDCl$_3$, 100 MHz): δ 20.0, 20.7, 25.1, 25.2, 28.0, 28.1, 29.7, 30.8, 31.3, 35.1, 35.4, 50.7, 56.1, 56.2, 59.8, 60.0, 63.6, 64.6, 88.0, 91.0, 96.1, 100.7, 109.4, 109.8, 116.4, 117.0, 130.3, 130.5, 142.0, 145.8, 146.0, 147.5, 147.7, 167.3, 167.5; IR (neat): 2940, 2851, 1703, 1630, 1512, 1467, 1440, 1407, 1391, 1367, 1326, 1200, 1161, 1118, 1072, 1019, 910, 730 cm$^{-1}$; MS (ES$^+$) m/z (relative intensity) 461 (M$^+$·, 75), 462 ([M+2H]$^+$·, 20), 259 (100), 260 (30), 359 (21).

EXAMPLES 24

Synthesis of C-2 Unsatured PBD Dimmers Linked at the C-8 Position solid, which was subjected to flash column chromatography (SiO$_2$, 75% EtOAc-hexane) to afford the dimerized compound 28a (77 mg, 0.074 mmol, 51% yield, mixture of diastereomers from THP protecting group) as a solid: [α]$^{26}_D$=+63° (c=0.11, CHCl$_3$); $^1$H NMR (CDCl$_3$, 400 MHz): δ 1.30-1.64 (m, 68H, 14-H, 15-H, Boc, THP), 1.71-1.94 (m, 16H, 13-H, THP), 2.51-2.62 (m, 2H, 1-H), 2.72-2.83 (m, 2H, 1-H), 2.87-2.98 (m, 4H, 1-H), 3.53-3.72 (m, 8H, 11a-H, THP), 3.85-4.19 (m, 28H, 3-H, 12-H, 7-OMe, THP), 4.27-4.38 (m, 4H, 3-H), 5.01-5.20 (m, 12H, 2a-H, THP), 5.68-5.76 (d, 2H, 11-H), 5.78-5.89 (d, 2H, 11-H), 6.51(s, 2H, 9-H), 6.87 (s, 2H, 9-H), 7.18 (s, 2H, 6-H), 7.22 (s, 2H, 6-H); $^{13}$C NMR (CDCl$_3$, 100 MHz): δ 20.0, 20.5, 25.2, 25.9, 28.1, 28.2, 29.0 (×2), 29.3, 31.0, 31.3, 35.1, 35.4, 50.6, 56.1 (×2), 60.0, 63.5, 64.4, 68.9, 69.2, 91.1, 96.4, 100.3, 109.4, 110.0, 110.5, 114.4, 114.9, 129.8, 142.8, 148.6, 148.9, 167.2, 167.4; IR (neat): 2938, 2857, 1702, 1643, 1604, 1511, 1454, 1430, 1400, 1367,

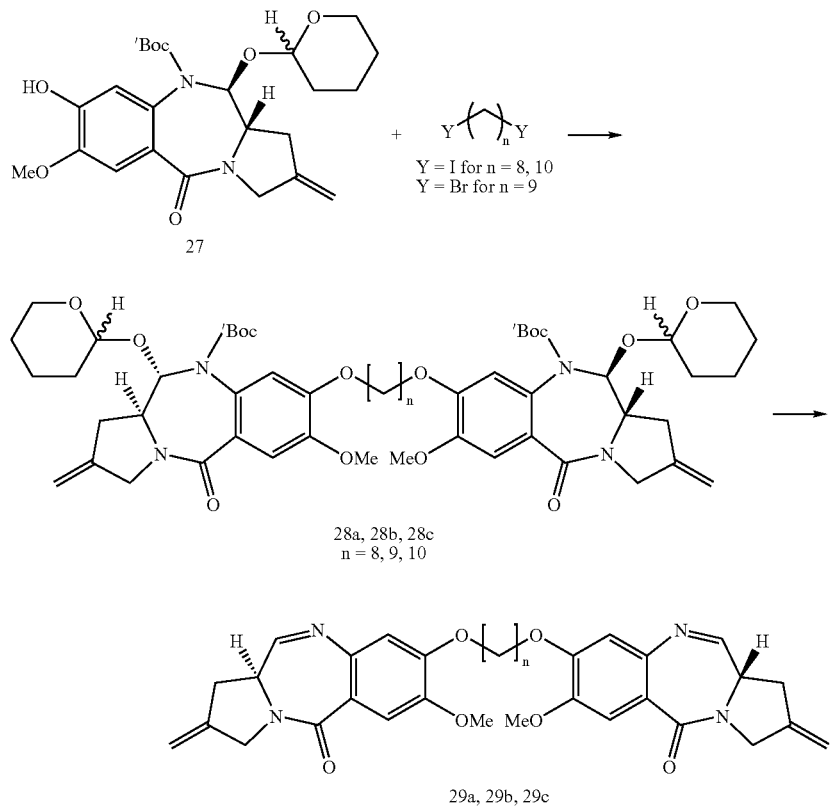

EXAMPLE 24 (n=8)

(a) 1,1'-[(Octane-1,8-diyl)dioxy]bis[(11S,11aS)-10-(tert-butyloxycarbonyl)-7-methoxy-11-(tetrahydropyran-2-yloxy)-2-methylidene-1,2,3,10,11,11a-hexahydro-5H-pyrrolo[2,1-c][1,4]benzodiazepine-5-one] (28a)

1,8-Diiodooctane (53 mg, 0.14 mmol, 0.5 equiv.) was added to the mixture of monomer 27 (134 mg, 0.29 mmol, 1.0 equiv.) and potassium carbonate (60 mg, 0.58 mmol, 2.0 equiv.) in dry DMF (30 mL), and the resulting mixture was heated to 90° C. under a nitrogen atmosphere for 4 h. Removal of excess solvent under reduced pressure afforded a crude 1325, 1273, 1254, 1211, 1163, 1118, 1072, 1019, 911, 869, 729 cm$^{-1}$; MS (ES$^+$) m/z (relative intensity) 1054 ([M+Na]$^+$·, 9), 1031 ([M+H]$^+$·, 100), 1032 ([M+2H]$^+$·, 65), 929 (46), 829 (38), 1048 (34).

(b) 1,1'-[(Octane-1,8-diyl)dioxy]bis[(11aS)-7-methoxy-2-methylene-1,2,3,11a-tetrahydro-5H-pyrrolo[2,1-c][1,4]benzodiazepine-5-one] (29a)

95% TFA (2 mL) was added dropwise to dimer compound 28a (77 mg, 0.074 mmol) at 0° C. which was stirred for 1 h and then poured into saturated aqueous NaHCO$_3$ (30 mL). The mixture was extracted with chloroform (3×20 mL) and the organic layer was then washed with water (20 mL), brine (20 mL), dried (MgSO$_4$) and filtered. The excess solvent was removed under reduced pressure to give the crude product, which was subjected to flash column chromatography (SiO$_2$, 2% methanol-chloroform). Removal of excess eluent under reduced pressure without heating afforded the final product 29a (39 mg, 0.062 mmol, 84%) as a solid: [α]$^{29}_D$=+428° (c=0.07, CHCl$_3$); $^1$H NMR (CDCl$_3$, 400 MHz): δ 1.33-1.54 (m, 8H, 14-H, 15-H), 1.78-1.93 (m, 4H, 13-H), 2.86-2.97 (m, 2H, 1-H), 3.04-3.17 (m, 2H, 1-H), 3.83-3.89 (m, 2H, 11a-H), 3.93 (s, 6H, 7-OMe), 3.99-4.12 (m, 4H, 12-H), 4.28 (s, 4H, 3-H), 5.16-5.19 (m, 4H, 2a-H), 6.79 (s, 2H, 9-H), 7.49 (s, 2H, 6-H), 7.66 (d, 2H, J=4.42 Hz, 11-H); $^{13}$C NMR (CDCl$_3$, 100 MHz): δ 25.2, 25.8, 28.8, 29.2, 35.5, 51.3, 53.8, 56.1, 58.4, 69.0, 109.3, 110.4, 111.4, 119.6, 140.7, 141.7, 147.9, 151.0, 162.4, 164.8; IR (neat): 3310, 2932, 2855, 1598, 1503, 1463, 1451, 1429, 1381, 1260, 1216, 1096, 1013, 911, 786, 729 cm$^{-1}$; MS (ES$^+$) m/z (relative intensity) 627 ([M+H]$^{+\cdot}$, 100), 628 ([M+2H]$^{+\cdot}$, 53), 332 (92), 323 (61).

EXAMPLE 25 (n=9)

(a) 1,1'-[(Nonane-1,9-diyl)dioxy]bis[(11S,11aS)-10-(tert-butyloxycarbonyl)-7-methoxy-11-(tetrahydro-pyran-2-yloxy)-2-methylidene-1,2,3,10,11,11a-hexahydro-5H-pyrrolo[2,1-c][1,4]benzodiazepine-5-one] (28b)

1,9-Dibromononane (35.75 mg, 0.125 mmol, 0.5 equiv.) was added to the mixture of monomer 27 (115 mg, 0.25 mmol, 1.0 equiv.), potassium carbonate (53 mg, 0.50 mmol, 2.0 equiv.) and a catalytic amount of potassium iodide (1 mg) in dry DMF (30 mL), and the resulting mixture was heated to 90° C. under a nitrogen atmosphere for 5 h. Removal of excess solvent under reduced pressure afforded a crude solid, which was subjected to flash column chromatography (SiO$_2$, 50% EtOAc-hexane) to afford the dimerized compound 28b (89 mg, 0.085 mmol, 68% yield, mixture of diastereomers from THP protecting group) as a solid: [α]$^{29}_D$=+36° (c=0.11, CHCl$_3$); $^1$H NMR (CDCl$_3$, 400 MHz): δ 1.25-1.67 (m, 72H, 14-H, 15-H, 16-H, Boc, THP), 1.70-1.91 (m, 16H, 13-H, THP), 2.51-2.58 (m, 2H, 1-H), 2.72-2.81 (m, 2H, 1-H), 2.84-2.97 (m, 4H, 1-H), 3.51-3.65 (m, 8H, 11a-H, THP), 3.85-4.19 (m, 28H, 3-H, 12-H, 7-OMe, THP), 4.26-4.38 (m, 4H, 3-H), 5.00-5.18 (m, 12H, 2a-H, THP), 5.65-5.74 (d, 2H, 11-H), 5.76-5.88 (d, 2H, 11-H), 6.49 (s, 2H, 9-H), 6.85 (s, 2H, 9-H), 7.16 (s, 2H, 6-H), 7.19 (s, 2H, 6-H); $^{13}$C NMR (CDCl$_3$, 100 MHz): δ 20.2, 25.2, 25.9, 28.1, 28.2, 29.0, 29.3, 29.4, 31.0, 31.1, 35.1, 35.4, 50.6, 56.1, 59.9, 60.0, 63.5, 68.9, 69.2, 91.1, 96.2, 100.3, 109.3, 110.4, 110.5, 114.8, 114.9, 129.8, 142.1, 148.6, 148.9, 167.2; IR (neat): 2935, 2856, 1704, 1645, 1604, 1511, 1454, 1430, 1401, 1367, 1325, 1255, 1210, 1163, 1119, 1020, 907, 729 cm$^{-1}$; MS (ES$^+$) m/z (relative intensity) 1068 ([M+Na]$^{+\cdot}$, 13), 1045 ([M+H]$^{+\cdot}$, 100), 1046 ([M+2H]$^{+\cdot}$, 65), 943 (42), 843 (28).

(b) 1,1'-[(Nonane-1,9-diyl)dioxy]bis[(11aS)-7-methoxy-2-methylene-1,2,3,11a-tetrahydro-5H-pyrrolo[2,1-c][1,4]benzodiazepine-5-one] (29b)

95% TFA (2 mL) was added dropwise to dimer compound 28b (89 mg, 0.085 mmol) at 0° C. which was stirred for 1 h and then poured into saturated aqueous NaHCO$_3$ (30 mL). The mixture was extracted with chloroform (3×20 mL) and the organic layer washed with water (20 mL), brine (20 mL), dried (MgSO$_4$) and filtered. The excess solvent was removed under reduced pressure to give the crude product, which was subjected to flash column chromatography (SiO$_2$, 2% methanol-chloroform). Removal of excess eluent under reduced pressure without heating afforded the final product 29b (30 mg, 0.046 mmol, 55%) as a solid: [α]$^{27}_D$=+308° (c=0.24, CHCl$_3$); $^1$H NMR (CDCl$_3$, 400 MHz): δ 1.30-1.39 (m, 6H, 15-H, 16-H), 1.40-1.50 (m, 4H, 14-H), 1.82-1.91 (m, 4H, 13-H), 2.89-2.97 (m, 2H, 1-H), 3.06-3.16 (m, 2H, 1-H), 3.81-3.90 (m, 2H, 11a-H), 3.93 (s, 6H, 7-OMe), 3.98-4.10 (m, 4H, 12-H), 4.28 (s, 4H, 3-H), 5.16-5.19 (m, 4H, 2a-H), 6.79 (s, 2H, 9-H), 7.48 (s, 2H, 6-H), 7.66 (d, 2H, J=4.44 Hz, 11-H); $^{13}$C NMR (CDCl$_3$, 100 MHz): δ 25.8, 28.8, 29.2, 29.4, 35.2, 51.3, 53.8, 56.2, 69.0, 109.3, 110.3, 111.3, 119.5, 140.6, 141.7, 151.0, 162.4, 164.8; IR (neat): 2928, 2854, 1624, 1599, 1506, 1464, 1429, 1381, 1261, 1216, 1096, 729 cm$^{-1}$; MS (ES$^+$) m/z (relative intensity) 641 ([M+H]$^{+\cdot}$, 100), 642 ([M+2H]$^{+\cdot}$, 52), 339 (97).

EXAMPLE 26 (n=10)

(a) 1,1'-[(Decane-1,10-diyl)dioxy]bis[(11S,11aS)-10-(tert-butyloxycarbonyl)-7-methoxy-11-(tetrahydro-pyran-2-yloxy)-2-methylidene-1,2,3,10,11,11a-hexahydro-5H-pyrrolo[2,1-c][1,4]benzodiazepine-5-one] (28c)

1,10-Diiododecane (49.26 mg, 0.125 mmol, 0.5 equiv.) was added to the mixture of monomer 27 (115 mg, 0.25 mmol, 1.0 equiv.) and potassium carbonate (53 mg, 0.50 mmol, 2.0 equiv.) in dry DMF (30 mL), and the resulting mixture was heated to 90° C. under a nitrogen atmosphere for 5 h. Removal of excess solvent under reduced pressure afforded a crude solid, which was subjected to flash column chromatography (SiO$_2$, 60% EtOAc-hexane) to afford the dimerized compound 28c (90 mg, 0.084 mmol, 67% yield, mixture of diastereomers from THP protecting group) as a solid: [α]$^{27}_D$=+22° (c=0.11, CHCl$_3$); $^1$H NMR (CDCl$_3$, 400 MHz): δ 1.26-1.65 (m, 76H, 14-H, 15-H, 16-H, Boc, THP), 1.72-1.90 (m, 16H, 13-H, THP), 2.55-2.95 (m, 8H, 1-H), 3.53-3.69 (m, 8H, 11a-H, THP), 3.85-4.15 (m, 28H, 3-H, 12-H, 7-OMe, THP), 4.25-4.36 (m, 4H, 3-H), 4.97-5.18 (m, 12H, 2a-H, THP), 5.65-5.88 (m, 4H, 11-H), 6.48 (s, 3H, 9-H), 6.85 (s, 1H, 9-H), 7.15-7.19 (2×s, 4H, 6-H); $^{13}$C NMR (CDCl$_3$, 100 MHz): δ 20.0, 20.5, 25.2, 25.9, 28.1, 28.2, 29.0, 29.4, 29.5, 31.0, 31.3, 35.1, 35.4, 50.6, 56.1, 60.0, 63.5, 64.4, 68.9, 69.2, 91.1, 96.4, 100.3, 109.4, 110.0, 110.6, 114.3, 114.9, 128.4, 142.1, 148.8, 149.3, 167.3; IR (neat): 2933, 2854, 1703, 1643, 1603, 1512, 1454, 1430, 1402, 1367, 1324, 1254, 1209, 1162, 1118, 1018, 910, 860, 729 cm$^{-1}$; MS (ES$^+$) m/z (relative intensity) 1059 ([M+H]$^{+\cdot}$, 100), 1060 ([M+2H]$^{+\cdot}$, 70), 957 (50).

(b) 1,1'-[(Decane-1,10-diyl)dioxy]bis[(11aS)-7-methoxy-2-methylene-1,2,3,11a-tetrahydro-5H-pyrrolo[2,1-c][1,4]benzodiazepine-5-one] (29c)

95% TFA (2 mL) was added dropwise to dimer compound 28c (90 mg, 0.084 mmol) at 0° C. which was stirred for 1 h and then poured into saturated aqueous NaHCO$_3$ (30 mL). The mixture was extracted with chloroform (3×20 mL) and the organic layer washed with water (20 mL), brine (20 mL), dried (MgSO$_4$) and filtered. The excess solvent was removed under reduced pressure to give the crude product, which was subjected to flash column chromatography (SiO$_2$, 2% methanol-chloroform). Removal of excess eluent under reduced pressure without heating afforded the final product 29c (34 mg, 0.052 mmol, 61%) as a solid: [α]$^{26}_D$=+309° (c=0.31, CHCl$_3$); $^1$H NMR (CDCl$_3$, 400 MHz): δ 1.31-1.39 (m, 8H, 15-H, 16-H), 1.40-1.51 (m, 4H, 14-H), 1.80-1.93 (m, 4H, 13-H), 2.89-3.10 (m, 2H, 1-H), 3.06-3.19 (m, 2H, 1-H), 3.81-3.95 (m, 8H, 11a-H, 7-OMe), 3.98-4.11 (m, 4H, 12-H), 4.28 (s, 4H, 3-H), 5.16-5.18 (m, 4H, 2a-H), 6.80 (s, 2H, 9-H), 7.49 (s, 2H, 6-H), 7.66 (d, 2H, J=4.56 Hz, 11-H); $^{13}$C NMR (CDCl$_3$, 100 MHz): δ 25.8, 28.8, 29.2, 29.4, 35.2, 51.3, 53.8, 56.2, 69.0, 109.3, 110.4, 111.4, 119.5, 140.7, 141.7, 151.1, 162.4, 164.8; IR (neat): 2933, 1599, 1506, 1464, 1429, 1380, 1262, 1216; 1096, 729, 628 cm$^{-1}$; MS (ES$^+$) m/z (relative intensity) 655 ([M+H]$^{+\cdot}$, 100), 656 ([M+2H]$^{+\cdot}$, 50), 346 (97).

EXAMPLE 27

Determination of DNA Cross-Linking Ability and in vitro Cytotoxicity (a) DNA Cross-Linking The extent of DNA cross-linking induced by each PBD dimer was determined using the electrophoretic assay method of Hartley, et al. (Hartley, J. A., Berardini, M. D., and Souhami, R. L. (1991) *Anal. Biochem.* 193, 131-134) based on the principle that, following complete denaturation of linear pBR322 DNA (~4,300 bp) to the single-stranded (SS) form, an interstrand cross-link results in renaturation to double-stranded (DS) in a neutral gel.

Closed-circular DNA was linearized with HindIII, then dephosphorylated and finally 5'-singly end-labelled using [γ$^{32}$P]-ATP and polynucleotide kinase. Reactions containing 30-40 ng of DNA and the test compound were carried out in aqueous TEOA (25 mM triethanolamine, 1 mM EDTA, pH 7.2) buffer at 37° C. in a final volume of 50 μl for 2 hours. Reactions were terminated by addition of an equal volume of stop solution (0.6 M NaOAc, 20 mM EDTA, 100 μg/ml tRNA) followed by precipitation with ethanol. Following centrifugation, the supernatant was discarded and the pellet dried by lyophilization. Samples were re-suspended in 10 μl of strand separation buffer (30% DMSO, 1 mM EDTA, 0.04% bromophenol blue and 0.04% xylene cylanol) and denatured by heating to 90° C. for 2.5 min, followed by immersion in an ice/water bath. Control non-denatured samples were re-suspended in 10 μl of non-denaturing buffer solution (0.6% sucrose, 0.04% bromophenol blue in aqueous TAE buffer [40 mM Tris, 20 mM acetic acid, 2 mM EDTA, pH 8.1]) and loaded directly onto the gel for comparison.

Electrophoresis was carried out for 14-16 h at 40 V using a 0.8% submerged agarose gel (20×25×0.5 cm) in TAE buffer. Gels were dried under vacuum for 2 hour at 80° C. onto one layer each of Whatman 3MM and DE8I filter papers using a BioRad 583 gel dryer. Autoradiographs were obtained after exposure of Hyperfilm-MP film (Amersham plc, U.K.) to the dried gel for either 4 hour with a screen (or over night, without a screen, to obtain a sharper image). Film bands were quantitated using a BioRad GS-670 imaging laser densitometer. Percentage cross-linking was calculated by measuring the total DNA in each lane (summed density for the double-stranded [DS] and single-stranded [SS] bands) relative to the amount of cross-linked DNA (density of DS band alone). A dose-response curve was derived by plotting drug concentration against the determined percentage level of cross-linked DNA which was then analysed to determine the concentration of test compound that results in 50% cross-linked plasmid DNA (XL$_{50}$).

(b) In vitro Cytotoxicity (i) K562 Cells

K562 human chronic myeloid leukaemia cells were maintained in RPM1 1640 medium supplemented with 10% fetal calf serum and 2 mM glutamine at 37° C. in a humidified atmosphere containing 5% CO$_2$ and were incubated with a specified dose of drug for 1 hour or 96 hours at 37° C. in the dark. The incubation was terminated by centrifugation (5 min, 300 g) and the cells were washed once with drug-free medium. Following the appropriate drug treatment, the cells were transferred to 96-well microtiter plates (10$^4$ cells per well, 8 wells per sample). Plates were then kept in the dark at 37° C. in a humidified atmosphere containing 5% CO$_2$. The assay is based on the ability of viable cells to reduce a yellow soluble tetrazolium salt, 3-(4,5-dimethylthiazol-2-yl)-2,5-diphenyl-2H-tetrazolium bromide (MTT, Aldrich-Sigma), to an insoluble purple formazan precipitate. Following incubation of the plates for 4 days (to allow control cells to increase in number by approximately 10 fold), 20 μL of MTT solution (5 mg/mL in phosphate-buffered saline) was added to each well and the plates further incubated for 5 hours. The plates were then centrifuged for 5 minutes at 300 g and the bulk of the medium pipetted from the cell pellet leaving 10-20 μL per well. DMSO (200 μL) was added to each well and the samples agitated to ensure complete mixing. The optical density was then read at a wavelength of 550 nm on a Titertek Multiscan ELISA plate reader, and a dose-response curve was constructed. For each curve, an IC$_{50}$ value was read as the dose required to reduce the final optical density to 50% of the control value.

(ii) NCI 60 Cell Screen

The National Cancer Institute (NCI), Bethesda, Md., USA has available an in vitro cytotoxicity screen which consists of approximately 60 human tumour cell lines against which compounds are tested at a minimum of five concentrations each differing 10-fold. A 48 hour continuous exposure protocol is used, where cell viability or growth is estimated with an SRB protein assay.

The test compounds were evaluated against approximately 60 human tumour cell lines. The NCI screening procedures were described in detail by Monks and co-workers (Monks, A et al., Journal of the National Cancer Institute, 1991, 83, 757). Briefly, cell suspensions were diluted according to the particular cell type and the expected target cell density (5000-40,000 cells per well based on cell growth characteristics), and added by pipette (100 μL) into 96-well microtitre plates. The cells were allowed a preincubation period of 24 hours at 37° C. for stabilisation. Dilutions at twice the intended test concentration were added at time zero in 100 μL aliquots to the wells. The test compounds were evaluated at five 10-fold dilutions (10$^{-4}$, 10$^{-5}$, 10$^{-6}$, 10$^{-7}$ and 10$^{-8}$ μM). The test compounds were incubated for 48 hours in 5% CO$_2$ atmosphere and 100% humidity. The cells were then assayed using the sulphorhodamine B assay. A plate reader was used to read the optical densities and a microcomputer processed the readings into GI$_{50}$ values (in Moles), which is the dosage required to limit cell growth to 50%.

| Results | | | | |
|---|---|---|---|---|
| Compound number | n | NCI GI$_{50}$ (μM) | IC$_{50}$ (μM) 1 hr exposure | XL$_{50}$ (μM) |
| 9a | 3 | 8.91 | >30 | >100 |
| 9b | 4 | 28.1 | >30 | — |
| 9c | 5 | 10.2 | >30 | — |
| 9d | 6 | 4.0 | >30 | — |
| 9e | 7 | 2.69 | >30 | 20 |
| 9f | 8 | 1.17 | 9.72 | 1.8 |

-continued

| | | Results | | |
|---|---|---|---|---|
| 9g | 9 | 0.57 | 17.3 | 0.98 |
| 9h | 10 | 1.12 | 16.13 | 0.17 |
| 9i | 11 | 0.57 | 9.00 | 0.19 |
| 9j | 12 | 0.21 | 9.12 | >100 |
| 16a | 3 | 3.16 | 12.8 | 0.05 |
| 16b | 4 | 2.51 | 2.5 | 1.00 |
| 16c | 5 | 0.015 | 0.5 | 0.07 |
| 16d | 6 | 0.31 | 1.0 | 0.75 |

| Compound number | n | NCI GI$_{50}$ (μM) | IC$_{50}$ (μM) 96 hr exposure | XL$_{50}$ (μM) |
|---|---|---|---|---|
| 16e | 7 | 0.28 | — | — |
| 16f | 8 | 0.019 | 0.0045 | 1.4 |
| 16g | 9 | 0.019 | 0.026 | 1.5 |
| 16h | 10 | 0.054 | 0.352 | 5.0 |
| 16i | 11 | 0.22 | 0.689 | — |
| 16j | 12 | 0.15 | 0.645 | — |

| Compound number | n | NCI GI$_{50}$ (nM) | IC$_{50}$ (μM) 96 hr exposure | XL$_{50}$ (μM) |
|---|---|---|---|---|
| 29a | 8 | 13.80 | — | — |
| 29b | 9 | 20.89 | 33.8 | 1.50 |
| 29c | 10 | 13.18 | 100 | 3.90 |

The invention claimed is:

1. A compound of formula Ia or Ib:

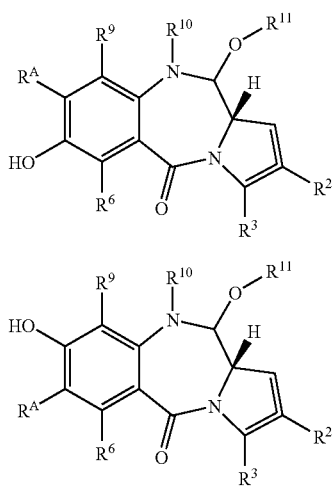

or a pharmaceutically acceptable salt thereof, wherein:
the dotted lines indicate the optional presence of a double bond between C1 and C2 or C2 and C3;
$R^2$ and $R^3$ are independently selected from —H, =O, =CH$_2$, —CN, —R, OR, halo, =CH—R, O—SO$_2$—R, CO$_2$R and COR;
$R^6$ and $R^9$ are independently selected from H, R, OH, OR, SH, SR, NH$_2$, NHR, NRR', nitro, Me$_3$Sn and halo;
where R and R' are independently selected from optionally substituted C$_{1-12}$ alkyl, heterocyclyl groups having 3 to 20 ring atoms of which 1 to 10 are heteroatoms independently selected from the group consisting of N, O and S and aryl or heteroaryl groups having 5 to 20 ring atoms, the heteroaryl groups having one or more heteroatoms independently selected from the group consisting of N, O and S, wherein the optional substituents are independently selected from halo, hydroxy, ether, alkoxy, acetal, hemiacetal, ketal, hemiketal, oxo, thione, imino, formyl, acyl, carboxy, thiocarboxy, thiolcarboxy, thionocarboxy, imidic acid, hydroxamic acid, ester, acyloxy, oxycaroyloxy, amino, amido, thioamido, acylamido, aminocaronyloxy, ureido, guanidino, tetrazolyl, amidino, nitro, nitroso, azido, cyano, isocyano, cyanato, isocyanato, thiocyano, isothiocyano, sulfhydryl, disulfide, sulfine, sulfonyl, sulfino, sulfo, sulfinate, sulfonate, sulfinyloxy, sulfonyloxy, sulfate, sulfamyl, sulfonamido, sulfamino, sulfonamino, sulfinamino, phosphino, phosphor, phosphinyl, phosphono, phosphonate, phosphonooxy, phosphate, phosphorous acid, phosphite, phosphoramidite, or phosphoramidate;
$R^A$ is selected from H, R, OR, SH, SR, NH$_2$, NHR, NRR', nitro, Me$_3$Sn and halo;
$R^{10}$ is a carbamate-based nitrogen protecting group; and
$R^{11}$ is an oxygen protecting group.

2. A compound according to claim 1, wherein $R^A$ is independently selected from H, OR, SH, SR, NH$_2$, NHR, NRR' and halo.

3. A compound according to claim 1, wherein $R^{11}$ is THP or a silyl oxygen protecting group.

4. A compound according to claim 1, wherein $R^{10}$ is BOC or Troc.

5. A compound according to claim 1, wherein $R^9$ is H.

6. A compound according to claim 1, wherein $R^2$ is R.

7. A compound according to claim 1, wherein $R^6$ is selected from H, OH, OR, SH, NH$_2$, nitro and halo.

8. A method of synthesizing a compound of formula Ia or Ib:

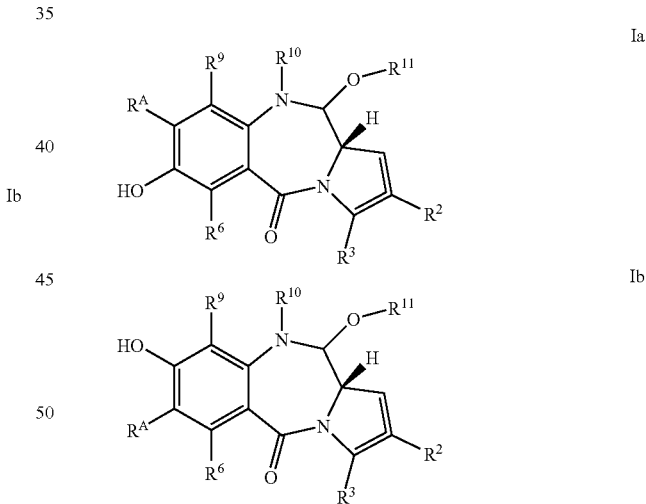

from a compound of formula IIa or IIb respectively:

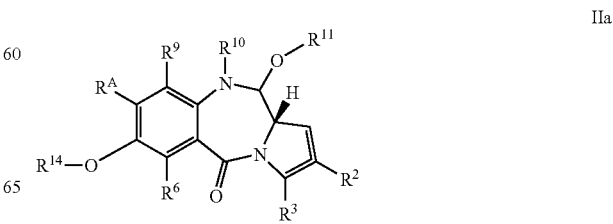

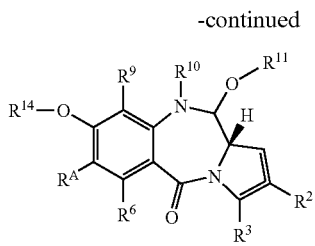

IIb

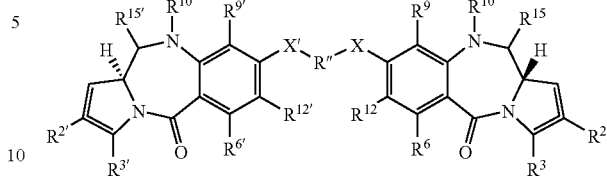

IIIb comprising deprotecting a C7 or C8 hydroxyl moiety, wherein:

the dotted lines indicates the optional presence of a double bond between C1 and C2 or C2 and C3;

$R^2$ and $R^3$ are independently selected from —H, =O, =$CH_2$, —CN, —R, OR, halo, =CH—R, O—$SO_2$—R, $CO_2R$ and COR;

$R^6$ and $R^9$ are independently selected from H, R, OH, OR, SH, SR, $NH_2$, NHR, NRR', nitro, $Me_3Sn$ and halo;

where R and R' are independently selected from optionally substituted $C_{1-12}$ alkyl, heterocyclyl groups having 3 to 20 ring atoms of which 1 to 10 are heteroatoms independently selected from the group consisting of N, O and S and aryl or heteroaryl groups having 5 to 20 ring atoms, the heteroaryl groups having one or more heteroatoms independently selected from the group consisting of N, O and S, wherein the optional substituents are independently selected from halo, hydroxy, ether, alkoxy, acetal, hemiacetal, ketal, hemiketal, oxo, thione, imino, formyl, acyl, carboxy, thiocarboxy, thiolcarboxy, thionocarboxy, imidic acid, hydroxamic acid, ester, acyloxy, oxycaroyloxy, amino, amido, thioamido, acylamido, aminocaronyloxy, ureido, guanidino, tetrazolyl, amidino, nitro, nitroso, azido, cyano, isocyano, cyanato, isocyanato, thiocyano, isothiocyano, sulfhydryl, disulfide, sulfine, sulfonyl, sulfino, sulfo, sulfinate, sulfonate, sulfinyloxy, sulfonyloxy, sulfate, sulfamyl, sulfonamido, sulfamino, sulfonamino, sulfinamino, phosphino, phosphor, phosphinyl, phosphono, phosphonate, phosphonooxy, phosphate, phosphorous acid, phosphite, phosphoramidite, or phosphoramidate;

$R^A$ is selected from H, R, OR, SH, SR, $NH_2$, NHR, NRR', nitro, $Me_3Sn$ and halo;

$R^{10}$ is a carbamate-based nitrogen protecting group;

$R^{11}$ is an oxygen protecting group; and $R^{14}$ is an oxygen protecting group orthogonal to $R^{11}$.

9. A method according to claim 8, wherein $R^{14}$ is benzyl ether and $R^A$ is OMe or H.

10. A method according to claim 8, wherein $R^{11}$ is THP or a silyl oxygen protecting group.

11. A method of synthesising a compound of formula IIIa or IIIb:

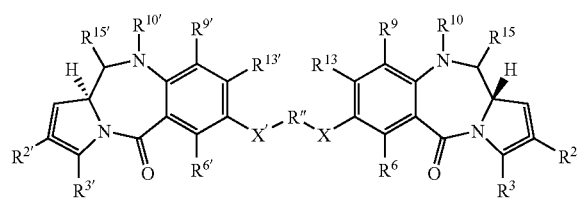

IIIa from a compound of formula Ia or Ib respectively:

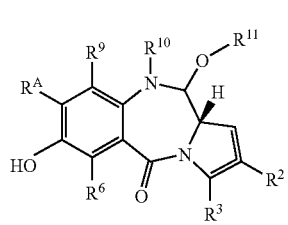

Ia

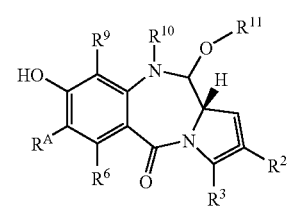

Ib wherein:

the dotted lines indicate the optional presence of a double bond between C1 and C2 or C2 and C3;

$R^2$ and $R^3$ are independently selected from —H, =O, =$CH_2$, —CN, —R, OR, halo, =CH—R, O—$SO_2$—R, $CO_2R$ and COR;

$R^6$, $R^9$, $R^{12}$ and $R^{13}$ are independently selected from H, R, OH, OR, SH, SR, $NH_2$, NHR, NRR', nitro, $Me_3Sn$ and halo; where R and R' are independently selected from optionally substituted $C_{1-12}$ alkyl, heterocyclyl groups having 3 to 20 ring atoms of which 1 to 10 are heteroatoms independently selected from the group consisting of N, O and S and aryl or heteroaryl groups having 5 to 20 ring atoms, the heteroaryl groups having one or more heteroatoms independently selected from the group consisting of N, O and S, wherein the optional substituents are independently selected from halo, hydroxy, ether, alkoxy, acetal, hemiacetal, ketal, hemiketal, oxo, thione, imino, formyl, acyl, carboxy, thiocarboxy, thiolcarboxy, thionocarboxy, imidic acid, hydroxamic acid, ester, acyloxy, oxycaroyloxy, amino, amido, thioamido, acylamido, aminocaronyloxy, ureido, guanidino, tetrazolyl, amidino, nitro, nitroso, azido, cyano, isocyano, cyanato, isocyanato, thiocyano, isothiocyano, sulfhydryl, disulfide, sulfine, sulfonyl, sulfino, sulfo, sulfinate, sulfonate, sulfinyloxy, sulfonyloxy, sulfate, sulfamyl, sulfonamido, sulfamino, sulfonamino, sulfinamino, phosphino, phosphor, phosphinyl, phosphono, phosphonate, phosphonooxy, phosphate, phosphorous acid, phosphite, phosphoramidite, or phosphoramidate;

$R^A$ is selected from H, R, OR, SH, SR, $NH_2$, NHR, NRR', nitro, $Me_3Sn$ and halo;

$R^{10}$ is a carbamate-based nitrogen protecting group and $R^{15}$ is either O—$R^{11}$, wherein $R^{11}$ is an oxygen protecting group, or OH, or $R^{10}$ and $R^{15}$ together form a double bond between N10 and C11; and where R" is a $C_{3-12}$ alkylene group, and each X is O; and $R^{2'}$, $R^{3'}$, $R^{6'}$, $R^{9'}$, $R^{10'}$, $R^{12'}$, $R^{13'}$ and $R^{15'}$ are all independently selected from the same lists as previously defined for $R^2$, $R^3$, $R^6$, $R^9$, $R^{10}$, $R^{12}$, $R^{13}$ and $R^{15}$ respectively, comprising either:

(a) reacting a compound of formula Ia or Ib with a compound having the formula Y—R"—Y' to yield a compound of formula IIIa or IIIb; or (b) (i) reacting a compound of formula Ia or Ib with a compound having the formula Y—R"—YProt, and (ii) converting YProt in the reaction product from (i) to Y', and (iii) reacting the product from (ii) with a compound of formula Ia or Ib to yield a compound of formula IIIa or IIIb;

wherein:

Y, Y' are independently selected from OH, I, Br, Cl, mesylate or tosylate;

YProt is a precursor to Y' or a chemically protected form of Y' having a protecting group that is orthogonal to $R^{10}$ and $R^{11}$.

12. A method according to claim 11, wherein Y and Y' are I.

13. A method according to claim 11, wherein Y is OH and YProt is O-benzyl.

* * * * *